US008895719B2

(12) United States Patent
Burzio et al.

(10) Patent No.: US 8,895,719 B2
(45) Date of Patent: Nov. 25, 2014

(54) MARKERS FOR PRE-CANCER AND CANCER CELLS AND THE METHOD TO INTERFERE WITH CELL PROLIFERATION THEREIN

(71) Applicant: Andes Biotechnoligies S.A., Santiago (CL)

(72) Inventors: Luis Burzio, Santiago (CL); Jaime E. Villegas, Santiago (CL); Veronica A. Burzio, Santiago (CL)

(73) Assignee: Andes Biotechnologies S.A., Santiago (CL)

( * ) Notice: Subject to any disclaimer, the term of this patent is extended or adjusted under 35 U.S.C. 154(b) by 0 days.

(21) Appl. No.: 13/627,965

(22) Filed: Sep. 26, 2012

(65) Prior Publication Data
US 2013/0149371 A1    Jun. 13, 2013

Related U.S. Application Data

(62) Division of application No. 10/557,458, filed as application No. PCT/US2004/015929 on May 21, 2004, now Pat. No. 8,318,686.

(60) Provisional application No. 60/472,106, filed on May 21, 2003.

(51) Int. Cl.
C07H 21/04    (2006.01)
C07H 21/02    (2006.01)
A61K 48/00    (2006.01)

(52) U.S. Cl.
USPC ............................ 536/24.5; 536/23.1; 514/44

(58) Field of Classification Search
None
See application file for complete search history.

(56) References Cited

U.S. PATENT DOCUMENTS

| | | | |
|---|---|---|---|
| 5,093,246 A | 3/1992 | Cech et al. | |
| 5,644,048 A | 7/1997 | Yau | |
| 5,801,154 A * | 9/1998 | Baracchini et al. | 514/44 A |
| 5,998,203 A | 12/1999 | Matulic-Adamic et al. | |
| 6,071,743 A | 6/2000 | Holzmayer et al. | |
| 6,316,210 B1 | 11/2001 | Holzmayer et al. | |
| 6,326,152 B1 | 12/2001 | Holzmayer et al. | |
| 6,417,169 B1 | 7/2002 | Wright et al. | |
| 6,426,412 B1 | 7/2002 | Holzmayer et al. | |
| 6,436,634 B1 | 8/2002 | Holzmayer et al. | |
| 6,503,533 B1 * | 1/2003 | Korba et al. | 424/450 |
| 6,537,972 B1 | 3/2003 | Holzmayer et al. | |
| 6,537,973 B1 | 3/2003 | Bennett et al. | |
| 6,544,958 B2 | 4/2003 | Wong et al. | |
| 6,555,525 B2 | 4/2003 | Burke | |
| 6,573,050 B1 | 6/2003 | Ben-David et al. | |
| 6,576,759 B2 | 6/2003 | Zeng et al. | |
| 6,656,687 B1 | 12/2003 | Hyldig-Nielsen | |
| 6,673,917 B1 | 1/2004 | Korneluk et al. | |
| 6,720,413 B1 | 4/2004 | Schweinfest et al. | |
| 6,764,822 B1 * | 7/2004 | Butler et al. | 435/6.11 |
| 8,110,364 B2 * | 2/2012 | Wohlgemuth et al. | 435/6.17 |
| 8,318,686 B2 | 11/2012 | Burzio et al. | |
| 2002/0192751 A1 | 12/2002 | Desnoyers et al. | |
| 2003/0165948 A1 * | 9/2003 | Alsmadi et al. | 435/6 |

FOREIGN PATENT DOCUMENTS

| | | | |
|---|---|---|---|
| EP | 1 229 130 A2 * | 7/2002 | 435/6 |
| JP | 11-113597 A | 4/1999 | |
| WO | WO-97/22722 A1 | 6/1997 | |
| WO | WO-98/53319 A2 | 11/1998 | |
| WO | WO-98/53319 A3 | 11/1998 | |
| WO | WO-98/54366 A1 | 12/1998 | |
| WO | WO-99/65928 A2 | 12/1999 | |
| WO | WO-00/63441 A2 | 10/2000 | |
| WO | WO-00/63441 A3 | 10/2000 | |
| WO | WO-01/16323 A2 | 3/2001 | |
| WO | WO-01/16323 A3 | 3/2001 | |
| WO | WO-01/76532 A2 | 10/2001 | |
| WO | WO-01/76532 A8 | 10/2001 | |
| WO | WO-01/76532 A9 | 10/2001 | |
| WO | WO-02/38759 A2 | 5/2002 | |
| WO | WO-02/38759 A3 | 5/2002 | |
| WO | WO-03/020220 A2 | 3/2003 | |
| WO | WO-03/020220 A3 | 3/2003 | |
| WO | WO-2005/001030 A2 | 1/2005 | |
| WO | WO-2005/001030 A3 | 1/2005 | |

OTHER PUBLICATIONS

Abraham, N. et al. (1999). "Characterization of Transgenic Mice with Targeted Disruption of the Catalytic Domain of the Double-stranded RNA-dependent Protein Kinase, PKR," *The Journal of Biological Chemistry* 274(9):5953-5962.

Adrain et al. (Jul. 23, 1999). "Regulation of Apoptotic Protease Activating Factor-1 Oligomerization and Apoptosis by the WD-40 Repeat Region," *The Journal of Biological Chemistry* 274(30):20855-20860.

(Continued)

*Primary Examiner* — Amy Bowman
(74) *Attorney, Agent, or Firm* — Morrison & Foerster LLP

(57) ABSTRACT

A novel family of human mitochondrial RNAs, referred to as chimeric RNAs, which are differentially expressed in normal, pre-cancer and cancer cells, are described. Oligonucleotides targeted to the chimeric RNAs are provided. The described oligonucleotides or their analogs can be used for cancer diagnostics and cancer therapy as well as for research. In one embodiment of this invention, these oligonucleotides hybridize with the sense or with the antisense mitochondrial chimeric RNAs, and the result of the hybridization is useful to differentiate between normal proliferating cells, pre-cancer cells and cancer cells. In another embodiment of the invention, the compositions comprise oligonucleotides that hybridize with the human chimeric RNAs resulting in cancer cell and pre-cancer cell death, while there is no effect in normal cells, constituting therefore, a novel approach for cancer therapy.

21 Claims, 12 Drawing Sheets

(56) References Cited

OTHER PUBLICATIONS

Banerjee, S. et al. (2000). "RNase L-Independence Specific 28S rRNA Cleavage in Murine Coronavirus-Infected Cells," *Journal of Virology* 74(19):8793-8802.

Bantis et al. (Feb. 2004). "Expression of p120, Ki-67 and PCNA as proliferation biomarkers in imprint smears of prostate carcinoma and their prognostic value," *Cytopathology* 15:25-31.

Beaucage, S.L. (1993). "Oligodeoxyribonucleotides Synthesis. Phosphoramidite Approach," Chapter 3 in *Methods in Molecular Biology, Protocols for Oligonucleotides and Analogs*, Agrawal, S. ed., Humana Press Inc.: Totowa, NJ, 20:33-61.

Benedict et al. "Expression and Functional Analysis of Apaf-1 Isoforms Extra WD-40 Repeat is Required for Cytochrome c Binding and Regulated Activation of Procaspse-9," *The Journal of Biological Chemistry*, vol. 275, No. 12, Issue of Mar. 24, pp. 8461-8468, 2000.

Benoist, C. et al. (Mar. 26, 1981). "In Vivo Sequence Requirements of the SV40 Early Promoter Region," *Nature* 290:304-310.

Bergeron et al. "Development and comparison of procedures for the selection of delta ribozyme cleavage sites within the hepatitis B virus," *Nucleic Acids Research* 30:4682-4691, 2002.

Bitko, V. et al. (2005). "Inhibition of Respiratory Viruses by Nasally Administered siRNA," *Nature Medicine* 11(1):50-55.

Boya et al. (2003). "Mitochondrion-targeted apoptosis regulators of viral origin," *Biochemical and Biophysical Research Communications* 304:575-581.

Brinster, R.L. et al. (Mar. 4, 1982). "Regulation of Metallothionein-thymidine Kinase Fusion Plasmids Injected into Mouse Eggs," *Nature* 296:39-42.

Burzio et al. (1997). "Environmental bioadhesion: themes and applications," *Biotechnology* 8:309-312.

Burzio, V.A. et al. (Jun. 9, 2009). "Expression of a Family of Noncoding Mitochondrial RNAs Distinguishes Normal from Cancer Cells," PNAS 106(23):9430-9434.

Capaldi et al. (May 1, 2000). "Highly efficient solid phase synthesis of oligonucleotide analogs containing phosphorodithioate linkages," *Nucleic Acids Research* 28(9):E40.

Caplen, N.J. et al. (2001). "Specific Inhibition of Gene Expression by Small Double-stranded RNAs in Invertebrate and Vertebrate Systems," *PNAS* 98(17):9742-9747.

Caplen, N.J. et al. (2000). "dsRNA-mediated Gene Silencing in Cultured Drosophila Cells: A Tissue Culture Model for the Analysis of RNA Interference," *Gene* 252:95-105.

Capodici, J. et al. (2002). "Inhibition of HIV-1 Infection by Small Interfering RNA-Mediated RNA Interference," *The Journal of Immunology* 169:5196-5201.

Carew, J.S. et al. (Dec. 9, 2002). "Mitochondrial defects in cancer," *Molecular Cancer* 1:9, webpage http://www.molecular-cancer.com/content/1/1/9.

Cella, M. et al. (1996). "Ligation of CD40 on Dendritic Cells Triggers Production of High Levels of Interleukin-12 and Enhances T Cell Stimulatory Capacity: T-T Help via APC Activation," *J. Exp. Med.* 184:747-752.

Cella, M. et al. (1999). "Maturation, Activation, and Protection of Dendritic Cells Induced by Double-Stranded RNA," *J. Exp. Med.* 189(5):821-829.

Chinnery et al. (Nov. 2000). "Mitochondrial DNA mutations in the pathogenesis of human disease," *Molecular Medicine Today* 6(11):425-432.

Clayton, D.A. et al. (Nov. 18, 1967). "Circular Dimer and Catenate Forms of Mitochondrial DNA in Human Leukaemic Leucocytes," *Nature* 216:652-657.

Clayton et al. (Apr. 1969). "Complex Mitochondrial DNA in Leukemic and Normal Human Myeloid Cells," *Proc. Natl. Acad. Sci. USA* 62(4):1077-1084.

Clayton, D.A. (2000). "Transcription and Replication of Mitochondrial DNA," *Human Reproduction* 15(Suppl. 2):11-17.

Comanor et al. (2003). "Successful HCV genotyping of previously failed and low viral load specimens using an HCV RNA qualitative assay based on transcription-mediated amplification in conjunction with the line probe assay," *Journal of Clinical Virology* 28:14-26.

Egholm et al. (Oct. 7, 1993). "PNA hybridizes to complementary oligonucleotides obeying the Watson-Crick hydrogen-bonding rules," *Nature* 365:566-568.

Elbashir et al. (May 24, 2001). "Duplexes of 21-nucleotide RNAs mediate RNA interference in cultured mammalian cells," *Nature* 411:494-498.

Falkenberg et al. (Jul. 2002). "Mitochondrial transcription factors B1 and B2 activate transcription of human mtDNA," *Nature Genetics* 31:289-294.

Ferri et al. (Nov. 2001). "Organelle-specific initiation of cell death pathways," *Nature Cell Biology* 3(11):E255-E263.

Fluiter et al. "In Vivo Tumor Growth Inhibition and Biodistribution Studies of Locked Nucleic Acid (LNA) antisense Oligonucleotides," *Nucleic Acids Research* 31:953-962, 2003.

Garcia-Calvo et al. (Dec. 4, 1998). "Inhibition of Human Caspases by Peptide-based and Macromolecular Inhibitors," *The Journal of Biological Chemistry* 273(49):32608-32613.

Giladi, H. et al. (Nov. 2003). "Small Interfering RNA Inhibits Hepatitis B Virus Replication in Mice," *Molecular Therapy* 8(5):769-776.

Grunweller et al. "Comparison of different antisense strategies in mammalian cells using locked nucleic acids, 2'-O-methyl RNA, phosphorothioates and small interfering RNA," *Nucleic Acids Research* 31:3185-3193, 2003.

Guicciardi et al. (2004). "Lysosomes in cell death," *Oncogene* 23:2881-2890.

Haseloff et al. (1989). "Sequences required for self-catalysed cleavage of the satellite RNA of tobacco ringspot virus," *Gene* 82:43-52.

Hedge et al. (Apr. 2002). "Commitment to apoptosis induced by tumor necrosis factor-$\alpha$ is dependent on caspase activity," *Apoptosis* 7(2):123-132.

Hyrup et al. (Jan. 1996). "Peptide Nucleic Acids (PNA): Synthesis, Properties and Potential Applications," *Bioorganic & Medicinal Chemistry* 4(1):5-23.

Iida, T. et al. (Sep. 15, 1998). "Essential Role of Mitochondrially Encoded Large rRNA for Germ-line Formation in *Drosophila* Embryos," *Proc. Natl. Acad. Sci. USA* 95(19):11274-11278.

Johnstone et al. (Jan. 25, 2002). "Apoptosis: A Link between Cancer Genetics and Chemotherapy," *Cell* 108:153-164.

Khabar, K.S. et al. (May 30, 2003). "RNase L Mediates Transient Control of the Interferon Response through Modulation of the Double-stranded RNA-dependent Protein Kinase PKR," *The Journal of Biological Chemistry* 278(22):20124-20132.

Kobayashi, N. et al. (1984). "Genomic Structure of HTLV (Human T-cell Leukemia Virus): Detection of Defective Genome and Its Amplification in MT-2 Cells," *The EMBO Journal* 3(6):1339-1343.

Komarov et al. (Sep. 10, 1999). "A chemical inhibitor of p53 that protects Mice for the Side Effects of Cancer Therapy," *Science* 285:1733-1737.

Krammer, P.H. (Oct. 12, 2000). "CD95's deadly mission in the immune system," *Nature* 407:789-795.

Kurreck et al. "Comparative Study of DNA Enzymes and Ribozymes against the Same Full-length Messenger RNA of the Vanilloid Receptor Subtype 1," *Journal of Biological Chemistry* 277:7099-7107, 2002.

Lewis, D.L. et al. (Sep. 2002, e-pub. Jul. 29, 2002). "Efficient Delivery of siRNA for Inhibition of Gene Expression in Postnatal Mice," *Nature Genetics* 32:107-108.

Li et al. (Jul. 5, 2001). "Endonuclease G is an apoptotic Dnase when released from mitochondria," *Nature* 412:95-99.

Liu et al. (2001). "Synthetic peptides and non-peptidic molecules as probes of structure and function of Bcl-2 family proteins and modulators of apoptosis," *Apoptosis* 6(6):453-462.

Li, K. et al. (2003). "Use of RNA Interference to Target Cyclin E-overexpressing Hepatocellular Carcinoma," *Cancer Research* 63:3593-3597.

Lodish H. et al. "Regulatory Sequences in Eukaryotic Protein-Coding Genes," *Molecular Cell Biology* 4th Edition, New York: W.H. Freeman, 2000.

Lu, P.Y. et al. (Jun. 2003). "siRNA-mediated Antitumorigenesis for Drug Target Validation and Therapeutics," *Current Opinion in Molecular Therapeutics* 5(3):225-234.

(56) References Cited

OTHER PUBLICATIONS

Mag, M. et al. (1991). "Synthesis and Selective Cleavage of an Oligodeoxynucleotide Containing a Bridged Internucleotide 5'-Phosphorothioate Linkage," *Nucleic Acids Research* 19(7):1437-1441.

Mahato et al. (Jan. 2005). "Modulation of gene expression by antisense and antigene oligodeoxynucleotides and small interfering RNA," *Expert Opinion on Drug Delivery* vol. 2, No. 1, pp. 3-28.

Martins et al. "The Serine Protease Omi/HtrA2 Regulates Apoptosis by Binding XIAP through a Reaper-like Motif," *The Journal of Biological Chemistry* vol. 277, Issue of Jan. 4, pp. 439-444, 2002.

McCulloch et al. (Feb. 2002). "A Human Mitochondrial Transcription Factor Is Related to RNA Adenine Methyltransferases and Binds S-Adenosylmethionine," *Molecular and Cellular Biology*, 22(4):1116-1125.

McKay et al. "Characterization of a Potent and Specific Class of Antisense Oligonucleotide Inhibitor of Human Protein Kinase C-α Expression," *The Journal of Biological Chemistry* vol. 274, No. 3, Issue of Jan. 15, pp. 1715-1722, 1999.

McManus et al. (Oct. 2002). "Gene Silencing in Mammals by Small Interfering RNAs," *Nat. Rev. Genet.* 3(10):737-747.

Meier et al. (Oct. 12, 2000). "Apoptosis in development," *Nature* 407:796-801.

Minks, M.A. et al. (1979). "Structural Requirements of Double-stranded RNA for the Activation of 2',5'-Oligo(A) Polymerase and Protein Kinase of Interferon-treated HeLa Cells," *The Journal of Biological Chemistry* 254(20):10180-10183.

Myers et al. (Aug. 6, 1991). "Reverse Transcription and DNA Amplification by a *Thermus thermophilus* DNA Polymerase," *Biochemistry* 30(31):7661-7666.

Nielsen, P.E. et al. (1993). "Peptide Nucleic Acids (PNA): Oligonucleotide Analogs with a Polyamide Backbone," Chapter 19 in *Antisense Research and Applications*, Crooke, S.T. et al. eds., CRC Press, Inc.: Boca Raton, Florida, pp. 363-373.

Pang, Q. et al. (2003). "Nucleophosmin Interacts with and Inhibits the Catalytic Function of Eukaryotic Initiation Factor 2 Kinase PKR," *The Journal of Biological Chemistry* 278(43):41709-41717.

Parisi, M.A. et al. (May 17, 1991). "Similarity of Human Mitochondrial Transcription Factor 1 to High Mobility Group Proteins," *Science* 252:965-969.

Parrella et al. "Detection of Mitochondrial DNA Mutations in Primary Breast Cancer and Fine-Needle Aspirates," *Cancer Research* 61, 7623-7626, Oct. 15, 2001.

Pastorino et al. "Targeted Liposomal c-myc Antisense Oligodeoxynucleotides Induce Apoptosis and Inhibit Tumor Growth and Metastases in Human Melanoma Models," *Clinical Cancer Research* vol. 9, pp. 4595-4605, 2003.

Patry, C. et al. (2003). "Small Interfering RNA-Mediated Reduction in Heterogeneous Nuclear Ribonucleoparticule A1/A2 Proteins Induces Apoptosis in Human Cancer Cells but not in Normal Mortal Cell Lines," *Cancer Research* 63:7679-7688.

Perantoni, A.O. (1998). "Carcinogenesis," Chapter 3 in *The Biological Basis of Cancer*, McKinnell, R.G. et al. eds., Cambridge University Press: Cambridge, UK, pp. 79-114.

Prakash et al. "2'-*O*[2-[(*N,N*-dimethylamino)oxy]ethyl]-modified Oligonucleotides inhibit expression of mRNA in vitro and in Vivo," *Nucleic Acids Research* 32(2):828-833, 2004.

Rait et al. "Tumor-Targeting, Systemically Delivered Antisense HER-2 Chemosensitizes Human Breast Cancer Xenografts Irrespective of HER-2 Levels," *Molecular Medicine* vol. 8, pp. 475-486, 2002.

Rampino et al. (Feb. 14, 1997). "Somatic Frameshift Mutations in the BAX Gene in Colon Cancers of the Microsatellite Mutator Phenotype," *Science* 275:967-969.

Randall, G. et al. (2003). "Clearance of Replicating Hepatitis C Virus Replicon RNAs in Cell Culture by Small Interfering RNAs," *PNAS* 100(1):235-240.

Rantanen et al. (Jan. 2003). "Characterization of the mouse genes for mitochondrial transcription factors B1 and B2," *Mammalian Genome* 14:1-6.

Ravagnan et al. (Sep. 2001). "Heat-Shock Protein 70 antagonizes apoptosis-inducing factor," *Nature Cell Biology* 3:839-843.

Reed, J.C. (Sep. 1999). "Dysregulation of Apoptosis in Cancer," *Journal of Clinical Oncology* 17(9):2941-2953.

Rossi, J.J. (1994) "Making ribozymes work in cells," *Current Biology* 4(5):469-471.

Samejima et al. "CAD/SFF40 Nuclease is Dispensible for High Molecular Weight DNA Cleavage and Stage I Chromation Condensation in Apoptosis," vol. 276, No. 48, Issue of Nov. 30, pp. 45427-45432, 2001.

Scherer et al. (2003)."Approaches for the sequence-specific knockdown of mRNA," *Nat. Biotechnol.* 21(12):1457-1465.

Shuey et al. (Feb. 10, 1985). "Characterization of an RNA Polymerase Activity from HeLa Cell Mitochondria, Which Initiates Transcription at the Heavy Strand rRNA Promoter and the Light Strand Promoter in Human Mitochondrial DNA," *The Journal of Biological Chemistry* 260(3):1952-1958.

Song, K. et al. (2000). "Tumor Necrosis Factor-related Apoptosis-inducing Ligand (TRAIL) is an Inhibitor of Autoimmune Inflammation and Cell Cycle Progression," *J. Exp. Med.* 191(7):1095-1103.

Soutschek, J. et al. (2004). "Therapeutic Silencing of an Endogenous Gene by Systemic Administration of Modified siRNAs," *Nature* 432:173-178.

Stephens et al. "Antisense Oligonucleotide Therapy in Cancer," *Curr. Opin. Mol. Therapeut.* 5:118-122, 2003.

Summerton, J. (1999). "Morpholino antisense oligomers: the case for an Rnase H-independent structural type," *Biochimica et Biophysica Acta* 1489:141-158.

Suzuki et al. (Sep. 2001). "A Serine Protease, HtrA2, Is Released from the Mitochondria and Interacts with XIAP, Inducing Cell Death," *Molecular Cell* 8(3):613-621.

Taanman, J.-W. (Feb. 1999). "The mitochondrial genome: structure, transcription, translation, and replication," *Biochimica et Biophysica Acta* 1410(2):103-123.

Tan et al. "Comprehensive Scanning of Somatic Mitochondrial DNA Mutations in Breast Cancer," *Cancer Research* 62, 972-976, Feb. 15, 2002.

Teitz et al. (May 2000). "Caspase 8 is deleted of silenced preferentially in childhood neurobastomas with amplification of MYCN," *Nature Medicine* 6(5):529-535.

Tidd et al. (2000). "Oligodeoxynucleotide 5mers containing a 5'-CpG induce apoptosis through a mitochondrial mechanism in T lymphocytic leukemia cells," *Nucleic Acids Research* 28(11):2242-2250.

Tiranti et al. (1997). "Identification of the gene encoding the human mitochondrial RNA polymerase (h-mtRPOL) by cyberscreening of the Expressed Sequence Tags database," *Human Molecular Generics* 6(4):615-625.

Tompkins, S.M. et al. (2004). "Protection Against Lethal Influenza Virus Challenge by RNA Interference in Vivo," *PNAS* 101(23):8682-8686.

Verhagen et al. (2002). "Cell death regulation by the mammalian IAP antagonist Diablo/Smac," *Apoptosis* 7:163-166.

Verma, U.N. et al. (Apr. 2003). "Small Interfering RNAs Directed Against B-Catenin Inhibit the in Vitro and in Vivo Growth of Colon Cancer Cells," *Clinical Cancer Research* 9(4):12911300.

Vickers et al. "Efficient Reduction of Target RNAs by Small Interfering RNA and Rnase H-dependent Antisense Agents," *The Journal of Biological Chemistry* vol. 278, No. 9, Issue of Feb. 28, 2003 pp. 7108-7118.

Vidalain, P.-O. et al. (2001). "Cytotoxic Activity of Human Dendritic Cells is Differentially Regulated by Double-Stranded RNA and CD40 Ligand," *The Journal of Immunology* 167:3765-3772.

Villegas et al. (2002). "A putative RNA editing from U to C in a mouse mitochondrial transcript," *Nucleic Acids Research* 30(9):1895-1901.

Villegas et al. (Sep. 2000). "A Novel Chimeric Mitochondrial RNA Localized in the Nucleus of Mouse Sperm," *DNA and Cell Biology* 19(9):579-588.

Villegas, J. et al. "Localization of the 16S Mitochondrial rRNA in the Nucleus of Mammalian Spermatogenic Cells," *Molecular Human Reproduction* 2002, pp. 997-983, vol. 8, No. 11.

(56) References Cited

OTHER PUBLICATIONS

Vogelstein, B. et al. (Nov. 16, 2000). "Surfing the p53 Network," *Nature* 408:307-310.

Wacheck et al. "Small Interfering RNA Targeting Bcl-2 Sensitizes Malignant Melanoma," *Oligonucleotides* 13:393-400, 2003.

Wagner et al. "Nucleotide sequence of the thymidine kinase gene of herpes simplex virus type 1," *Proc. Natl. Acad. Sci USA* vol. 78, No. 3, pp. 1441-1445, Mar. 1981.

Wahlestedt et al. (May 9, 2000). "Potent and nontoxic antisense oligonucleotides containing locked nucleic acids," *PNAS* 97(10):5633-5638.

Wang, L. et al. (2002). "Noncoding RNA Danger Motifs Bridge Innate and Adaptive Immunity and are Potent Adjuvants for Vaccination," *The Journal of Clinical Investigation* 110(8):1175-1884.

Warburg, O. (Feb. 24, 1956). "On the Origin of Cancer Cells," *Science* 123(3191):309-314.

Wu, X. et al. (Jan. 2003). "Immunofluorescent labeling of cancer marker Her2 and other cellular targets with semiconductor quantum dots," *Nat. Biotechnol.* 21:41-46.

Yamamoto, T. et al. (Dec. 1980). "Identification of a Functional Promoter in the Long Terminal Repeat of Rous Sarcoma Virus," *Cell* 22:787-797.

Yang et al. "C-Jun NH2-Terminal Kinase Mediates Proliferation and Tumor Growth of Human Prostate Carcinoma," *Clinical Cancer Research* 9:391-401, 2003.

Ying, C. et al. (Sep. 19, 2003). "Selective Inhibition of Hepatitis B Virus Replication by RNA Interference," *Biochemical and Biophysical Research Communications* 309(2):482-484.

Yu et al. (2001). "Pharmacokinetics and Pharmacodynamics of an Antisense Phosphorothioate Oligonucleotide Targeting Fas mRNA in Mice," *J. Pharmacol. Experimental Therapeutics* 296:388-395.

Yu et al. (Apr. 25, 1991). "Vitamin D Receptor Expression in Human Lymphocytes. Signal Requirements and Characterization by Western Blots and DNA Sequencing," *The Journal of Biological Chemistry* 266(12):7588-7595.

Zaug et al. "A Labile Phosphodiester Bond at the Ligation Junction in a Circular Intervening Sequence RNA," *American Association for the Advancement of Science* vol. 224, Issue: 4649, pp. 574-578, 1984.

Zellweger et al. "Antitumor Activity of Antisense Clusterin Oligonucleotides is Improved in Vitro and in Vivo by Incorporation of 2'-*O*-(2-Methoxy)Ethyl Chemistry," *J. Pharmacol. Experimental Therapeutics*, 298, pp. 934-940, 2001.

Zörnig et al. (2001). "Apoptosis regulators and their role in tumorigenesis," *Biochimica et Biophysica Acta* 1551:F1-F37.

Zur Hausen, H. (Oct. 9, 1996). "Papillomavirus infections—a major cause of human cancers," *Biochimica et Biophysica Acta* 1288:F55-F78.

International Search Report mailed on Oct. 27, 2005 for PCT Patent Application No. PCT/US04/15929 filed on May 21, 2004, 4 pages.

Written Opinion mailed on Oct. 27, 2005 for PCT Patent Application No. PCT/US04/15929 filed on May 21, 2004, 7 pages.

\* cited by examiner

MARKERS FOR PRE-CANCER AND CANCER CELLS AND THE METHOD TO INTERFERE WITH CELL PROLIFERATION THEREIN

CROSS-REFERENCE TO RELATED APPLICATIONS

This application is a divisional of U.S. patent application Ser. No. 10/557,458, filed May 22, 2006, which is a 35 U.S.C. §371 national phase application of International Patent Application No. PCT/US2004/015929, filed May 21, 2004, which, in turn, claims the benefit of U.S. Provisional Patent Application No. 60/472,106, filed May 21, 2003.

FIELD OF THE INVENTION

The invention relates to cancer therapy, cancer diagnosis and research reagents in connection with a novel family of human mitochondrial RNAs referred to as human mitochondrial chimeric RNAs. In particular, this invention relates to oligonucleotides targeted to the human mitochondrial chimeric RNAs. The oligonucleotides of the invention hybridize to the chimeric RNAs inducing cancer cell death. The composition and methods provided in the invention are useful as a new cancer therapy. In addition, the oligonucleotides can be used for diagnosis of cancer and pre-cancer cells based on the differential expression of the mitochondrial chimeric RNAs in resting and proliferating normal cell, pre-cancer and cancer cells.

BACKGROUND OF THE INVENTION

Mitochondria

Mitochondria are subcellular organelles that manufacture the essential molecule adenosine triphosphate (ATP) by oxidative phosphorylation. The human mitochondrial DNA (mtDNA) of 16,654 base pair encodes two ribosomal RNAs, 22 transfer RNAs (tRNAs) and 13 open reading frames (ORF) that encode a similar number of polypeptides (Clayton, Hum Reprod. Suppl 2:11-17, 2000; Taanman, Biochim. Biophys. Acta, 1410:103-123, 1999). On the basis of the content of G+T base composition, the two strands of the mtDNA differ in buoyant density and can be separated in denaturating cesium chloride gradients. The heavy strand or H-strand encodes the two ribosomal RNAs (12S and 16S), 14 tRNAs and 12 polypeptides corresponding to ND 1, ND 2, ND 3, ND4L, ND4, ND 5, COX I, COX II, COX III, ATP6, ATP8 and Cyt b. The light strand or L-strand codes for 8 tRNAs and the subunit of the complex NAD dehydrogenase ND6 (Clayton, Hum Reprod. Suppl 2:11-17, 2000; Taanman, Biochim. Biophys. Acta, 1410:103-123, 1999).

A large proportion of the mtDNA contains a short three-stranded structure called the displacement loop or D-loop. This region, that in humans is 1,006 base palm, is flanked by the genes for tRNA of phenylalanine (tRNA$^{Phe}$) and the tRNA of proline (tRNA$^{Pro}$) and contains a short nucleic acid strand complementary to the L-strand and displacing the H-strand (Clayton, Hum Reprod. Suppi 2:11-17, 2000; Taanman, Biochim. Biophys. Acta, 1410:103-123, 1999). This region has evolved as the major control site for mtDNA expression and contains the leading-strand or H-strand origin of replication and the major promoters for transcription of the H-(HSP) and L-strand (LSP). Despite the close proximity of the HSP and LSP (about 150 bp). these regulatory elements are functionally independent in vitro (Shuaey and Attardi, J Biol. Chem. 260:1952-1958, 1985; Taanman, Biochim. Biophys. Acta, 1410:103-123, 1999) as well as in vivo, utilizing model of patients with mitochondrial diseases (Chinnery and Tumbull, Mol. Med. Today, 6:425432, 2000).

Both strands are transcribed as polydcistronic RNAs which are then processed to release the individual mRNAs, tRNAs and the rRNAs (Taanman, Biochim. Biophys. Acta, 1410: 103-123, 1999). In humans, the mitochondrial RNA polymerase is a protein of 1,230 amino acids with significant homology with the sequence of yeast mitochondrial RNA polymerase and with the RNA polymerases of several bacteriophages (Tiranti et al., Hum Mol Genet. 6:615-625, 1997). In addition, a family of transcription factors have been characterized such as the mitochondrial transcription factor A or TFAM which is essential for mammalian mtDNA transcription and is a member of the high mobility group (HMG)-box family of DNA-binding proteins (Parisi and Clayton, Science. 252:965-969, 1991). Recently, two independent reports described the characteristics of new transcription factors, TFB1M and TFB2M, in human and mouse (McCulloch et al., Mol. Cell Biol. 22:1116-1125, 2002; Falkenberg et al., Nat Genet. 31:289-294, 2002; Rantanen at al., Mamm Genome. 14:1-6, 2003). In spite of the considerable progress achieved on the cis- and trans-acting elements involved in mtDNA transcription, the functional details are not fully understood.

Mitochondria and Apoptosis

Mitochondria play a central role in apoptosis, a fundamental biological process by which cells die in a well-controlled or programmed manner. This cell suicide program is essential during development and for adult homeostasis of all metazoan animals. Apoptosis is activated to eradicate superfluous, damaged, mutated and aged cells (Meier et al., Nature 407: 796-801, 2000). Disregulation of apoptosis is implicated in the appearance of several pathologies. Thus, abnormal inhibition of apoptosis is a hallmark of neoplasia, whereas massive apoptosis has been linked with acute diseases such as stroke, septic shock and neurodegerative disorders. At present the process of apoptosis is described as two major pathways known as the extrinsic and the intrinsic pathways (Zörnig et al., Biochim. Biophys. Acta, 1551:F1-F37, 2001). The extrinsic pathway is a process that is initiated at the cell membrane by the binding of different ligands to the death receptors (Krammer, Nature 407:789-795, 2000; Zörnig et al., Biochim. Biophys. Act, 1551:F1-f37, 2001).

Caspases, are responsible for the proteolytic cascade in apoptosis. Caspases are synthesized as inactive precursor proteins that undergo proteolytic maturation or processing upon apoptosis induction (Zörnig et al., Biochim. Biophys. Acts, 1551:F1-F37, 2001). However, more recently several experimental evidences indicate that lysosomal proteases constitute an alternative pathway of proteolysis after apoptotic insults (Guicciardi et al., Oncogene, 23:2881-2890, 2004).

On the other hand, anti-apoptotic proteins homologous to the human oncoprotein Bcl-2 have been described. This protein belongs to a family of proteins that are either anti-apoptotic (Bcl-2, Bcl-XL, Bcl-w) or pro-apoptotic (Bax, Bak, Bim, Bid, etc.) (Zörnig et al., Biochim. Biophys. Acts, 1551: F1-F37, 2001).

Mitochondria are particularly affected early during the apoptotic process and at present time they are recognized as the central coordinators of cell death (Boya et al., Biochem. Biophys. Res. Commun. 304:575-581, 2003; Ferri and Kroemer, Nature Cell Biol. 3:E255-E263, 2001; Zörnig et al., Biochim. Biophys. Acta, 1551:F1-F37, 2001). Several pro-apoptotic signal and damage pathways converge on mitochondria to induce mitochondrial membrane permeabilization, phenomenon that is under the control of Bcl-2 proteins (Boya et al., Biochem. Biophys. Res. Commun. 304:575-581, 2003; Zörnig et al., Biochim. Biophys. Acta, 1551:F1-F37, 2001). After cells receive apoptotic insults, the trans-membrane potential ($\Delta\psi_m$) dissipates resulting in the complete permeabilization of the outer mitochondrial membrane and the consequent leakage of toxic mitochondrial intermembrane proteins. The first example of the leakage of a mitochondrial protein was the liberation of cytochrome c (Liu at al., Apoptosis, 6:453-462, 2001). When cytochrome c is present in the cytosol, it drives the assembly of the caspase activating complex termed the apoptosome. Cytochrome c binds to Apaf-1 (apoptotic protease activatin factor-1) facilitating the binding of dATP/ATP to the complex and the oligomerization of Apaf-1 (Adrain at al., 1999; Benedict et al., 2000). Oligomerlzation of Apaf-1 allows the recruitment of pro-caspase-9 which catalyzes the proteolytic activation of the precursor and generation of active caspase-9 (Adrain et al., J. Biol. Chem. 274:20855-20860, 1999; Benedict et al., J. Biol. Chem., 275:8461-8468, 2000).

A family of cytosolic inhibitor of apoptosis proteins have been described and are known as XIAP, c-IAP1 and c-IAP2. These proteins bind to and inhibit processed caspase-3 and caspase-9 and consequently stop the cascade of degradation. However, the cell also contains countermine mechanisms to bypass this anti-apoptotic pathway. In cells undergoing apoptosis, caspases are liberated of this inhibitory effect by binding to IAPs of a protein known as Smac (Second Mitochondrial Activator of Caspases) or DIABLO (Direct IAP Binding protein with Low pI) (Verhagen et al., Apoptosis, 7:163-166, 2002). By binding to IAPs, Smac/DIABLO displace active caspases from IAPs and thus promote cell death. Another protein, knowns as HtrA2, is released from the mitochondria into the cytosol after apoptotic insult where the protein binds to IAPs in a similar fashion as does Smac/DIABLO and thereby facilitating caspases activation (Verhagen et al., Apoptosis. 7:163-168, 2002; Martins et al., 2001; Suzuki et al., Mol. Cell, 8:613-621, 2001; Hedge et al., Apoptosis, 7:123-132, 2002).

The apoptosis inducing factor (AIF) is another component of the apoptotic cascade. After induction of apoptosis, AIF translocates to the cytosol and to the nucleus. In the nucleus, AIF induces peripheral chromatin condensation and DNA fragmentation. AIF also induces several hallmarks of apoptosis like $\Delta\psi_m$ dissipation and phosphatidylserine exposure (Zörnig et al., Biochim. Biophys. Acta, 1551:F1-F37, 2001). A factor that seems to regulate the apoptotic activity of AIF is the heat schock protein 70 (Ravagnan et al., Nature Cell Biol. 3:839-843, 2001). Another mitochondrial factor that exits the mitochondria and translocates into the nucleus like AIF is endonuclease G or Endo G. In the nucleus, Endo G generates DNA fragmentation even in the presence of caspase inhibitors (U et al., Nature, 412:95-99, 2001). Endo G may act in similar fashion as CAD (caspase-activated DNAse), a nuclease whose activation critically relies on caspases (Samejima et al., J. Biol. Chem., 278:45427-45432, 2001).

Cancer and Pre-Cancer

Cancer is a cellular malignancy whose unique trait, loss of normal control of cell cycle, results in unregulated growth, lack of differentiation, and ability to invade other tissues and metastasize. Carcinogenesis is the process by which a normal cell is transformed in a malignant cell. Carcinogenesis is a multiple step process beginning with the genetic event of initiation followed by selective expansion of altered cells during promotion to form early adenomas. In the absence of continuous promotion, the adenoma regresses and disappears. With a second genetic event, a small number of promoted adenomas progress to form late adenomas some of which may then undergo malignant conversion (McKinnell et al., "The Biology Basis of Cancer", Ch. 3, 1998).

The etiology of cancer is complex and includes alteration of the cell cycle regulation, chromosomal abnormalities and chromosomes breakage. Infectious agents such several types of oncogenic viruses, chemicals, radiation (ultraviolet or ionizing radiation) and immunological disorders are thought to be the major causes of carcinogenesis (McKinnell et al., The Biological Basis of Cancer, Ch. 3, 1998).

It has been proposed for a long time that cancer is also related to mitochondrial dysfunction. One of these theories suggests that mitochondrial mutation might be the primary cause of cell transformation and cancer (Warburg, 1956; Carew and Huang, Mol. Cancer, 1:1-12, 2002). Alterations of the mitochondrial DNA (mtDNA) was reported in hematologic malignancies (Clayton and Vinograd, Nature. 216:652-657, 1967) and in breast cancer (Tan et al., 2002; Parrella et al., 2001). Mutations of several regions of the mtDNA and deletions have been also identified in patients with colorectal cancer, prostate cancer, ovarian cancer, gastric cancer, pancreatic cancer, hepatocellular carcinoma, esophageal cancer, kidney cancer, thyroid cancer and brain tumors (reviewed by Carew and Huang, Mol. Cancer, 1:1-12, 2002). In general, there appears to be two major features of mtDNA alterations in cancer irrespective of tumor type. The majority of the mutations are base transitions from T to C and G to A. Second, while there is diversity in the particular genes in which mutations occur, the D-loop seems to be the most frequent somatic mutated region of the mtDNA in most tumor types.

Pre-cancer cells are defined here as a transformed cell which can evolve or differentiate into a malignant cell. Some examples are cells transformed by DNA or RNA oncoviruses.

The present invention is related to a novel family of mitochondrial RNAs and the use herein of these RNAs as targets for diagnostics and cancer therapy. The present invention provides compositions and methods and that are useful to differentiate normal cells from tumor cells, or from pre-malignant cells or cells transformed with oncogenic viruses. In particular, as elaborated below, the present invention provides composition and methods for diagnostic assays to differentiate normal cells from pre-cancer and cancer cells. In another embodiment of the invention, composition and methods are provided to induce massive and selective tumor cell death. Therefore, the present invention provides compositions and methods which may be used in cancer and pre-cancer diagnostic and therapy as well as for research.

SUMMARY OF THE INVENTION

The present invention is directed to compositions and methods useful for detecting a family of novel human mitochondrial RNAs, referred to as mitochondrial chimeric RNAs, that are expressed differentially in normal resting and proliferating cells, pre-cancer and cancer cells.

Sense Mitochondrial Chimeric RNAs

In one aspect of this invention compositions and methods are provided to detect a mitochondrial chimeric RNA comprised of an inverted repeat of 815 nucleotides joined covalently to the 5' end of the 16S mitochondrial ribosomal RNA (SEQ ID NO 1). The inverted repeat corresponds to a fragment of 815 nucleotides of the RNA transcribed from the L-strand of the 16S gone of the mtDNA. Thus, the synthesis of this novel RNA requires the transcription of the L-strand and the H-strand of the 16S gene of the mtDNA. Since transcription of both strands of the mtDNA are regulated by different promoters, we refer to this novel RNA in the present invention as the mitochondrial chimeric RNA (SEQ ID NO 1). In addition, since the inverted repeat of 815 nucleotides is joined to the "sense" 16S RNA (transcribed from the H-strand) we refer to this novel RNA as the "sense mitochondrial chimeric RNA"

This invention provides methods and compositions to detect the expression of the sense mitochondrial chimeric RNA in cultured cells, in cell samples, and in tissue sections. The detection can be carried out by in situ hybridization, synthesis of the corresponding cDNA and amplification by PCR, transcription mediated amplification (TMA) (Comanor et al., J. Clin Virol., 28:14-26, 2003) or Northern blot, or other methods obvious to one skilled in the art.

In one aspect of this invention, in situ hybridization assays revealed that the sense mitochondrial chimeric RNA is expressed in normal proliferating cells, in tumor cells in culture as well as in tumor cells present in human biopsies of different tumor types. The sense mitochondrial chimeric RNA is not expressed in normal resting cells. In yet another embodiment of the invention, methods and compositions are provided to detect a second novel sense mitochondrial chimeric RNA in cells transformed with papilloma virus 16 or 18 (Hausen, Biochim. Biophys. Acta, 1288:F55-F78, 1996). In these transformed cells, a new sense mitochondrial chimeric RNA comprising of an inverted repeat of 754 nucleotides joined covalently to the 5' end of the 16S mitochondrial RNA is expressed (SEQ ID NO 2). This RNA is not present in normal proliferating cells or in tumor cells. The methods and compositions also demonstrated that a third sense mitochondrial chimeric RNA, comprising an inverted repeat of 694 nucleotides joined covalently to the 5' end of the 16S mitochondrial RNA (SEQ ID NO 3), is present in cells transformed with HTLV-1.

Antisense Mitochondrial Chimeric RNA

This invention also provides methods and compositions that revealed that normal proliferating cells over express an antisense mitochondrial chimeric RNAs corresponding to SEQ ID NO 4, SEQ ID NO 5, SEQ ID NO 6. These transcripts contain inverted repeats of variable length (transcribed from the H-strand) joined to the 5' end of the antisense 16S mitochondrial ribosomal RNA (transcribed from the L-strand), hence the name of antisense mitochondrial chimeric RNA. The expression of the antisense mitochondrial chimeric RNA is down regulated in tumor cell lines in culture as well as in tumor cells present in human biopsies of different types of tumors as well as in transformed or pre-cancer cells. Accordingly, the present invention provides methods and composition to detect the expression of the sense and the antisense mitochondrial chimeric RNAs, distinguishing normal proliferating cells from cancer and pre-cancer cells and therefore provides a novel marker for malignant cells and cancer.

Cancer Therapy

In another aspect of this invention, methods and compositions are provided to interfere with the sense and antisense mitochondrial chimeric RNAs. One preferred embodiment is to interfere with the antisense mitochondrial chimeric RNA in tumor cells which contains low copy number of this transcript. The interference is carried out with oligonucleotides or oligonucleotide analogs, whose sequences are complementary to the sequences of the antisense mitochondrial chimeric RNA (SEQ ID NO 4 and/or SEQ ID NO 5 and/or SEQ ID NO 6). Treatment of tumor cells of different types with one or more of these complementary oligonucleotides induces cell death or apoptosis. The oligonucleotides are compounds of 15 to 50 nucleotides where at least 15 nucleobases are complementary to SEQ ID NO 4 and/or SEQ ID NO 5 and/or SEQ ID NO 6. Examples of these complementary oligonucleotides are shown in SEQ ID NOS 9 to 98. The induction of apoptosis is selective since treatment of human lymphocytes (normal resting cell) or human lymphocytes stimulated with phytohaemagglutinin (normal proliferating cells) do not undergo apoptosis after treatment with oligonucleotides complementary to the sequences of the antisense mitochondrial chimeric RNA under the same conditions. If the tumor cells are treated with oligonucleotides targeted or complementary to the sense mitochondrial chimeric RNA (SEQ ID NO I and/or SEQ ID NO 2 and/or SEQ ID NO 3) a diminished induction of cell death or apoptosis is obtained.

DETAILED DESCRIPTION OF THE INVENTION

The Human Mitochondrial Chimeric RNA Family

The present invention is based on the surprising discovery that human cells express a family of novel mitochondrial RNAs, referred to as the human mitochondrial chimeric RNAs.

One of these transcripts contains a long inverted repeat of 815 nucleotides covalently joined to the 5' end of the mitochondrial 16S ribosomal RNA, named sense mitochondrial chimeric RNA. The long inverted repeat is fully complementary to the 16S ribosomal RNA from positions 51 to 866, forming a long double stranded stem and a loop of 50 nucleotides. As shown in FIG. 1A, the stem of 815 base pairs represents a significant problem for any reverse transcriptase to synthesize the corresponding cDNA. Therefore a new strategy was used to amplify this RNA by RT-PCR which is illustrated in FIG. 1A. After obtaining the sequence of each overlapping fragment, they were assembled as contigs to obtain the complete sequence of the sense mitochondrial chimeric RNA shown in SEQ ID No 1 (FIG. 1A).

Other aspect of this invention is the discovery of other novel sense mitochondrial chimeric RNAs which are expressed in cells transformed with the oncogenic human papilloma virus 16 or 18. Human foreskin keratinocytes (HFK) where infected with HPV 16 or 18 (Hausen, Biochim. Biophys. Acts, 1288:F55-F78, 1996). The infection induces transformation or immortalization of the HFK. However, these cells are not tumorigenic such as the related SiHa cells (infected with HPV 16) or HeLa cells (infected with HPV 18). These cells express the sense mitochondrial chimeric RNA (SEQ ID NO 1) similar to SiHa and HeLa cells. However, the transformed cells also express another second sense mitochondrial chimeric RNA which contains an inverted repeat of 754 nucleotides joined to the 16S ribosomal RNA (FIG. 18) (SEQ ID No 2). This new sense mitochondrial chimeric RNA is down regulated or is not expressed in normal human cells (HFK) or in tumorigenic cells (SiHa or HeLa cells).

In another embodiment of this invention we determined the expression of a third sense mitochondrial chimeric RNA in cells transformed with HTLV-1 (Kobayashi at al., EMBO J., 3:1339-1343, 1984). MT-2 cells infected with HTLV-1 express the sense mitochondrial chimeric RNA (SEQ ID NO 1) and the sense mitochondrial chimeric RNA expressed in cells transformed with HPV 16 or 18 (SEQ ID NO 2). Besides these transcripts, the cell infected with HTLV-1 express a third sense mitochondrial chimeric RNA containing an inverted repeat of 694 nucleotides joined to the 5' end of the 16S ribosomal RNA. This novel RNA (FIG. 1C) (SEQ ID NO 3) is not expressed in normal proliferating cells, in tumor cells or in HFK transformed with HPV 16 or 18.

Figure 6:
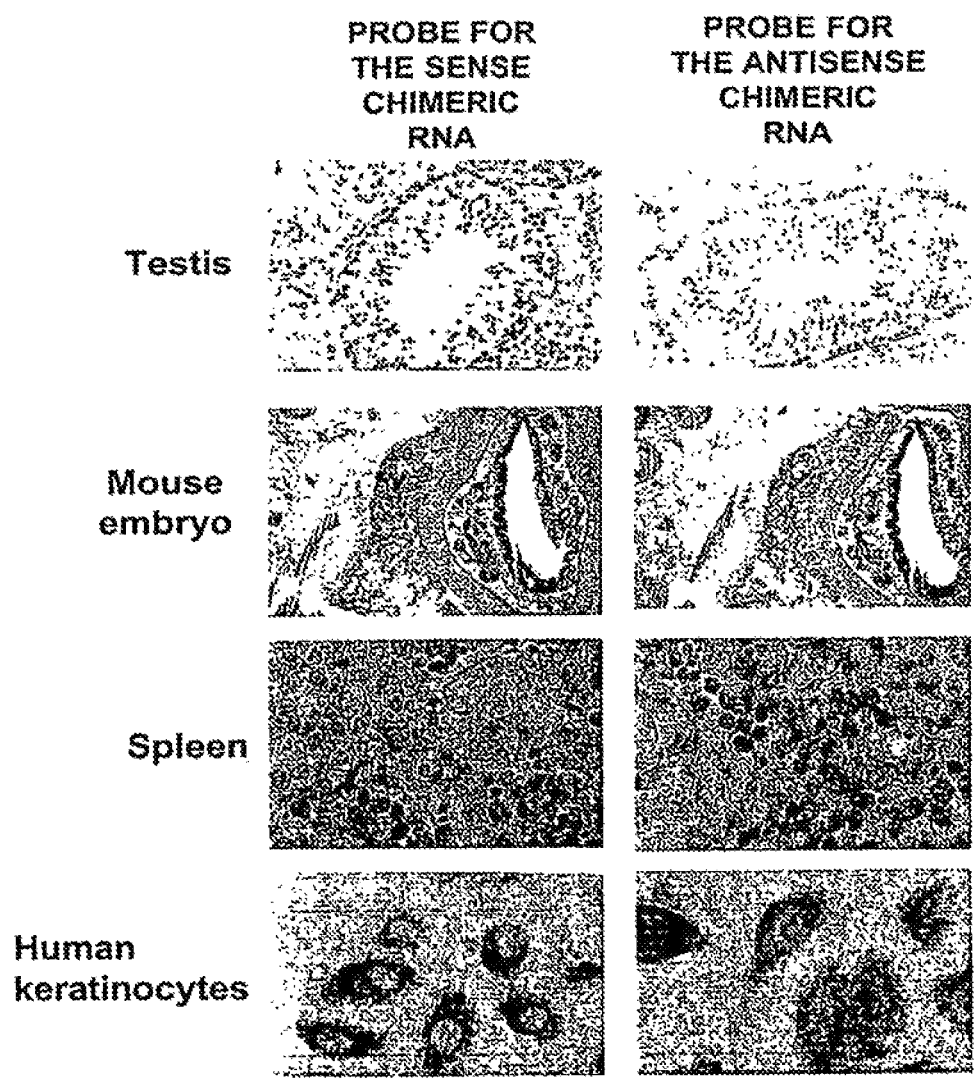
FIG. 6 in situ hybridization of normal proliferating cells. The samples were hybridized with probes targeted to the sense or the antisense mitochondrial chimeric RNA and labeled with digoxigenin. Strong hybridization signal was obtained with both probes, one complementary to the sense mitochondrial chimeric RNA (left panels) as well as to the antisense mitochondrial chimeric RNA (right panels). The tissues or cells are identified at the left.
Figure 7:
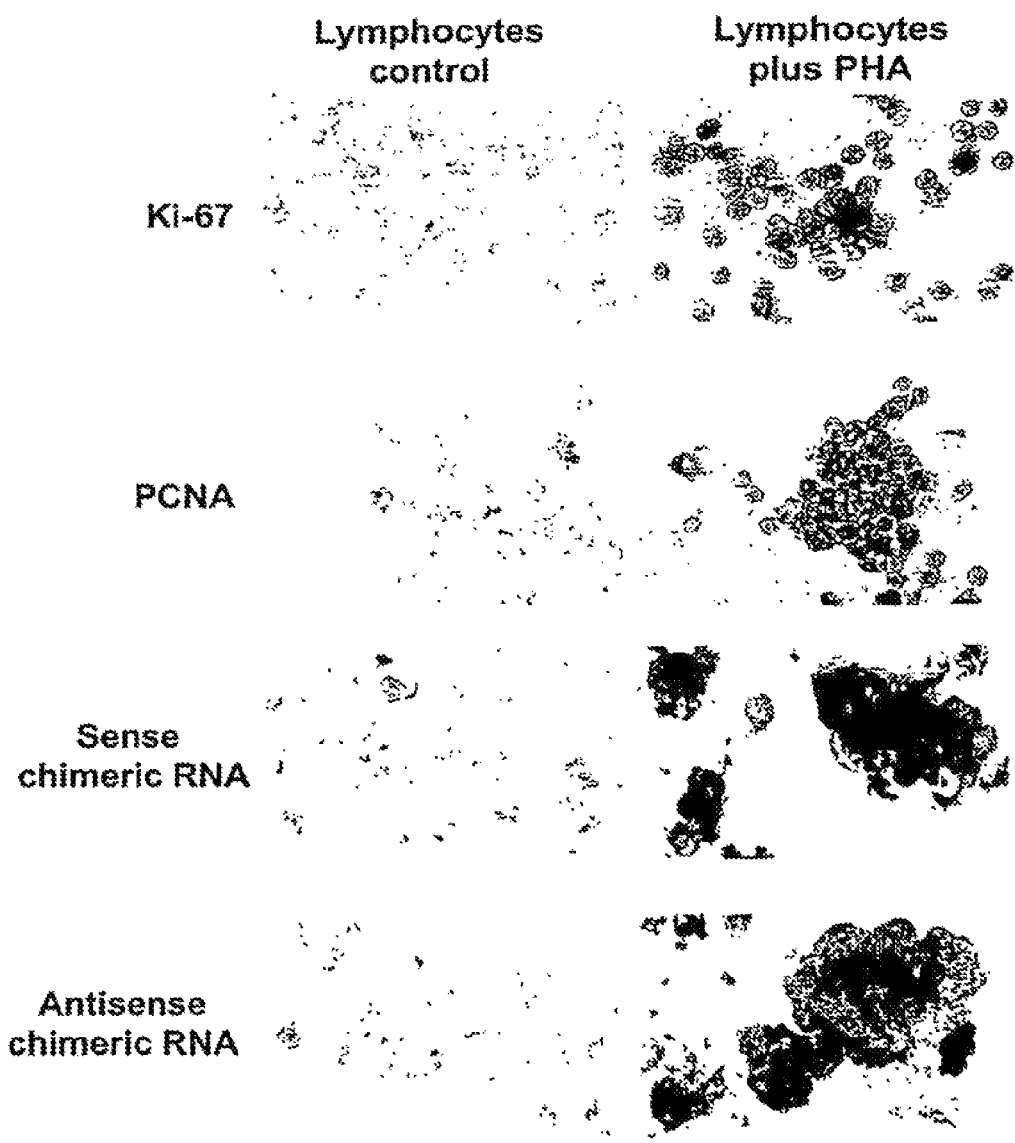
FIG. 7. Immunocytochemistry and in situ hybridization to show expression changes in human lymphocytes stimulated to proliferate with the mitogen PHA. After 48 h of stimulation with PHA, the lymphocytes express the antigens Ki-67 and PCNA (right panels). These antigens are not expressed in the control or resting lymphocytes (left panels). The in situ hybridization was carried out with oligonucleotide probes targeted to the sense and the antisense mitochondrial chimeric RNA and labeled with digoxigenin. The stimulated lymphocytes over express the sense as well as the antisense mitochondrial chimeric RNA (right panels).

Normal proliferating cells such as human foreskin keratinocytes (HFK) as described in previous section also over express the sense mitochondrial chimeric RNA (FIG. 6) (SEQ ID No 1). Human lymphocytes stimulated with mitogens such as phytohaemaggiutlnin (PHA) enter into the S phase of the cell cycle and begin the synthesis of DNA (Yu et al., J. Biol. Chem., 2668:7588-7595, 1991). As proliferating cells, the lymphocytes also express antigens related to proliferation such as Ki-67 and proliferating cell nuclear antigen or PCNA (Bantis at al., Cytopathology, 15:25-31, 2004). The stimulated lymphocytes also over express the sense mitochondrial chimeric RNA (SEQ ID No 1). Other proliferating cells such as lymphocytes in the germinal center of the spleen, spermatogonia, and embryonic cells also over express the sense mitochondrial chimeric RNA (SEQ ID NO 1) (FIG. 4). In contrast, non-proliferating cells such as non-stimulated lymphocytes, or muscle cells do not express the sense mitochondrial chimeric RNA (FIG. 7).

In another embodiment of the invention, methods to differentiate a normal proliferating cells from a tumor cell are provided. As described before, tumor and normal proliferating cells over express the sense mitochondrial chimeric RNA described in SEQ ID No 1. In addition, in specific situations of infection with HPV and HTLV-1, additional chimeric RNA are found (SEQ ID NO 2 and SEQ ID NO 3). However, the present invention is also based on the surprising discovery that normal proliferating cells also over express an antisense mitochondrial chimeric RNA. The expression of the antisense mitochondrial chimeric RNA was confirmed in human lymphocytes stimulated with PHA (FIG. 7), in normal HFK and in other normal proliferating cells (FIG. 6). Another surprising discovery of the present invention is that different to normal proliferating cells, tumor cells do not express the antisense mitochondrial chimeric RNA or markedly down regulated the production (compare FIG. 4 with FIG. 6 and FIG. 7).

Figure 3:
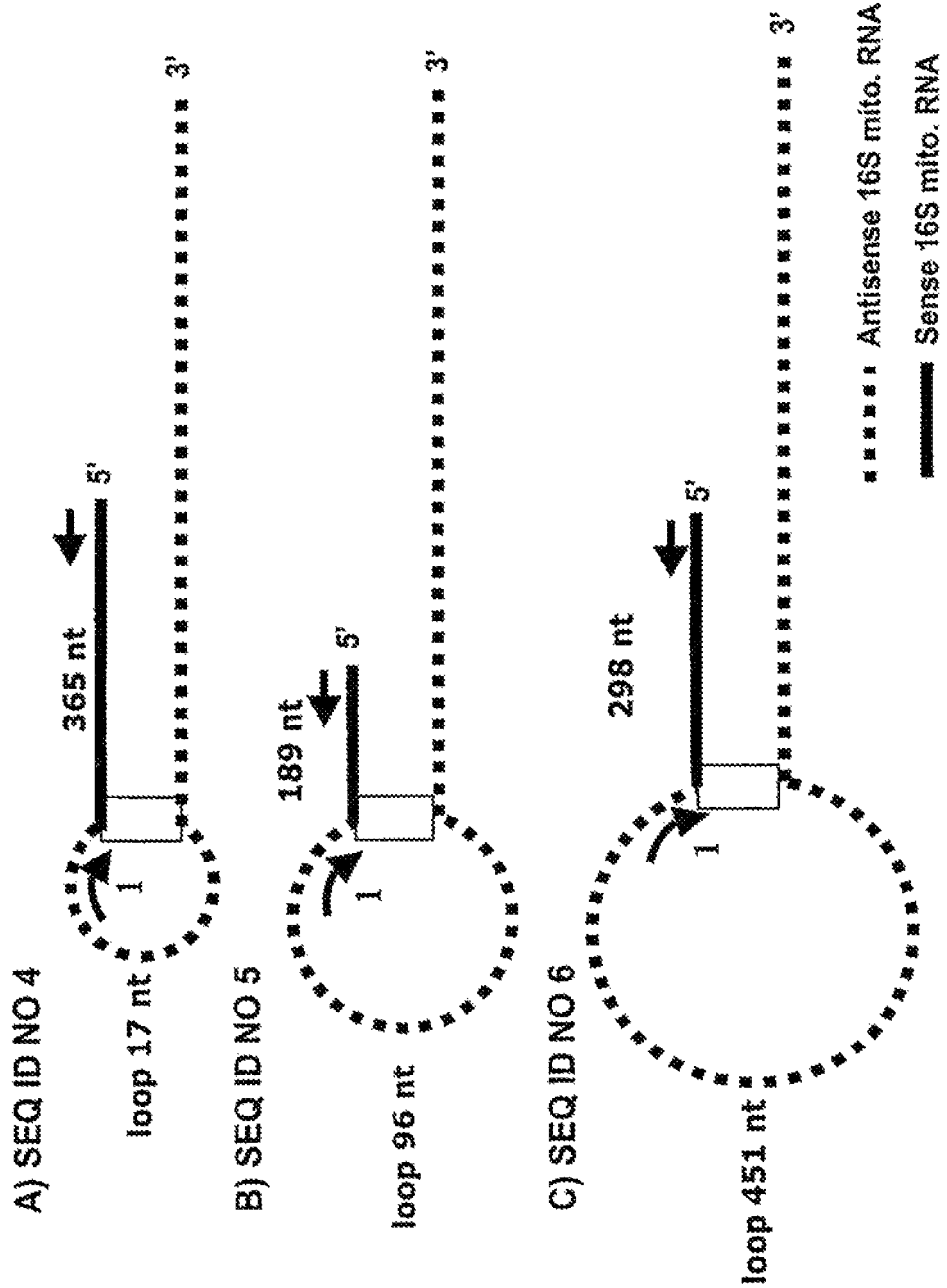
FIG. 3. Line drawings showing the structure of the antisense mitochondrial chimeric RNAs corresponding to SEQ ID NO 4, SEQ ID NO 5 and SEQ ID NO 6. The arrows represent the primer used for amplification, and primer 1 is positioned close to the 5' end of the antisense 16S mitochondrial RNA. The strategy to obtain the sequence of these transcripts is similar to that described in FIG. 1.

Using the same strategy to amplify by RT-PCR the chimeric RNA based in overlapping fragments described earlier, the structure of the antisense mitochondrial chimeric RNA was determined (FIG. 3). The sequencing and assembling in contigs reveals a complex family of antisense mitochondrial chimeric RNAs containing inverted repeat of different lengths joined to the 5' end of the antisense 16S mitochondrial ribosomal RNA (FIGS. 3A, B and C) (SEQ ID No 4, SEQ ID No 5, SEQ ID No 6). The sequence also reveals the formation of double stranded structures or stems in these RNA and the formation of loops with 17, 96 and 451 nucleotides, respectively (FIGS. 3A, B and C, SEQ ID No 4, SEQ ID No 5, SEQ ID No 6).

In other embodiment of the invention, methods and compositions are provided to follow the oncogenic transformation of cells by an oncogenic virus. HeLa cells (infected with HPV 18) or SiHa cells (infected with HPV 16) over express the sense mitochondrial chimeric RNA but down regulate the expression of the antisense mitochondrial chimeric RNAs. On the other hand, HFK as normal proliferating cells, over express both the sense as well as the antisense mitochondrial chimeric RNAs. After transformation of HFK with HPV 16 or HPV 18, the cells acquire the tumor phenotype: they over express the sense mitochondrial chimeric RNA and down regulate the expression of the antisense mitochondrial chimeric RNA. The over expression of the sense mitochondrial chimeric RNA and down regulation of the antisense mitochondrial chimeric RNA can be determined by in situ hybridization, amplification of the RNA by RT-PCR or by using other methods to determine a RNA by ways well known to the person skilled in the art. These methods and compositions can be used also to determine the change in the expression of the chimeric RNA family in cells transformed with other oncogenic virus or by compounds that induce transformations or carcinogenesis (McKinnell et al., "The biological basis of Cancer, Cambridge University Press 1998).

Cancer and Pre-Cancer Diagnostics.

According to the present invention methods and compositions are provided to detect in a biological sample the presence of the sense mitochondrial chimeric RNAs and the antisense mitochondrial chimeric RNAs. In one preferred embodiment, the detection is carried out by in situ hybridization. The detection of the sense mitochondrial chimeric RNA and the antisense mitochondrial chimeric RNAs in the cells of the biological sample indicates that the cells are normal proliferating cells. In another embodiment, the result of the in situ hybridization with tumor cells will show expression of the sense mitochondrial chimeric RNA and down regulation or absence of the antisense mitochondrial chimeric RNA. If the biological sample contains non-proliferating normal cells the in situ hybridization will show that neither the sense mitochondrial chimeric RNA nor the antisense mitochondrial chimeric RNA are expressed.

Biological samples are understood as normal cells (resting or proliferating cells) in culture or in blood smears or bone marrow smears, tumor cells in culture and normal cells transformed with oncogenic virus. Additionally, biological samples comprise cells obtained from the urine or the bladder washing from patients suspecting of having bladder or kidney cancer, or cells from saliva in patients suspecting of having head and neck cancers, or cells from bronchioalveolar lavage from patients suspecting of having lung cancer. Also, biological samples comprise cells smears from the blood of patients suspecting of having leukemia or cell smears from blood or lymph, lymph node of patients suspecting of having metastasis.

The biological samples according to the invention include the use of rapidly frozen tissue or cells samples for histopathological analysis, art well know by artisans in the field. Alternatively, the biological sample can be biopsies of sections fixed by using chemical treatment that can be accomplished by the wide variety of fixation protocols known in the art (Frederick et al, Current Protocols in Molecular Biology, Volume 2, Unit 14, Frederick M. Ausubul et al. edS., 1995; Cells, Cell Biology, A Laboratory Handbook, Julio E. Cells, ed., 1994). The biological samples can also be non-fixed biological materials that are not been chemically modified or treated with formalin or other fixative well known in the art.

Alternatively, the in situ hybridization can be carried out by using biological samples embedded in materials such as paraffin or other embedding polymers. The blocks obtained after embedding can be sectioned with a microtome in section of about 4 to about 10 μm of thickness. The section can then be applied to glass or plastic slides coated with an adhesive substance know in the art such as polylysine or mussel adhesive protein (Burdo et al., Curr. Opin. Biotechnol., 8:309.312, 1997).

The in situ hybridization of the present invention can be carried out in ways well known to persons skilled in the art. For example, a hybridization solution comprising one or more labeled probes targeted to one or more of the sequences of sense mitochondrial chimeric RNA (SEQ ID NO 1, SEQ ID NO 2, SEQ ID NO 3) or antisense mitochondrial chimeric RNA (SEQ ID NO 4, SEQ ID NO 5, SEQ ID NO 6) within the cell, is contacted with the cell under hybridization conditions. The hybridization signal is then compared with a predetermined hybridization pattern from normal or control cancer and pre-cancer cells.

As used herein, the labeled probes to carry out the in situ hybridization are RNA, DNA or synthetic nucleic acids that can be prepared by any method known in the art. Synthetic nucleic acids include riboprobes transcribed in vitro or PCR fragments. In a preferred embodiment of this invention, synthetic complementary oligonucleotides can be used. The complementary oligonucleotide probes are at least about 10 nucleotides in length, most preferably at least about 14, and most preferably at least 18 nucleotides in length. The skilled artisan understand that the length can extend from 10 nucleotides or more to any length which still allows hybridization to the sense mitochondrial chimeric RNAs or the antisense mitochondrial chimeric RNAs. In a preferred embodiment herein, the length is about 30 nucleotides, more preferably about 25 nucleotides, and most preferably between 10 to 50 nucleotides in length. Longer probing nucleic acids may also be used. The sequences of the probe is at least ninety five percent homologous to the sequences listed in SEQ ID No 1, SEQ ID No 2, SEQ ID No 3. SEQ ID No 4, SEQ ID No 5 and SEQ ID No 6.

The complementary oligonucleotide probes of the present invention will generally contain phosphodiester bonds, although in some cases, oligonucleotides probe analogs are included that may have alternate inter nucleoside linkages, comprising, but not limited to, phosphorothioate (Meg et al., Nucleic Acids Res. 19:1437-1441, 1991; and U.S. Pat. No. 5,644,048), peptide nucleic acid or PNA (Eghoim, Nature, 365:586-568, 1993; and U.S. Pat. No. 6,658,687), phosphoramide (Beaucage, Methods Mol. Biol. 20:33-61, 1993), phosphorodithloate (Capaldi et al., Nucleic Acids Res., 28:E40, 2000). Other complementary oligonucleotides analogs include such as, but not limited to, morphollno (Summerton, Biochim. Biophys. Acts. 1489:141-158, 1999), locked oligonucleotides (Wahlestedt et al., Proc. Natl. Acad. Sci. US, 97:5633-5638, 2000), peptidlc nucleic acids or PNA (Nielsen at al., 1993; Hyrup and Nielsen, 1996) or 2-o-(2-methoxy) ethyl modified 5' and 3' end oligornucleotides (McKay at al., J. Biol. Chem., 274:1715-1722, 1999). All of these references are hereby expressly incorporated by reference. The nucleic add may contain any combination of deoxyribo- and ribonucleotides, and any combination of bases, including uracil, adenine, thymine, cytosine, guanine, inosine, xathanine hypoxathanine, isocytosine, isoguanine, etc.

In another embodiment of the invention, the nucleic acid or oligonucleotide probes have to be labeled to detect the hybridization with the sense mitochondrial chimeric RNAs or the antisense mitochondrial chimeric RNAs. The probes may be labeled with a detectable marker by any method known in the art. Methods for labelling probes include random priming, end labeling, PCR and nick translation. Enzymatic labeling is conducted in the presence of nucleic acid polymerase, three unlabeled nucleotides, and a fourth nucleotide which is either directly labeled, contains a linker arm for attaching a label, or is attached to a hapten or other molecule to which a labeled binding molecule may bind. Suitable direct labels include radioactive labels such as $^{32}P$, $^{3}H$, and $^{35}S$ and non-radioactive labels such as fluorescent markers. Preferred fluorochromes (fluorophores) include 5(6)-carboxyfluorescein, 6-((7-amino-4-methylcoumarin-3-acetyl)amino)hexanoic acid, 5(and 6)-carboxy-X-rhodamine, Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights. Ill.) or the Alexa dyes comprising Alexa 488, Alexa 532, Alexa 556, Alexa 590, etc. (Molecular Probes, Eugene, Oreg.).

Probes may be indirectly labeled by incorporating a nucleotide covalently linked to a hapten or other molecule. Preferred haptens, but not limited to, include 5(6)-carboxyfluorescein, 2,4-dinitrophenyl, digoxigenin and biotin, and performing the detection of the probe with a labeled antibody directed to that hapten or other molecule. In the case of biotin, detection can be carry out with avidin or streptavidin conjugated to a detectable label. Antibodies, streptavidin and avidin may be conjugated with a fluorescent marker, or with an enzymatic marker such as alkaline phosphatase or horseradish peroxidase to render them detectable. Conjugated streptavidin, avidin and antibodies anti-digoxigenin are commercially available from companies such as Vector Laboratories (Burtlingame, Calif.) and Boehringer Mannheim (Indianapolis, Ind.). In another embodiment, the antibodies or streptavidin can be conjugated to quantum dot with superior and more stable fluorescence emission (Wu et al., Nature Biotechnol. 21:41-46, 2003).

The enzyme in the conjugated of antibodies and streptavidin can be detected through a calorimetric reaction by providing a substrate for the enzyme. In the presence of various substrates, different colors are produced by the reaction, and these colors can be visualized to separately detect multiple probes. Any substrate known in the art may be used. Preferred substrates for alkaline phosphatese include 5-bromo-4-chloro-3-indolylphosphate (BCIP) and nitro blue tetrazolium (NBT). The preferred substrate for horseradish peroxidase is diaminobenzoate (DAB). Those skilled in the art understand that other enzymatic activities also con be used.

In another embodiment of the present invention, the conditions to carry out in situ hybridization to achieve accurate and reproducible results are described. Those of ordinary skill in the art of nucleic acid hybridization will recognize that factors commonly used to control the stringency of hybridization include formamide concentration or other chemical denaturant reagent, salt concentration or variable ionic strength, hybridization temperature, detergent concentration, pH and the presence or absence of chaotropic agents. These stringency factors can be modulated to thereby control the stringency of hybridization of the oligonucleotide probes for the chimeric RNA. Optimal stringency for an assay may be experimentally determined by examination of each stringency factor until the desired degree of discrimination is achieved.

Other conditions that have to be controlled for optimal in situ hybridization are for example the use of chemical agent to block non-specific binding of the probe to components present in the biological samples others than the target chimeric RNAs. The blocking agent, but not limited to, are RNA, DNA or oligonucleotides without a label. The blocking agent incorporated in the hybridization solution will suppress the non-specific binding of the labeled probe, and hence, increase the signal to noise ratio of the assay. In yet another aspect of the invention, the probe has a sequence complementary to the sequence of the sense or antisense mitochondrial chimeric RNAs (see SEQ ID No 1, SEQ ID No 2, SEQ ID No 3, SEQ ID No 4, SEQ ID No 5 and SEQ ID No 6).

Fixation of the biological sequence is also an important aspect of in situ hybridization that has to be determined experimentally. Highly cross-linking fixative such as glutaraldehyde is not recommended since it may block the access of the probe to the target sense mitochondrial chimeric RNA or antisense mitochondrial chimeric RNA. The preferred method of this invention is to fix the biological sample with formalin, although frozen samples are also preferred. To expose the sense mitochondrial chimeric RNAs or the antisense mitochondrial chimeric RNA to the labeled probe, additional procedures can be used. For example, the biological sample can be digested with proteinase K to remove proteins that can block the access of the probe to the target chimeric RNAs. Treatment of biological samples with proteinase K or other proteases previous to in situ hybridization are well known for those artisans in the art.

As described before, the presence of long inverted repeats in the chimeric RNA and in the antisense chimeric RNAs, induce the formation of highly stable double stranded structures. These structures together with the secondary structures of the single strand region of the chimeric RNAs may constitute barriers for the access of the probe to the target chimeric RNAs. Therefore, in another aspect of the invention, the biological sample is treated with 0.2 M HCl for 10 min at room temperature to denature the chimeric RNA. Then the sample is rapidly neutralized by several washes with a buffer solution at pH 7.4 before applying the in situ hybridization protocol described herein. Aided by no more than routine experimentation and the disclosure provided herein, those of skilled in the art will easily be able to determine suitable hybridization conditions for performing assays utilizing the methods and compositions described herein. Suitable in-situ hybridization conditions are those conditions suitable for performing an in-situ hybridization procedure. Thus, suitable in-situ hybridization conditions will become apparent using the disclosure and references herein; with or without additional routine experimentation.

In another embodiment of the present invention, the localization of the sense mitochondrial chimeric RNAs as determined by in situ hybridization may have important information for prognosis and management of the patient with cancer. In tumor cells, the sense mitochondrial chimeric RNA is found mostly in the cytoplasm in close association with late endosomes/lysosomes. However, localization in the nucleolus is also found in certain cells. In tumor cells present in human biopsies, the hybridization signal reveals that the sense mitochondrial chimeric RNA is in the cytoplasm only, or in the cytoplasm and the nucleolus or in the cytoplasm and the nucleus. Therefore the different localizations may have an important prognostic value. In a preferred embodiment, panel of human biopsies, for example from breast, colorectal or prostate tumors, may be studied by in situ hybridization to detect the chimeric RNA. Together with the positive hybridization signal (independent on how the probe was labeled), the intracellular localization (only cytoplasm, cytoplasm and nucleus or cytoplasm and nucleolus) should be established in each tumor and the results compared with the survival of each patient.

In another aspect of this invention, mixture of individual cells containing normal and/or tumor cells can be subjected to hybridization in suspension with oligonucleotide probes labeled with fluorochromes and complementary to the sense mitochondrial chimeric RNA and to the antisense mitochondrial chimeric RNA. For example the probe or probes targeted to the sense mitochondrial chimeric RNA can be labeled with rhodamin, and the probe or probes targeted to the antisense mitochondrial chimeric RNA can be labeled with Alexa 488. After hybridization and washing under the conditions described before, the cells can be analyzed by intracellular labeling flow cytometry.

The preferred embodiment of the invention is to use in situ hybridization since the information obtained about the specific localization of the chimeric RNA in the tumor cell provides important additional information of prognosis.

In yet another embodiment of the invention, alternative molecular methods can be used to detect the expression of the chimeric RNA and differential expression of the sense and antisense chimeric RNA in normal, pre-cancer and cancer cells. These alternative methods include, but are not limited to, Northern blot, dot blot, oligonucleotide arrays for the chimeric RNA and the antisense chimeric RNAs, amplification of the RNA by RT-PCR, amplification of the RNA by in vitro transcription mediated amplification or TMA, S1 or ribonuclease protection assays, etc.

Figure 1:
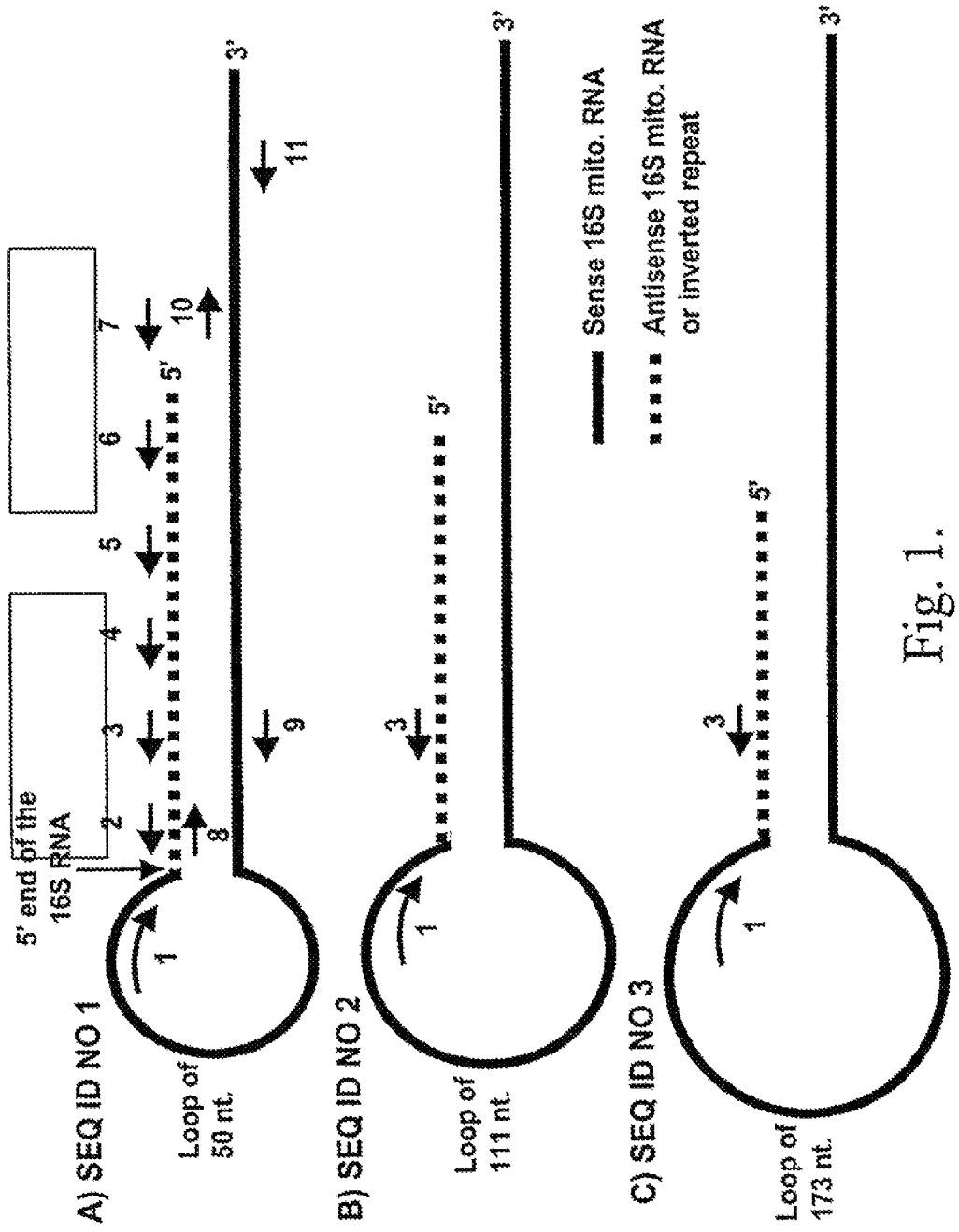
FIGS. 1A, B and C. Line drawings showing the structure of sense mitochondrial chimeric RNAs corresponding to SEQ ID NO 1, SEQ ID NO 2 and SEQ ID NO 3. The arrows indicate the relative position of the primers used to amplify the RNA by pieces. The arrows below the lines are reverse primers, and the arrows on top of the lines are forward primers. Primer 1 is positioned close to the 5' end of the 16S mitochondrial RNA. The Black lines correspond to the sense 16S mitochondrial RNA, while the doted lines correspond to the antisense 16S mitochondrial RNA.

In one embodiment of the present invention, the sense mitochondrial chimeric RNA can be detected for diagnostic purposes with a probe obtained by amplification of a region that contains part of the 5' end of the 16S ribosomal RNA and a partial or full region of the inverted repeat. As shown in FIG. 1, the reverse primer can be for example primer 1 (SEQ ID NO 139), and the forward primers can be primers 3, 4, 5, 6 or 7 (SEQ ID NOS 129, 116, 106, 102, 63). Primers located at other positions can also be used and they are easily designed by those skilled in the art. In another aspect of this invention, the cDNA which can be synthesized with an enzyme with reverse transcription activity and random primers such as hexamers or longer, familiar to those skilled in the art.

The amplicons of 210, 350, 500 or 850 bp obtained, or of other sizes resulting by using primers located at other positions, can be detected by get electrophoresis in agarose gel or polyacrylamide gels (Sambrook et al., 1989) and staining with ethidium bromide or other intercalating dyes. The amplicons can be purified according to the manufacturers instructive.

The detection of the mitochondrial chimeric RNA can be carried out by Northern blot analysis (Sambrook at al., 1989). After separation of the RNAs in an agarose gel, the fragments are transferred to a membrane (nitrocellulose or Nylon) by procedures well known to those skilled in the art (Sambrook et al., 1989). To probe the membranes, a fragment of 250 bp corresponding to position 1000 to 125 of the sense mitochondrial chimeric RNA can be amplified. The amplicon is purified (Wizard, Promega) according to the manufacture's intraction, and 10 nanograms are used as template for a second amplification. This amplification is carried out with the standard mixture of PCR (Invitrogen) plus 5 micro Curie of $^{32}P-\alpha$-dCTP (Amerscham). The radioactive amplification fragment is denatured by incubation at 95° C. for 10 minutes and the denatured probe was added to the hybridization mixture. The membranes are hybridized for 16 hours at 65° C. and then washed twice with 2 times SSC buffer, twice with 0.5 SSC at 60° C. and 0.2 SSC at 45° C. (Sambrook at al., 1989). The washed membrane was exposed to X-ray film overnight at −70° C. (Sambrook et al., 1989). The hybridization signal on the membrane corresponds to a major component of about 2,400 nucleotides which is the size corresponding to the 16S ribosomal RNA (1559 nucleotides) plus the inverted repeat of 815 nucleotides.

In another embodiment of the invention, part of the sense mitochondrial chimeric RNA can be detected after ribonuclease digestion of total RNA extracted from cells or tissues. The double stranded structure or the stem of the sense mitochondrial chimeric RNA is resistant to digestion with ribonuclease A. Total RNA from cells or tissues extracted with TriZol (Invitrogen) is dissolved in a small volume of 2 times SSC. The solution is incubated with ribonuclease A (Sigma) at a final concentration of 50 micrograms per ml. After 30 min at 25° C., the RNA resistant to the nuclease is extracted with TriZol and precipitated with isopropanol at −20° C. overnight. The RNA resistant to the nuclease is dissolved in distilled DEPC-treated water and used as template for RT-PCR amplification. This amplification, carried out with primers targeted to positions 55 and 790 of the 16S ribosomal RNA, yields a fragment of about 730 base pairs with a sequence that shows 100% identity with the sequence of the stem of the sense mitochondrial chimeric RNA (SEQ ID No 1). In contrast, the single strand of the chimeric RNA and corresponding to the 3' half, or the 12S mitochondrial ribosomal RNA, or the 18S ribosomal RNA or the mRNA for GAPDH are totally digested by the treatment with the ribonuclease A, and therefore, no amplification product is obtained when primers targeted to these RNAs are used.

In another aspect of the invention, the stem of the sense mitochondrial chimeric RNA obtained after treatment of total RNA with ribonuclease A can be detected by Northern blot. The RNA resistant to the nuclease and recovered by extraction with TriZol and precipitation with isopropanol, is separated by electrophoresis in an agarose gel. After transfer, the membrane is blotted with the probe described before and used for Northern blot (Sambrook et al., 1989) for the sense mitochondrial chimeric RNA.

In yet another embodiment, this invention is directed to kits suitable for performing an assay which detect the sense mitochondrial chimeric RNAs or the antisense mitochondrial chimeric RNA in biological samples. The general and the preferred embodiment, compositions and methods are provided which are suitable for the detection of the chimeric RNA and the antisense chimeric RNA by in situ hybridization have been previously described herein. Preferred oligonucleotide probes sequences, but not limited-to, are listed. Furthermore, methods suitable for using oligonucleotide probes or set of oligonucleotide probes of a kit to detect the chimeric RNAs or the antisense chimeric RNAs in a sample have been previously described herein.

The kit of this invention comprises one or more oligonucleotide probes and other reagents or compositions which are selected to perform in situ hybridization used to detect the sense mitochondrial chimeric RNAs or the antisense mitochondrial chimeric RNAs in a sample. Each set of two or more oligonucleotide probes are preferably labeled with independent detectable moieties so that in an individual cell of the biological sample the sense mitochondrial chimeric RNAs or the antisense mitochondrial chimeric RNAs can be detected. In a preferred embodiment, the oligonucleotide probes of the kit which are use to detect the sense mitochondrial chimeric RNAs or the antisense mitochondrial chimeric RNAs are each set labeled with a different hapten. The hapten can be biotin, digoxigenin or fluoresceine that can be recognized in the method of in situ hybridization with antibodies or streptavidin labeled with different enzymes (e.g. alkaline phosphatase or peroxidase). Alternatively, each oligonucleotide probe of each set of probes can be labeled with independent detectable fluorescent groups. For example, the set of oligonucleotides probes to detect the sense mitochondrial chimeric RNA can be labeled with rhodamin, while the set of oligonucleotides probes to detect the antisense mitochondrial chimeric RNAs can be labeled with Alexa 488. Furthermore, methods are provided to determine the localization of the chimeric RNA or the antisense chimeric RNAs in cells of the biological sample. Additionally, compositions and methods of the invention can be used to determine the co-localization of the chimeric RNAs or the antisense chimeric RNAs with specific markers of the different cell organelles, by using confocal microscopy analysis.

The compositions and methods provided herein are deemed particularly useful for the detection and diagnostic of pre-cancer and cancer. The term cancer as provided herein, includes cells afflicted by any one of the following identified anomalous conditions. These include myeloid leukemia acute or chronic, lymphoblastic leukemia acute or chronic, multiple myeloma, Hodgkin's disease, non-Hodgkin's lymphoma or malignant lymphoma; stomach carcinoma, esophagus carcinoma or adenocarcinoma, pancreas ductal adenocarcinoma, insulinoma, glucagonoma, gastrinoma, small bowel adenocarcinoma, colorectal carcinomas; hepatocellular carcinoma, hepatocellular adenoma; carcinoids, genitourinary tract such as kidney adenocarcinoma, Wilm's tumor, bladder and urethra carcinoma and prostate adenocarcinoma, testis cancer like seminoma, teratoma, teratocarcinoma, interstitial cell carcinoma; uterus endometrial carcinoma, cervical carcinoma, ovarian carcinoma, vulva and vagina carcinoma, Sertoll-L-eydig cell tumors, melanoma, and fallopian tubes carcinoma; lung, alveolar and bronchiolar carcinomas; brain tumors; skin malignant melanoma, basal cell carcinoma, squamous cell carcinoma and Karposl's sarcoma. Also fibrosarcoma, angiosarcoma and rhabdomyosarcoma of the heart and other malignancies that are familiar to those skilled in the art.

Cancer and Pre-Cancer Therapy

Chemoterapeutic drugs can induce a series of cellular responses that impact on tumor cell proliferation and survival. The best studied of these cellular responses is apoptosis and is evident at the present time that anti-cancer drugs can kill tumor cells by activating common apoptotic pathways. Unfortunately, these drugs also affect rapidly dividing normal cells of the bone marrow, normal hematopoietic and intestinal cells and hair matrix keratinocytes (McKinnell et al., The biological Basis of cancer, 1998; Komarov et al., Science 285:1733-1737, 1999; Johnstone at al., Cell 108:153-164, 2002).

On the other hand, many tumor cells have mutated apoptotic initiator factors, regulatory factors and executioner factors of apoptosis, which explain why tumor cell of different cancer types become resistant to a variety of chemotherapeutic drugs and radiation. Mutations have been reported of factors of the intrinsic pathway, post mitochondrial events and extrinsic pathway of apoptosis (Rampino et al., Science 275:967-969, 1997; Vogelstein et al., Nature 408: 307-310, 2000; Teitz et al., Nature Med. 6:529-535, 2000; Reed, J. Clin. Oncol., 17:2941-2953, 1999; Johnston et al., Cell 108: 153-184, 2002). Therefore, a paradigm of a cancer therapy treatment is a procedure that selectively triggers apoptosls of tumor cells, that does not alter normal proliferating cells and that bypasses the altered or mutated factors of the different apoptotic pathways.

The compositions and methods of the present invention, are based on the discovery that tumor and pre-tumor cells over express the sense mitochondrial chimeric RNA at similar levels of the normal proliferating cells. However, and in contrast with normal proliferating cells, tumor and pre-tumor cells down regulate the expression of the antisense mitochondrial chimeric RNA.

The structures of these transcripts are shown in FIG. 1 and FIG. 3, and the corresponding sequences in SEQ ID No 1, SEQ ID No 2, SEQ ID No 3, SEQ ID No 4, SEQ ID No 5 and SEQ ID No 6.

Figure 5A:
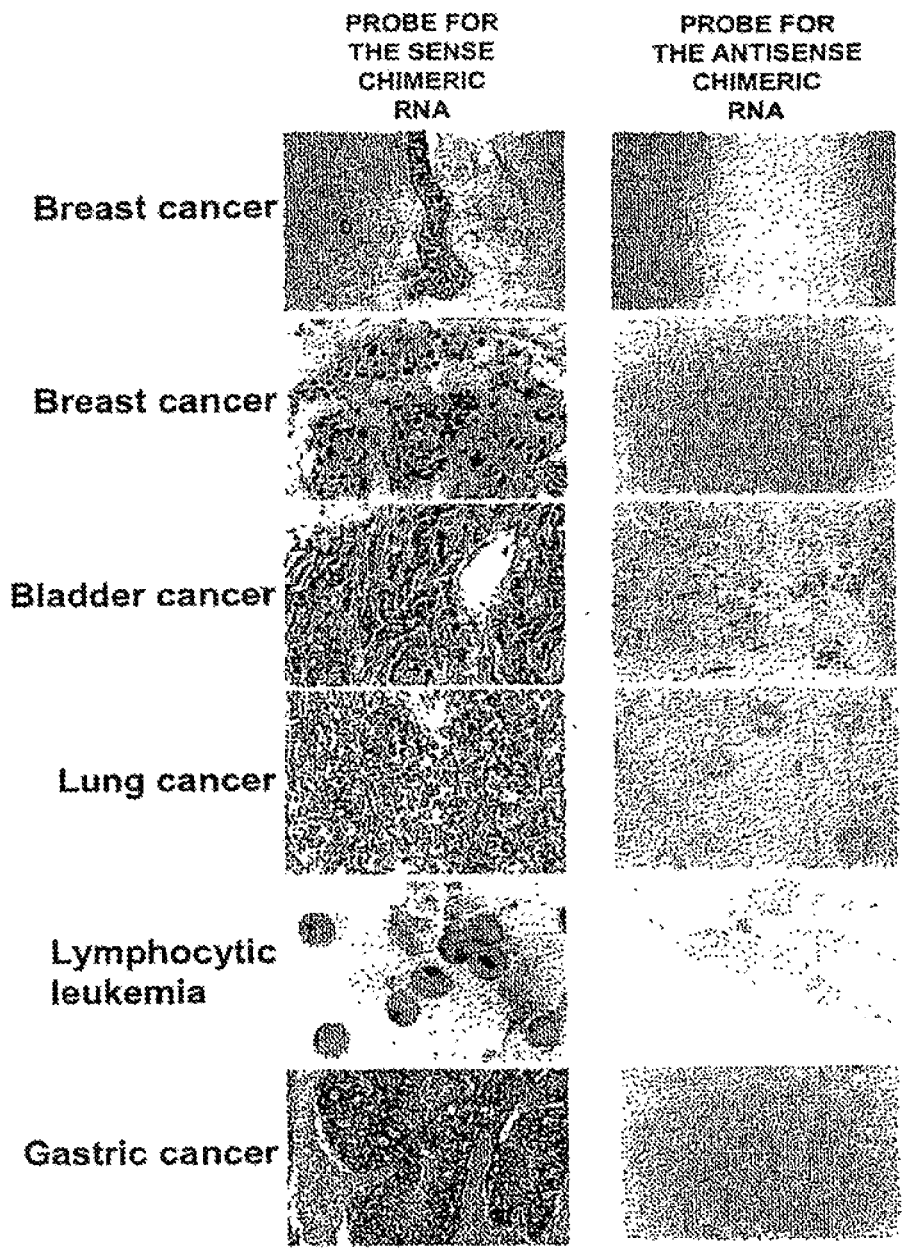
FIG. 5A. In situ hybridization of several sections of human biopsies corresponding to different tumor types. The tumor sections were hybridized with oligonucleotide probes complementary to the sense mitochondrial chimeric RNA, and labeled with digoxigene (left panels). In addition, parallel tumor sections were hybridized with oligonucleotide probes complementary to the antisense mitochondrial chimeric RNA labeled with digoxigenin (right panels).
Figure 5B:
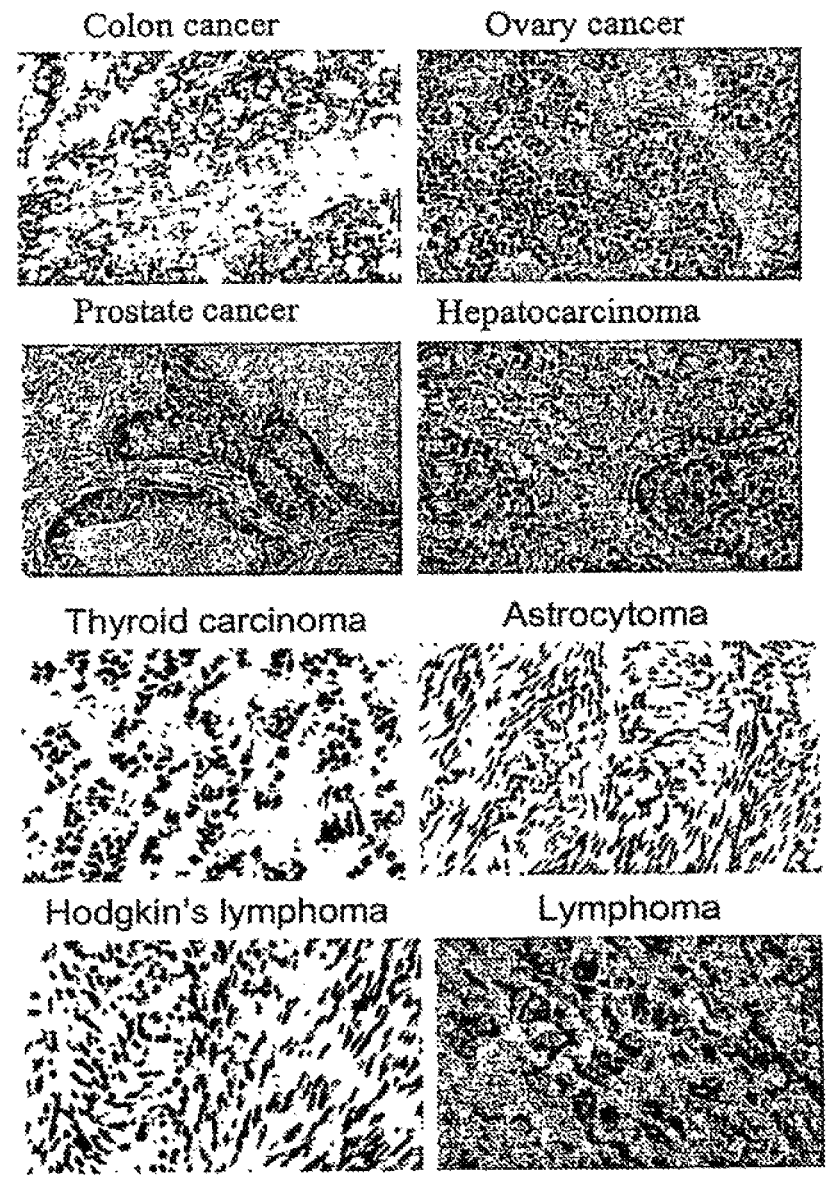
FIG. 5B are in situ hybridization of different human tumors carried out with oligonucleotide probes complementary to the sense mitochondrial chimeric RNA labeled with digoxigenin.

In contrast, and constituting another surprising discovery, pre-tumor and tumor cells overexpress the sense mitochondrial chimeric RNA and down regulate the expression of the antisense mitochondrial chimeric RNA. The suppression or inhibition of the synthesis of the antisense mitochondrial chimeric RNA in pre-tumor and tumor cells constitutes a novel difference on phenotype between a cancer cell and a normal proliferating cell, which is considered as one of the major embodiments of the present invention. Moreover, tumor cells in human biopsies of different cancer types, also exhibit the same phenotype of cancer cells in culture (FIGS. 5A and 5B).

Although the function of the sense mitochondrial chimeric RNA and the antisense mitochondrial chimeric RNA is not clear, a dose correlation exist between the expression of these RNAs and cell proliferation. For example, normal proliferating cells in tissues like liver, kidney and spleen, and defined as such by the expression of the antigens such K-67, PCNA or phosphorylated histone H3, over express the sense mitochondrial chimeric RNA as well as the antisense mitochondrial chimeric RNA. In the non-proliferating cells of the same tissues, which do not express Ki-67 or PCNA, the sense mitochondrial chimeric RNA and the antisense mitochondrial chimeric RNA are not expressed. Furthermore, and as illustrated in FIG. 7, human lymphocytes stimulated with the mitogen PHA synthesize DNA and express the proliferating antigens Ki-67 and PCNA. The stimulated lymphocytes also over express the sense mitochondrial chimeric RNA as well as the antisense mitochondrial chimeric RNA (FIG. 7). In contrast, resting lymphocytes or non-stimulated lymphocytes do not express neither the sense mitochondrial chimeric RNA nor the antisense mitochondrial chimeric RNA.

The previous finding, which is one fundamental part of the present invention, shows that while normal proliferating cells express the sense and antisense mitochondrial chimeric RNAs, tumor cells express the sense mitochondrial chimeric RNA and down regulate the expression of the antisense mitochondrial chimeric RNA. To understand the function of these RNAs in cell proliferation, cancer cells in culture were treated with antisense oligonucleotides targeted to the sense mitochondrial chimeric RNAs (SEQ ID No 1, SEQ ID No 2, SEQ ID No 3) or to the antisense mitochondrial chimeric RNA (SEQ ID No 4, SEQ ID No 5, SEQ ID No 6). The results, constituting another surprising discovery, showed that under these conditions the cells undergo programmed cell death or apoptosis. After treatment with the oligonucleotides complementary to the sense or antisense mitochondrial chimeric RNAs for 6 to 15 hours, between 75 to 96% of the cells undergo apoptosis (Table 2). The change observed in the treated cells were chromatin condensation, nuclear fragmentation, DNA fragmentation, activation of caspases and altered process of the cell membrane. Control oligonucleotides with 4 o more mismatches or scrambled oligonucleotides did not induce apoptosis. Also, cells were not affected if treated with oligonucleotides targeted to the sense or antisense 12S mitochondrial RNA or targeted to the mRNA or the antisense transcript of the mitochondrial ND1 subunit. In general, oligonucleotides targeted to the antisense mitochondrial chimeric RNA were much more effective, at the same concentration, than oligonucleotides targeted to the sense mitochondrial chimeric RNA. This was an expected result since the tumor cells over express the sense mitochondrial chimeric RNA and therefore is more difficult to reach a concentration of oligonucleotides inside the cell to interfere with all the copies of this transcript. On the other hand, since tumor cells down regulate the antisense mitochondrial chimeric RNA, it should be easier to interfere with this RNA since there is a lower number of copies per cells.

The induction of apoptosis is also selective for tumor cells. Resting human lymphocytes or human lymphocytes stimulated for 48 hours with PHA are not affected by the treatment with oligonucleotides complementary to the antisense mitochondrial chimeric RNAs or targeted to the sense mitochondrial chimeric RNA even after overnight treatment and with a high dose of complementary oligonucleotides (15 uM).

Apoptosis induction by treatment with complementary oligonucleotides targeted to the antisense mitochondrial chimeric RNA (SEQ ID No 4, SEQ ID No 5, SEQ ID No 6) has been achieved, but not limited to, promielocytic leukemia cell HL-60, acute lymphoblastic leukemia MOLT-4, a T-lymphocltic leukemia cells, Jurkat, a T-cell leukemia, Devernelle or B-lymphoma, NSO/2 or myeloma, HeLa cells, DU145, PC-3, Caco-2, Hep-2 and HepG2. Two cells, MCF/7 (breast carcinoma) and melanoma, that can be considered as paradigm of treatment-resistant (chemotherapy or radiotherapy) tumor cells undergo apoptosis over 80% when treated for 15 hours with complementary oligonucleotides targeted to the antisense mitochondrial chimeric RNA (SEQ ID No 4, SEQ ID No 5, SEQ ID No 6). A lower apoptotic effect was obtained with oligonucleotides complementary to the sense chimeric RNA (SEQ ID No 1). As reported before, oligonucleotides with 4 mistmatches or scrambled oligonucleotides do not induce cell death.

Described below are methods and compositions for treating cancer using the sense chimeric RNAs and the antisense chimeric RNAs as a therapeutic target.

The preferred embodiment, but not limited to, are methods and compositions for treating cancer using oligonucleotides complementary to the antisense chimeric RNAs. The outcome of this treatment is to at least produce in a treated subject a healthful benefit, which in the case of cancer, includes but is not limited to remission of the cancer, palliation of the symptoms of the cancer, and control of metastatic spread of the cancer. All such methods involve the induction of apoptosis in the tumor cells and with minor effect in normal cells. Complementary oligonucleotides that target specific RNAs have been used to diminish or abrogate the expression of a large variety of mRNA or the synthesis of the corresponding proteins (e.g. Vickers et al., J. Biol. Chem., 278:7108-7118, 2003). At present, about 42 antisense oligonucleotides with different chemistries are currently being screened as potential drugs (Stephens and Rivers, Curr. Opin. Mol. Therapeut., 5:118-122, 2003) (see also as examples U.S. Pat. Nos. 5,801,154; 8,576,759; 6,720,413; 6,573,050 and 6,673,917). All of these references are hereby expressly incorporated by reference.

In one aspect of this invention, one or more oligonucleotides targeted to the antisense mitochondrial chimeric RNA can be used. The use of two or more complementary oligonucleotides is more effective and shows some degree of synergism.

The oligonucleotide of the invention may be complementary to the antisense mitochondrial chimeric RNA or to the sense mitochondrial chimeric RNA. The complementary oligonucleotides will bind to the antisense mitochondrial chimeric RNAs or to the sense mitochondrial chimeric RNAs and interfere with their functions. Absolute complementarity, although preferred. Is not required. An oligonucleotide sequence "complementary" to a portion of an RNA, as referred to herein, means a sequence having sufficient complementarity to be able to hybridize with the RNA, forming a stable duplex. The ability to hybridize will depend on both the degree of complementarity and the length of the oligonucleotide. Generally, the longer the hybridizing nucleic acid, the more base mismatches with an RNA it may contain and still form a stable duplex. Those skilled in the art can ascertain a tolerable degree of mismatch by use of standard procedures to determine the melting point of the hybridized complex.

In general, complementary oligonucleotides to hybridize with mRNAs for different proteins are targeted to the 5' untranslated region of the mRNA including the complement of the AUG start codon, or the 3' untranslated region to be more effective. Oligonucleotides complementary to mRNA coding regions are less efficient inhibitors of translation (see previous references). The sense mitochondrial chimeric RNA and the antisense mitochondrial chimeric RNA are non-coding RNA and therefore the target region of the oligonucleotides can be complementary to any region of these transcripts. The most effective regions are located around the single-stranded segments of the antisense mitochondrial chimeric RNA determined by scanning the sequences of the antisense or the sense mitochondrial chimeric RNA with complementary oligonucleotides designed every 30 nucleotides. Those skilled in the art will understand that other sequences within the complete sequences of the transcripts of SEQ ID NO 1, SEQ ID NO 2, SEQ ID NO 3, SEQ ID NO 4, SEQ ID NO 5, and SEQ ID NO 6, are targets to design alternative complementary oligonucleotides.

The complementary oligonucleotides targeted to the antisense mitochondrial chimeric RNA or to the sense mitochondrial chimeric RNA resulting in the induction of tumor cell death according to the present invention will generally contain backbones different to the natural phosphodiester bonds. The oligonucleotides can have alternate inter nucleoside linkages, comprising, but not limited to, phosphorothioate (Mag at al., Nucleic Acids Res. 19:1437-1441, 1991; and U.S. Pat. No. 5,644,048), peptide nucleic acid or PNA (Egholm, Nature, 3685:566-568, 1993; and U.S. Pat. No. 6,656,687), phosphoramide (Beaucage, Methods Mol. Biol. 20:33-61, 1993), phosphorodithioate (Capaldi et al., Nucleic Acids Res., 28:E40, 2000). Other oligonucleotide analogs include such as, but not limited to, morpholino (Summerton, Biochim. Biophys. Acta, 1489:141-158, 1999), locked oligonucleotides (Wahlestedt wt al., Proc. Natl. Acad. Sci. US, 97:5633-5638, 2000), peptidic nucleic adds or PNA (Nielsen et al., 1993; Hyrup and Nielsen, 1996) or 2-o-(2-methoxy) ethyl modified 5' and 3' end oligonucleotides (McKay et al., J.

Biol. Chem., 274:1715-1722, 1999). All of these references are hereby expressly incorporated by reference. The nucleic acids may contain any combination of deoxyribo- and ribonucleotides, and any combination of bases, including uracil, adenine, thymine, cytosine, guanine, inosine, xathanine hypoxathanine, isocytosine, isoguanine, etc.

The complementary oligonucleotides according to the invention may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine. N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine The complementary oligonucleotides may also comprise at least one modified sugar moiety selected from the group including but not limited to arabinose, 2-fluoroarabinose, xylulose, and hexose.

In another embodiment of the present invention, the complementary oligonucleotides are designed to hybridize with any region of the antisense mitochondrial chimeric RNA or to any region of the sense mitochondrial chimeric RNA. The complementary oligonucleotides should be at least ten nucleotides in length, and are preferably complementary oligonucleotides ranging from 10 to about 50 nucleotides in length. In specific aspects, the complementary oligonucleotide is at least 12 nucleotides, at least 18 nucleotides, at least 22 nucleotides, at least 30 nucleotides, at least 50 nucleotides.

It is important to consider for in vitro as well as for in vivo experiments to utilize controls that distinguish between antisense interference with the function of the antisense mitochondrial chimeric RNA or the sense mitochondrial chimeric RNA with nonspecific biological effects of antisense or complementary oligonucleotides. Therefore, the design of the oligonucleotides has to avoid the presence in the sequence of CpG tracks, 5' GGGG tracks and other sequences that have toxic effect in animal cells as reported in U.S. Pat. No. 6,673,917, incorporated herein by reference. Also the presence of the sequence 5' CGTTA was avoided for the non-antisense effect that was reported (Tidd et al., Nucleic Acids Res. 28:2242-2260, 2000).

In another embodiment of the present invention, the complementary oligonucleotides targeted to the antisense mitochondrial chimeric RNAs or targeted to the sense mitochondrial chimeric RNAs as therapeutic agents to animals or to patients having cancer can induce sensitivity to anti-cancer therapeutic drugs and radiation. Induced sensitivity, also known as sensitization or hypersensitivity, can be measured in tumor cells showing tolerance to anti-cancer therapeutic or radiation. The anti-cancer drugs comprise those already known in the art and in use or as-yet undiscovered drugs. Among the conventional chemotherapeutic drugs are alkylating agents, anti-metabolite, antibiotics and anti-microtubule agents. Some examples of these drugs are cisplatin, methotrexate, doxorubicin dactinomycin, mitomycin, cyclophosphamide, etc.

In another aspect of the invention, together or after the treatment of an animal or a patient having cancer with complementary oligonucleotides targeted to the antisense mitochondrial chimeric RNA and/or the sense mitochondrial chimeric RNA, the patient can be treated with radiotherapy, wherein said radiotherapy includes ultraviolet radiation, gamma radiation, alpha particles, beta particles, X-ray and electron beams.

In another aspect of this invention, interference with the function of the antisense mitochondrial chimeric RNA or the sense mitochondrial chimeric RNA to induce tumor cell death can be achieved by RNA interference or RNA silencing. Over the last six years RNA interference (RNAi) has emerged as a novel and promising approach for gene silencing in mammalian cells (Elbashir et al., Nature 411:494-498, 2001; McManus et al., Nature Rev. Genet. 3:737-747, 2002). Synthetically synthesized double stranded RNA molecules of about 19 to 21 nucleotides in length hybridize specifically to their complementary target mRNA, leading to degradation of the mRNA and subsequent protein knockdown. Several different genes have been silenced successfully by small interfering RNA or siRNA (Lu et al., Curr. Opin. Mol. Ther. 5:225-234, 2003.; Wacheck et al., Oligonucleotides 13:393-400, 2003). Therefore, synthetic double stranded RNA of about 19 to 21 nucleotides targeted to the antisense mitochondrial chimeric RNA or to the sense mitochondrial chimeric RNA can be used to degrade these transcripts and induce tumor cell death. Those familiar in the art will understand that the sequence of the siRNA has to be complementary to any region of the antisense mitochondrial chimeric RNAs or to the sense mitochondrial chimeric RNAs (SEQ ID NO 1, SEQ ID NO 2, SEQ ID NO 3, SEQ ID NO 4, SEQ ID NO 5, and SEQ ID NO 6).

In another embodiment of the invention, ribozymes can be used to interfere with the antisense mitochondrial chimeric RNA or with the sense mitochondrial chimeric RNA to induce tumor cell death. The sequence of the ribozyme has to be designed according to the sequence of the antisense mitochondrial chimeric RNA (SEQ ID NO 4, SEQ ID NO 5, SEQ ID NO 6) or the sense mitochondrial chimeric RNA (SEQ ID NO 1, SEQ ID NO 2, SEQ ID NO 3) to cleave specific regions of the transcript that are more efficient to trigger tumor cell death. Ribozymes are enzymatic RNA molecules capable of catalyzing the specific cleavage of RNA (Rossi, Curr. Biology 4:469-471, 1994). The mechanism of ribozyme action involves sequence specific hybridization of the ribozyme molecule to complementary target RNA, followed by a endonucleolytic cleavage. The composition of ribozyme molecules must include one or more sequences complementary to the target gene mRNA, and must include the well known catalytic sequence responsible for mRNA cleavage, and described in U.S. Pat. No. 5,093,246, which is incorporated by reference herein in its entirety. As such, within the scope of the invention hammerhead ribozyme molecules are engineered that specifically and efficiently catalyze endonucleolytic cleavage of the antisense mitochondrial chimeric RNAs or the sense mitochondrial chimeric RNAs. The construction and production of hammerhead ribozymes is well known in the art and it was described (Haseloff at al., Gene, 82:43-52, 1989). Ribozymes of the present invention also include RNA endoribonucleases (Zaug et al., Science, 224:574-578, 1984).

Gene therapy refers to treatment or prevention of cancer performed by the administration of a nucleic acid to a patient who has cancer or in whom prevention or inhibition of cancer is desirable. In this embodiment of the present invention, the therapeutic nucleic acid produced intracellularly is a complementary RNA targeted to the antisense mitochondrial chimeric RNA or to the sense mitochondrial chimeric RNA that mediates the therapeutic effect by interfering or inhibiting the function of these mitochondrial transcripts, inducing tumor cell death. Therefore, one preferred approach is to utilize a recombinant DNA construct in which the transcription of the antisense RNA is placed under the control of strong promoters of RNA polymerase II or III. Expression of the sequence encoding the complementary RNA can be by any promoter known in the art to act in mammalian, preferably human cells. Such promoters include but are not limited to SV40 early promoter region (Benoist and Chambon, Nature 290:304-310, 1981), the herpes thymidine kinase promoter (Wagner et al., Proc. Natl. Acad. Sci. U.S.A. 78:1441-1445, 1981), the regulatory sequences of the metallothionein gene (Brinster et al., Nature 296:39-42, 1982), the promoter of Rous sarcoma virus (Yamamoto et al., Cell 22:787-797, 1980), etc. The recombinant DNA construct to produce the complimentary RNA can be a viral vector which includes, but is not limited to adenovirus vector, adeno-associated virus vector, herpes simplex virus vector, vaccinia virus vector and retrovirus vectors. The vector is introduced in the target tumor cells, in a pharmaceutical composition, using methods familiar to those skilled in the art.

Pharmaceutical compositions of the invention comprising an effective amount of a complementary nucleic acid (complementary oligonucleotides, siRNA, ribozymes or viral vectors) in a pharmaceutically acceptable carrier, that can be administered to a patient having cancer to interfere with the function of the antisense mitochondrial chimeric RNA or the sense mitochondrial chimeric RNA and induce apoptosis of the tumor cells. The complementary nucleic acids may be formulated in a pharmaceutical composition, which may include carriers, diluents, buffers, preservatives, surface active agents, polyethylenimine (PEI), liposomes or other lipid formulation known in the art. The pharmaceutical composition may be administered by topical application, oral, parenteral or rectal administration. Parenteral administration includes intravenous, subcutaneous, intraperitoneal or intramuscular injection or pulmonary administration by inhalation or insufflation.

The compositions of the present invention can be utilized for therapeutics, diagnostics, prophylaxis and as research reagents and kits.

The compositions and methods provided herein are deemed particularly useful for the treatment of cancer. The term cancer as provided herein, includes cells afflicted by any one of the following identified anomalous conditions. These include myeloid leukemia acute or chronic, lymphoblastic leukemia acute or chronic, multiple myeloma, Hodgkin's disease, non-Hodgkin's lymphoma or malignant lymphoma: stomach carcinoma, esophagus carcinoma or adenocarcinoma, pancreas ductal adenocarcinoma, insulinoma, glucagonoma, gastrinoma, small bowel adenocarcinoma, colorectal carcinomas; hepatocellular carcinoma, hepatocellular adenoma; carcinoids, genitourinary tract such as kidney adenocarcinoma, Wilm's tumor, bladder and urethra carcinoma and prostate adenocarcinoma, testis cancer like seminoma, teratoma, teratocarcinoma, interstitial cell carcinoma; uterus endometrial carcinoma, cervical carcinoma, ovarian carcinoma, vulva and vagina carcinoma, Sertoli-L-eydig cell tumors, melanoma, and fallopian tubes carcinoma; lung, alveolar and bronchiolar carcinomas; brain tumors; skin malignant melanoma, basal cell carcinoma, squamous cell carcinoma and Karposi's sarcoma. Also fibrosarcoma, angiosarcoma and rhabdomyosarcoma of the heart and other malignancies that are familiar to these skilled in the art. Thus, the term "cancerous cell" as provided herein, includes a cell afflicted by any one of the above identified conditions.

The following examples serve to describe the manner of using the above-described invention as well as to set forth the best manner for carrying out various aspects of the invention. It is understood that in no way these examples meant to limit the scope of this invention, but rather they are presented for illustrative purposes.

Example 1

Isolation and Sequence of the Sense Mitochondrial Human Chimeric RNA (FIG. 1A, SEQ ID NO1)

Figure 2:
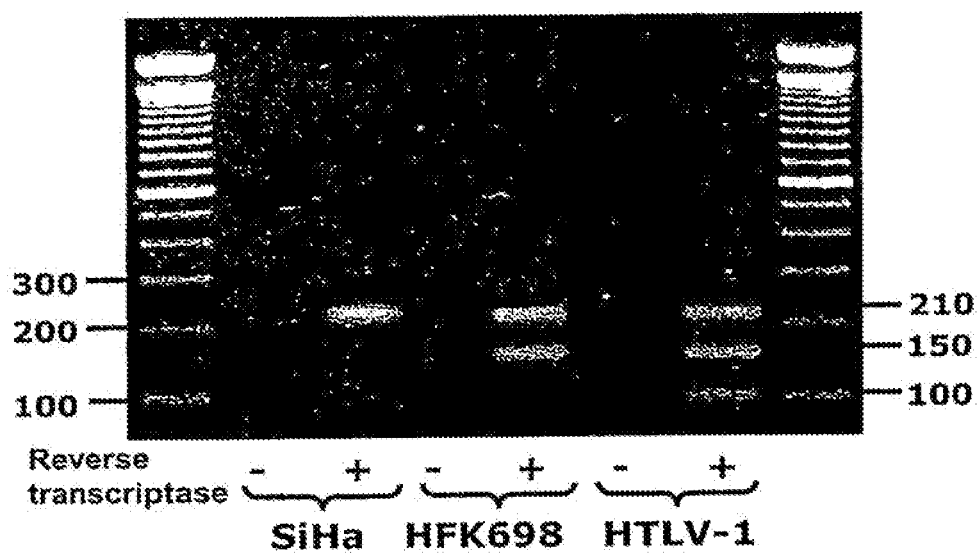
FIG. 2. Agarose gel electrophoresis to show the amplification product obtained between primer 1 and primer 3 indicated in FIG. 1A. The amplification was carried out by RT-PCR using as template a tumor cell (SiHa), human keratinocytes transformed with HPV 16 (HFK698) or B-lymphocytes transformed with HTLV-1. With RNA from SiHa cells only one single amplicon of 210 bp was obtained and corresponds to a segment of SEQ ID NO 1. In total RNA of keratinocytes transformed with HPV 16, besides the amplicon of 210 bp, a second amplicon of 150 bp was obtained and corresponds to a segment of SEQ ID NO 2. With RNA from cells transformed with HTLV-1, besides the amplicons of 210 bp and 150 bp, a third amplicon was obtained and corresponds to a segment of SEQ ID NO 3.

Initial experiments indicated that the putative human sense mitochondrial chimeric RNA contained a more complex and stable secondary structure that the mouse chimeric RNA (Villegas et al, DNA & Cell Biol. 19:579-588, 2000; Villegas et al., Nucleic Acids Res. 30:1895-1901, 2002). Therefore, and based in the mouse mitochondrial chimeric RNA secondary structure, a theoretical human sense mitochondrial chimeric RNA secondary structure was deduced (FIG. 1A). The theoretical human transcript contained the complete sequence of the sense 16S mitochondrial RNA joined by the 5' end to a fragment of the antisense 16S mitochondrial RNA forming a loop of unknown length (FIG. 1A). The segment of the antisense 16S mitochondrial RNA was fully complementary to the sense 16S mitochondrial RNA and therefore corresponded to an inverted repeat joined to the 5' end of the sense 16S transcript. Based on this structure, primers were designed to amplify this putative transcript by RT-PCR. One reverse primer was at position 11 to 31 from the 5' end of the human sense 16S mitochondrial RNA or at the beginning of the theoretical loop (primer 1, FIG. 1A) (SEQ ID NO 139). The sequence of the forward primer used was that of positions 213-234 of the sense 16S mitochondrial RNA, and corresponds to primer 3 in FIG. 1A. Amplification of RNA from several human tissues and cells including HeLa, HL-60, Du145, MCF/7 and human lymphocytes stimulated with PHA (see Example 7) by RT-PCR using primers 1 and 3 (FIG. 1A), yielded a unique amplicon of about 210 bp (FIG. 2). RT-PCR was carried out as described before (Villegas at al., DNA & Cell Biol. 19:579-588, 2000; Villegas et al., Nucleic Acids Res. 30:1895-1901, 2002). The amplicons from each human tissue or cells were cloned and both strands were sequenced. In all cases, an identical sequence of 2186 bp was obtained, containing an inverted repeat of 184 nucleotides joined to the first 31 nucleotides of the 5' end of the sense 16S mitochondrial RNA. Then, we determined if the inverted repeat was longer than 184 nucleotides and extended further toward the 5' end of the antisense 16S mitochondrial RNA (FIG. 1A). The cDNA from HeLa or other cells described before was amplified between the reverse primer 1 positioned at the loop as described before, and primers 4 to 7 to walk toward the 5' end of the putative longer inverted repeat (FIG. 1A). By using this approach, amplification fragments of approximately 500, 700 and 800 bp were obtained when primer 1 was used in combination with primers 4, 5 and 6, respectively. On the other hand, when the cDNA was amplified between primer 1 and primer 7 no amplification product was obtained, suggesting that the 5' end of the inverted repeat was between primers 7 and 8 (see below). The complete sequence of the amplicon of 800 bp reveals an inverted repeat of 769 nucleotides joined to the first 31 nucleotides of the sense 16S mitochondrial RNA (SEQ ID NO 1) (FIG. 1A). The sequence at the 3' end of the inverted repeat joined to the sense 16S mitochondrial RNA was identical to that found in the same region of the amplicon of 216 bp. This is important because it indicates that in both cases we were amplifying the same RNA. In addition, the sequence showed that 50 nucleotides of the 3' end of the antisense 16S mitochondrial RNA were missing in the inverted repeat of the sense mitochondrial chimeric RNA. Altogether, these results suggest that the double stranded structure formed between the inverted repeat and the sense 16S mitochondrial RNA begins at position 51 of the latter, and forms a putative loop of 50 nucleotides.

To confirm the size of the loop, human cDNA was amplified by PCR between the forward primer 2 positioned at the 3' end of the inverted repeat and primer 3, which is also reverse at position 213-234 of the sense 16S mitochondrial RNA (FIG. 1A). An amplicon of approximately 240 bp was obtained and the sequence showed that the first 234 nucleotides of the sense 16 S mitochondrial RNA were joined to the last 25 nucleotides of the 3' end of the inverted repeat. The sequence of the 25 nucleotides of the inverted repeat was fully complementary to the sense 16S mitochondrial RNA from positions 51 to 75 (FIG. 1A).

If the sequence of the amplicon obtained with primers 1 and 6 and the sequence of the amplicon obtained with primers 2 and 3 are assembled as contigs, the emerging structure of the human sense mitochondrial chimeric RNA confirmed a loop of 50 nucleotides and a double stranded structure of at least 769 bp (FIG. 1A) (see also SEQ ID NO 1).

Since double stranded RNA is not digested by RNase A, the stem of the human sense mitochondrial chimeric RNA should be resistant to this enzyme. On the other hand, the loop or the 3' region of the sense 16S mitochondrial RNA strand that extended beyond the double stranded structure should be digested by the enzyme. RNA from HeLa or other cells was digested with RNase A (50 ug per ml), followed by phenol extraction, and the nuclease-resistant material was recovered by ethanol precipitation. The cDNA from the digested RNA was then amplified by PCR using the primers showed in FIG. 1A. The amplicon of about 800 bp obtained with primers 1 and 6 was not amplified after RNase A digestion indicating that the loop was digested by the enzyme. The same was true with the amplicon of 360 bp obtained with primers 10 and 11 as indicated in FIG. 1A. Altogether, these results indicated that the loop as well as the 3' region of the sense mitochondrial chimeric RNA that extends beyond the stem, were digested by the enzyme. On the other hand, amplification of the 750 bp amplicon, corresponding to the double stranded structure of the sense mitochondrial chimeric RNA and obtained with primers 8 and 6, was not affected by the RNase A digestion. The sequence of the double strand fragment resistant to ribonuclease digestion was identical with the expected sequence of the stem. The same results were obtained after digestion of total RNA from HL-60 cells or other human cells.

To determine the 5' end of the inverted repeat of the sense mitochondrial chimeric RNA, the stem of the transcript obtained after RNase A digestion was used for 5' RACE analysis. The 5' end determination of the inverted repeat was carried out according to the manufacturer's instructions (Invitrogen). The results indicated that the inverted repeat extends for 46 additional nucleotides from the 5' end of the amplicon obtained after amplification of the sense mitochondrial chimeric RNA with primers 1 and 6. In summary, the inverted repeat of 815 nucleotides is joined to the 5' end of the first 865 nucleotides of the 16S mitochondrial RNA. The sequence of this transcript showed 99.8% identity with the human 16S mitochondrial gene (H and L strand) (SEQ ID NO 1). The 5' ends of both extremes of the double stranded stem were confirmed by 5' RACE.

The above results indicated that the sense mitochondrial chimeric RNA contained a stem or double stranded structure of 815 base pair and a loop of 50 nucleotides. However, these results do not prove that the inverted repeat is joined to the complete 16S sense mitochondrial RNA. The use of conventional approaches such as synthesis of the complete cDNA from the 3' end is useless, since the double stranded structure of the transcript represents a insurmountable problem to reverse transcriptases, including Tth (Myers and Gelfand, Biochemistry 30:7661-7666, 1991). If the inverted repeat of 815 nucleotides is joined to the 1559 nucleotides of the 16S mitochondrial RNA one would expect a transcript of 2.3 Kb. Northern blot analysis of total RNA from HeLa, HL-60 and MCF/7 cells were carried out with a probe labeled with $^{32}P$ and targeted to the double stranded structure of the sense mitochondrial chimeric RNA. The results revealed a band of about 2.4 Kb, besides a band of 1.6 Kb, corresponding to the sense mitochondrial chimeric RNA and the sense 16S mitochondrial RNA, respectively. If the RNA was digested with RNase A previous to the Northern blot, a single hybridization band of approximately 0.8 Kb was obtained, which corresponds to the size of the stem of the sense mitochondrial chimeric RNA. Altogether, these results strongly demonstrated that the sense mitochondrial chimeric RNA contained an inverted repeat of 815 nucleotides joined to the 5' end of the complete sense 16S mitochondrial RNA, and corresponding to SEQ ID NO 1.

It is possible to specifically detect the junction region between the inverted repeat and the sense 16S mitochondrial RNA, using an oligonucleotide probe. The probe has to include 7 to 10 nucleotides at each side of the joining point between the 3' end of the inverted repeat and the beginning of the sense 16S mitochondrial RNA. This oligonucleotide can be used for in situ hybridization or amplification by RT-PCR or any other methods familiar to those skilled in the art to detect this novel RNA.

The sense mitochondrial chimeric RNA is present in normal proliferating cells (human foreskin keratinocytes, spleen, lymphocytes stimulated with PHA, mouse embryos), in pre-cancer cells (keratinocytes transformed with HPV 16 or 18, MT-2 cells transformed with HTLV-1) and in tumor cells. It is not present in normal resting cells. A summary of these results is presented in Table 1 (in Example 4).

Example 2

Human Keratinocytes Transformed with Papilloma Virus Synthesize a Novel Sense Mitochondrial Chimeric RNA (FIG. 1B, SEQ ID NO 2)

Human foreskin keratinocytes (HFK) were transformed by incubation with a lysate of cells previously infected with the human papilloma virus 16 (HPV 16). The cells were cultured with 3 parts of K-SFM, one part of DMEM medium (Invitrogen), 5 ng/ml of EGF, 50 ug/ml of pituitary extract and 10% calf fetal serum. The culture conditions were 37° C. and 5% CO2. After 24 hours of infection, the transformed HFK were transferred to a new flask and grown under the same conditions. After this time the cells (HFK698) were successively transferred to new culture flasks every 3 days using a split ratio of 1:3 to 1:4. After passage 19th the cells (HFK698 transformed with HPV 16) were harvested as described (Hausen, Biochim. Biophys. Acta, 1288:F55-F78, 1996), collected by centrifugation at 300×g for 10 min and washed twice with saline phosphate buffer (PBS). Total RNA was extracted from the washed cells with Trizol (Invitrogene). About 200 nanograms of RNA were used to synthesize the cDNA with random hexamers as described in Example 1. The cDNA was amplified by PCR using the reverse primer 1 and the forward primer 3 as described in FIG. 1A. This amplification protocol yielded the expected amplicon of 210 bp where the first 31 nucleotides of the sense 16S mitochondrial RNA are joined to the inverted repeat of 184 nucleotides as described before in Example 1. Electrophoresis analysis of the amplification products revealed the presence of the amplicon of 210 base pairs corresponding to the sense mitochondrial chimeric RNA, plus another amplification fragment of about 150 base pairs as shown in FIG. 2. The complete sequence of this new fragment (SEQ ID NO 2) showed that the initial 31 nucleotides from the 5' end of the sense 16S mitochondrial RNA are joined to an inverted repeat of 121 nucleotides, which is shorter in 63 nucleotides if compared with the inverted repeat of the sense mitochondrial chimeric RNA of SEQ ID NO 1. This shorter inverted repeat generates a longer loop of 96 nucleotides (FIG. 1B) in the structure of the mitochondrial chimeric RNA. The remaining of the sequence is identical to SEQ ID NO 1). This novel sense mitochondrial chimeric RNA is not present in SiHa cells (FIG. 4A), which are tumorigenic cells transformed with HPV 16, nor in normal proliferating human cells like human lymphocytes stimulated with PHA (see Example). Similar results were obtained with HFK transformed with HPV 18 or 18Nco cells. The cells transformed or immortalized (but not tumorigenic) with HPV 16 or HPV 18 are considered as pre-malignant cells and therefore the novel sense mitochondrial chimeric RNA is a new potential marker for pre-malignant cells.

Since the sequence of the 3' end of the inverted repeat of SEQ ID NO 2 joined to the 16S mitochondrial RNA is different to the same region of SEQ ID NO 1, an oligonucleotide probe can be used for the specific detection of this transcript. The probe has to include 7 to 10 nucleotides at each side of the joining point between the 3' end of the inverted repeat and the beginning of the sense 16S mitochondria RNA, such as the oligonucleotide of SEQ ID NO 7. This oligonucleotide can be used for in situ hybridization or amplification by RT-PCR or any other methods familiar to those skilled in the art to detect this novel and specific maker of pre-cancer cells.

Example 3

Cells Transformed with HTLV-1 Induce the Expression of a Third Novel Sense Mitochondrial Chimeric RNAs (FIG. 1C, SEQ ID NO 3)

Human MT-2 cells transformed with HTLV-1 were cultured as described (Kobayashi et al., EMBO J., 3:1339-1343, 1984). The cells were harvested, centrifuged at 300×g for 10 min and washed twice with PBS. The final cell pellet was extracted with Trizol as described in Example 1. The cDNA was synthesized with random hexamers using the RNA as template and the cDNA was amplified by PCR using the reverse primer 1 and the forward primer 3 as described in FIG. 1A. As described before, this amplification protocol yields an amplicon of 210 base pair that contains the first 31 nucleotides of the sense 16S mitochondrial RNA joined to an inverted repeat of 184 nucleotides which corresponds to the sense mitochondrial chimeric RNA as described in Example 1. Electrophoresis analysis of the amplification products revealed, besides the presence of the already discussed amplicon of 210 base pair, a band of about 150 base pair (see FIG. 2). The sequence of the amplicon of 150 base pair is identical to the sequence of the amplicon described in Example 2, corresponding to a second sense mitochondrial chimeric RNA expressed in cells transformed with HPV 16 or HPV 18 (SEQ ID NO 2). In addition, a new amplification product was found of about 100 bp (FIG. 2). The sequence of this third amplicon revealed an inverted repeat of 61 nucleotides joined to the 5' end of the sense 16S mitochondrial RNA and generating a loop of 187 nucleotides (FIG. 1C; SEQ ID NO 3). This novel amplicon was not present in normal cells, in tumor cells and in cells transformed with HPV 16 or 18. Therefore, this new sense mitochondrial chimeric RNA is a potential marker of cells transformed with the oncogenic retrovirus HTLV-1.

Since the sequence of the 3' end of the inverted repeat of SEQ ID NO 3 joined to the 16S mitochondrial RNA is different to the same region of SEQ ID NO 1 and SEQ ID NO 2, an oligonucleotide probe can be used for the specific detection of this transcript. The probe has to span between 7 to 10 nucleotides at each side of the joining point between the 3' end of the inverted repeat and the beginning of the sense 16S mitochondrial RNA, such as oligonucleotide of SEQ ID NO 8. This oligonucleotide can be used for in situ hybridization or amplification by RT-PCR or any other methods familiar to those skilled in the art to detect this specific marker of cells transformed with a retroviral oncogenic virus.

Example 4

Structure of the Human Antisense Mitochondrial Chimeric RNA

Our initial experiments indicated that a second family of chimeric RNAs corresponding to the antisense mitochondrial chimeric RNA was present in some of the cells studies. To establish the structure of the human antisense mitochondrial chimeric RNA, the strategy used for the sense mitochondrial chimeric RNA was employed (FIG. 1). The theoretical antisense mitochondrial chimeric RNA contained a fragment of the sense 16S mitochondrial RNA as inverted repeat joined to the 5' end of the antisense 16S mitochondrial RNA. The latter RNA is transcribed from the L-strand of the mitochondrial DNA and corresponds to the 16S mitochondrial gene (FIG. 3). To amplify this RNA, a reverse primer was hybridized close to the 5' end of the antisense 16S mitochondrial RNA and forward primers were hybridized at different positions of the putative fragment of the inverted repeat (FIG. 3). Total RNA from human lymphocytes stimulated with PHA for 48 h was used as template. The cDNA was synthesized with random hexamers as described in Example 1. Amplification of the cDNA by PCR was carried out with the reverse primer positioned close to the beginning of the 5' end of the antisense 16S mitochondrial RNA (primer 1, FIG. 3) and different forward primers positioned on the inverted repeat (FIG. 3). Only three major amplicons were obtained which differed in the size of the inverted repeat and the size of the loop. These amplicons were purified and sequenced. One of these antisense mitochondrial chimeric RNA contains an inverted repeat of 365 nucleotides and a loop of 17 nucleotides (SEQ ID NO 4). Another RNA contains a loop of 96 nucleotides and an inverted repeat of 189 nucleotides (SEQ ID NO 5). Yet, another specie of the antisense mitochondrial chimeric RNA contains an inverted repeat of 296 nucleotides and a loop of 451 nucleotides (SEQ ID NO 6). The sequences of all three antisense mitochondrial chimeric RNAs were 99.8 percent homologous with the sequence of the mitochondrial DNA gene (H and L strand).

The results, which will be presented in the following examples indicate that there is a major difference between pre-tumor and tumor cells and normal proliferating cells with respect to the expression of the antisense mitochondrial chimeric RNA. All proliferating cells overexpress the sense mitochondrial chimeric RNA. However, while normal proliferating cells also express the antisense mitochondrial chimeric RNAs, these transcripts are down regulated in tumor cells. Non-proliferating or resting cells do not express either mitochondrial chimeric RNAs. Therefore, the differential expression of these RNA represents a novel and powerful marker of carcinogenesis, which can be detected by in situ hybridization, Northern blot analysis, RT-PCR or TMA or other techniques known by one skilled in the art.

A summary of the differential expression of the sense and antisense mitochondrial chimeric RNAs is shown in Table 1.

TABLE 1

Expression of the chimeric RNAs in different type of cells.

| Chimeric RNAs | Normal Resting | Normal Proliferating | Transformed with HPV | Transformed with HTLV-1 | Cancer |
|---|---|---|---|---|---|
| SEQ ID NO 1 | -- | +++++ | +++++ | +++++ | +++++ |
| SEQ ID NO 2 | -- | -- | ++++ | ++++ | -- |
| SEQ ID NO 3 | -- | -- | -- | ++++ | -- |
| SEQ ID NO 4 | -- | +++++ | +/- | +/- | +/- |
| SEQ ID NO 5 | -- | +++++ | +/- | +/- | +/- |
| SEQ ID NO 6 | -- | +++++ | +/- | +/- | +/- |

+ and −: relative level of expression by in situ hybrization

Example 5

Tumor Cells Lines Over Express the Sense Mitochondrial Chimeric RNA (SEQ ID NO 1) and Down Regulate the Expression of the Antisense Mitochondrial Chimeric RNA (SEQ ID NOS 4, 5 and 6)

In situ hybridization was used to determine the expression of the sense mitochondrial chimeric RNA in tumor cell lines in culture. For in situ hybridization, adherent tumor cells were cultured in 8-wells chamber slides (Lab-Tek®, NUNC) for 24 to 48 h at 37° C. using the appropriate medium and conditions recommended by American Tissue Culture Collection or ATCC. For non-adherent cells (e.g. HL-60, Jurkat and Ramos), they were cultured in small flask for 48 hours at 37° C. The cells were recovered by centrifugation at 300×g for 10 min, resuspended in small volume of PBS and aliquots of 10 to 20 ul were applied on glass slides previously coated with polylysine or an adhesive protein purified from mussels (Burzio et al, Curt. Opin. Biotechnol., 8:309-312, 1997). The cells were dried at room temperature for 30 min.

The cells were washed three times with PBS and fixed with 4% para-formaldehyde for 10 min at room temperature. The slides were then washed three times with PBS for 5 min and incubated with 0.2 N HCl for 10 min at room temperature. The cells were washed again three times, first with PBS and then with 2×SSC for 10 min (2×SSC: 0.3 M NaCl, 30 mM sodium citrate, pH 7.0) (Sambrook et al., 1989) at room temperature. The prehybridization was carried out for 30 min at 37° C. In a solution containing 4×SSC, 10% dextran sulfate, 150 µg/ml yeast tRNA and herring sperm DNA, 50% formamide and 1×Denhardt solution (0.2 mg/ml Ficoll type 400, 0.2 mg/ml polivinlipirrolidone, 0.2 mg/ml BSA). Hybridization was carried out for 15 hours at 37° C. in the same prehybridization mixture containing 3.5 pmoles of probes targeted to the sense and antisense mitochondrial chimeric RNAs. The probes contained of 20 or more deoxynucleotides targeted to different regions of the sequence of the sense or antisense mitochondrial chimeric RNA (see SEQ ID NO 99 to 197 and SEQ ID NO 9 to 98, respectively). The probes were previously labeled at the 3' end with digoxigenin-11-dUTP (Roche) and terminal transferase (Promega) as described before (Villegas et al., DNA & Cell Biol., 19:579-588, 2000). To eliminate the excess of probe, the slides were washed first with 2×SSC for 10 min and with 1×SSC for 10 min at room temperature. Then the samples were washed with 0.2×SSC for 30 min at 45° C. and finally, with 0.2×SSC for 10 min at room temperature.

After hybridization, the cells were incubated for 30 min in blocking buffer (1% BSA, 0.3% Triton X-100 in PBS) and then incubated for 2 h at room temperature with anti-digoxigenin monoclonal antibody conjugated to alkaline phosphatase (Roche), previously diluted 1:500 in the blocking buffer. Finally, the slides were washed twice with PBS and the color reaction was carried out with a BCIP/NBT substrate mixture (DAKO) as described before (Villegas at al., DNA & Cell Biol., 19:579-588, 2000). The same procedure was employed for FISH, using anti-digoxigenin antibodies conjugated with fluorescein or rhodamine.

Figure 4A:
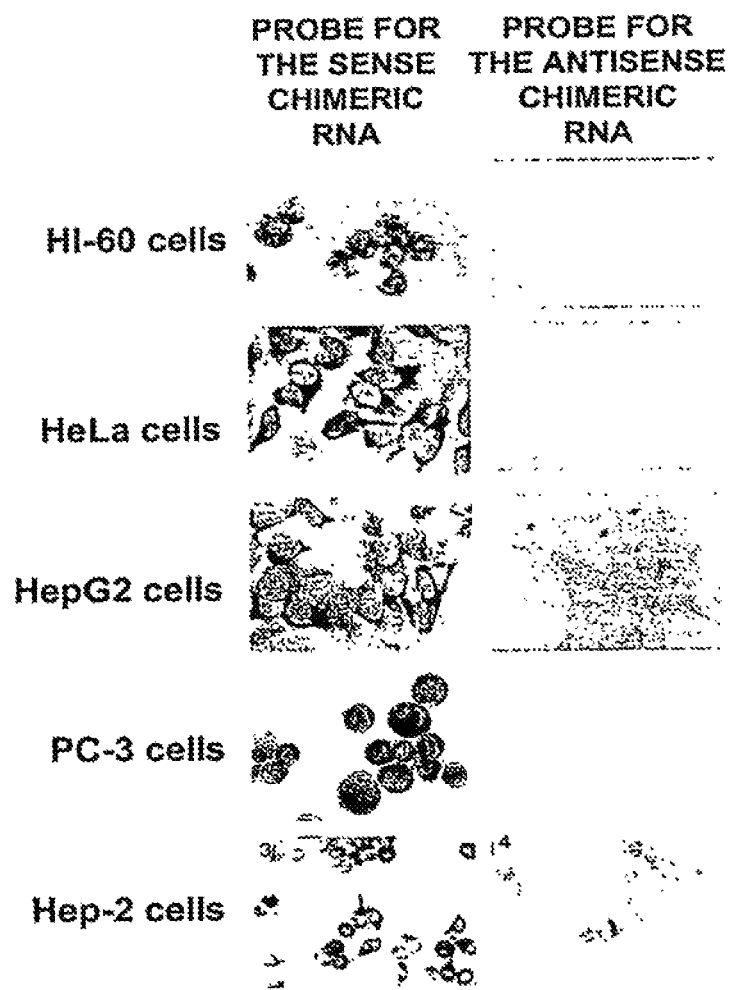
FIGS. 4A and 4B. In situ hybridization assays carried out with several tumor cell lines in culture. The cells were hybridized with oligonucleotide probes complementary to the sense mitochondrial chimeric RNA, and labeled with digoxigenin (left panels). In addition, the cells were also hybridized in parallel with oligonucleotide probes complementary to the antisense mitochondrial chimeric RNA labeled with digoxigenin (right panels). The cells fines are identified at the left.
Figure 4B:
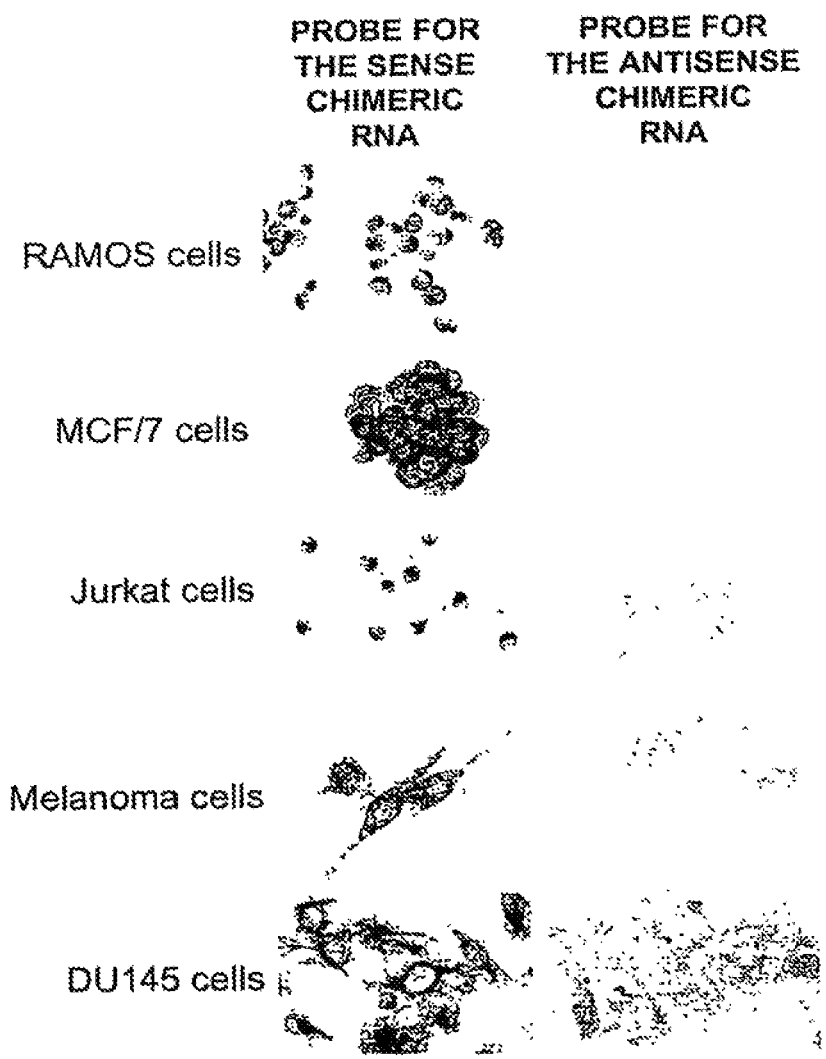

As shown in FIGS. 4A and 4B, in situ hybridization with a probe labeled with digoxigenin corresponding to SEQ ID NO 63 reveals that human tumor cells overexpress the sense mitochondrial chimeric RNA. In situ hybridization with the sense probe labeled with digoxigenin and corresponding to SEQ ID NO 64 was negative (FIGS. 4A and B) indicating down regulation of the expression of the antisense mitochondrial chimeric RNA. The same results were obtained with oligonucleotide probes targeted to other regions of the sense or antisense mitochondrial chimeric RNA.

Example 6

Tumor Cells in Human Biopsies Over Express the Sense Mitochondrial Chimeric RNA (SEQ ID NO 1) and Down Regulate the Antisense Mitochondrial Chimeric RNA (SEQ ID NOS 4, 5 and 6)

Human biopsies were obtained from pathologists or tissue arrays from DAKO. Most of the samples analyzed were paraffin-embedded and fixed with formalin. Other tissue samples were fixed with Boiun's fixative and another samples were fresh frozen tissue sections. The tissue sections of about 4 to 8 µm were fixed on slides previously coated with polylysine or the adhesive polyphenolic protein purified from the mussel Aulacomya ater (Burzio et al., Curr. Opin. Biotechnol., 8:309-312, 1997). The paraffin-embedded tissue sections were incubated for 1 h at 60° C., and the paraffin was removed by three washes with xylol for 15 min each time. The sections were air dried and washed four times with PBS. Then the sections were incubated with 0.2 N HCl for 10 min at room temperature and then thoroughly washed with PBS. Afterwards, the samples were subjected to in situ hybridization with the antisense probes labeled with digoxigenin according to protocol described in Example 4. A parallel section was hybridized with a sense probe corresponding to the same region of the sense mitochondrial chimeric RNA.

As shown in FIG. 5A, the cells present in tumors of breast, uterine cervix, bladder and lung carcinoma revealed a strong staining with the antisense probes targeted to the sense mitochondrial chimeric RNA, indicating strong presence of the transcript. On the other hand the in situ hybridization with the probe targeted to the antisense mitochondrial chimeric RNA was negative, indicating down regulation of this transcript (FIG. 5A). Other tumors also over express the sense mitochondrial chimeric RNA, and down regulate the expression of the antisense mitochondrial chimeric RNA (FIG. 5B).

Example 7

Normal Proliferating Cells Over Express the Sense and the Antisense Mitochondrial Chimeric RNAs Using the same protocol for in situ hybridization described in Examples 5 and 6, the expression of the sense mitochondrial chimeric was determined in proliferating cells. As shown in FIG. 6, HFK cells, spermatogonia, spleen cells and proliferating cells of mouse embryo, showed strong hybridization signal indicating over expression of the sense mitochondrial chimeric RNA. In contrast, non-proliferating cells such as cells of the brain, muscle and liver show no signal indicating that the sense mitochondrial chimeric RNA is not expressed or is down regulated in these cells.

However, the surprising result was that when the in situ hybridization was carried out with probes targeted to the antisense mitochondrial chimeric RNA, a strong signal was also observed (FIG. 6). Several controls assayed in parallel indicated that the hybridization signal with these probes was not due to an artifact. The hybridization signal disappeared if the in situ hybridization was carried out with the labeled probe together with an excess (50 to 100 times) of the same probe but non-labeled with digoxigenin. If previous to the hybridization the samples were incubated with ribonuclease A overnight, the hybridization signal disappeared. Also, no hybridization signal was observed if the hybridization was carried out with a labeled probe targeted to the antisense mitochondrial chimeric RNA with 4 mistmaches.

Example 8

Normal Human Lymphocytes Stimulated with Phytohaemagglutinin (PHA) Overexpress the Sense and the Antisense Mitochondrial Chimeric RNAs Five ml of blood from healthy donors were collected with EDTA. The blood was diluted with one volume of 0.9% NaCl and the mixture was applied on 5 ml of Histopaque-1077 (Sigma) in a centrifuge tube. The tubes were centrifuged at 800×g for 20 min at room temperature. The white cells at the interphase were collected, diluted with 2 volumes of 0.9% NaCl and centrifuged at 250×g for 10 min at room temperature. The collected cells were suspended and washed twice with RPMI 1640 medium supplemented with 200 mM glutamine, 10 mM non-essential amino acids, penicillin, streptomycin devoid of calf fetal serum. The final sediment was resuspended in the same medium with 10% calf fetal serum and the number of human lymphocytes per ml was determined by counting under the microscope in a Neubauer chamber.

Human lymphocytes were cultured in 96-wells microtiter plates with the RPMI 1640 medium supplemented as described plus 10% calf fetal serum at 37° C. and with 5% $CO_2$. About 30,000 lymphocytes per well were cultured with or without 10 ug per ml of the mitogen PHA, which induce cell proliferation (Yu et al., J. Biol. Chem., 266:7588-7595, 1991). After 48 to 72 h of treatment with PHA, the cells are actively engaged in DNA synthesis as demonstrated by the incorporation of H3-thymidine or BrdU (Yu at al., J. Biol. Chem., 266:7588-7595, 1991). Also, 48 hours after stimulation with PHA, the lymphocytes overexpressed other markers of cell proliferation such as the proliferating cell nuclear antigen or PCNA and Ki-67 (Bantis et al., Cytopathology, 15:25-31, 2004) (FIG. 7). The resting or control lymphocytes did not express these antigens (FIG. 7).

To determine if the stimulated lymphocytes expressed the sense mitochondrial chimeric RNAs, the cells were subjected to in situ hybridization with oligonucleotide probes labeled with digoxigenin and targeted to the sense mitochondrial chimeric RNA. The in situ hybridization protocol employed was described in Example 5. A strong hybridization signal was obtained indicating overexpression of this transcript (FIG. 7). The hybridization signal was similar in intensity to that observed on tumor cells or other normal proliferating cells (compare FIG. 7 with FIGS. 4 A and B, FIGS. 5A and B). No hybridization signal was observed on the control lymphocytes incubated without PHA (FIG. 7).

When the in situ hybridization was carried out with sense oligonucleotide probes labeled with digoxigenin and targeted to the antisense mitochondrial chimeric RNA, an equally strong hybridization signal was obtained (FIG. 7). Several controls were carried out to discard the possibility that the hybridization signal was due to artifacts. The hybridization signal disappears if the in situ hybridization is carry out with the sense labeled probe together with excess (50 to 100 times) of the same sense probe but unlabeled with digoxigenin. If previous to the hybridization the samples are incubated with ribonuclease A overnight, the hybridization signal disappears. Also, no hybridization signal is observed if the hybridization is carried out with sense probes with 4 mistmaches. In contrast, in situ hybridization of non-stimulated lymphocyte showed no hybridization signal (FIG. 7). In conclusion, normal human lymphocytes stimulated to proliferate overexpress both, the sense mitochondrial chimeric RNA and the antisense mitochondrial chimeric RNA. These transcripts are not expressed in resting cells.

Example 9

The Sense Mitochondrial Chimeric RNA Exhibits Different Localizations in Normal and Tumor Cells The in situ hybridizations reported in Examples 5 and 6. Indicated that in several tumor cell lines as well as in tumor cells of human biopsies, the sense mitochondrial chimeric RNA is localized preferentially in the cytoplasm. However, in some tumor biopsies a clear localization of the transcripts in the nucleus was also found (FIG. 4 A, B).

Figure 8:
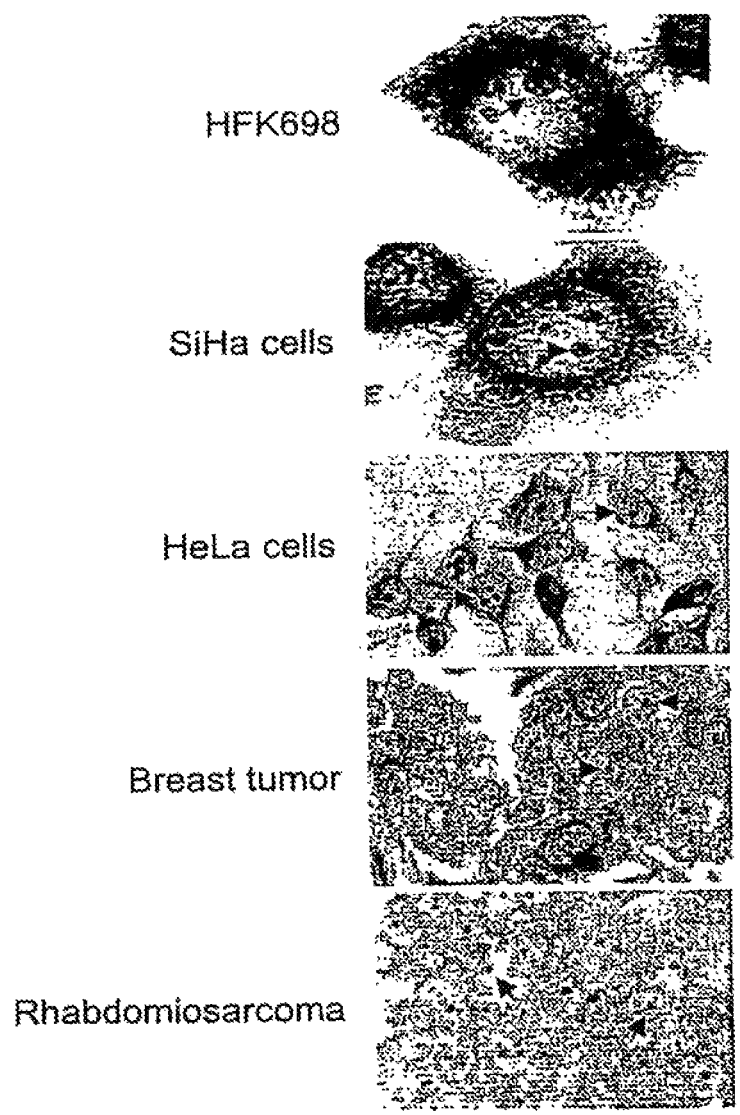
FIG. 8 In situ hybridization of tumor cells showing localization of the sense mitochondrial chimeric RNA in the nucleolus. The cells or tumor sections are indicated at the left.

A surprising finding was the localization of the sense mitochondrial chimeric RNA in the nucleolus. In situ hybridization carried out as reported in Example 5, revealed positive hybridization signal in the nucleolus of Hela and SiHa cells (FIG. 8). The hybridization signal was stronger in the nucleolus of HFK transformed with HPV 16 (FIG. 8). The nucleolar localization has been also found in tumor cells from breast tumors and rhabdomiosarcoma (FIG. 8).

Co-localization studies indicated that the sense mitochondrial chimeric RNA localized in the cytoplasm is outside the mitochondria and associated to late endosomes/lysosomes. If co-localization studies are carried out with markers of mitochondria such as Mitotrack (Molecular Probes), or antibodies anti-cytochrome c (Promega) or anti-Endonuclease G (Chemicon), the in situ hybridization showed a poor co-localization. However, a perfect co-localization was found between the hybridization signal with the immunocytochemistry of late endosemes/lysosomes markers such as Lysotrack (Molecular Probes), or antibodies anti-Lamp-2 (BD Pharmingen) or anti-cathepsin D (Zymed).

Hela cells were subjected to in situ hybridization with oligonucleotide probes labeled with digoxigenin as described in Example 5. After post-hybridization and the whashing procedures, the cells were incubated with an anti-digoxigenin antibody labeled with rhodamine (Roche) and an anti-Lamp-2 antibody labeled with fluoresceine (BD Pharmingen). After incubation at room temperature for 3 h in the dark, the slides were washed, mounted and analyzed with a Zeiss confocal microscope. A clear co-localization of the hybridization signal with the localization of Lamp-2 was obtained. Similar co-localization results of the hybridization signal were obtained when Lysotrack or anti-cathepsin D antibodies were used as markers of the lysosomal fraction. As far as we know, this is the first report showing that a RNA (specially a mitochondrial transcript) is associated to the lysosomes of the cell. Determination of the localization of the sense mitochondrial chimeric RNA in tumor cells may have an important prognostic values for patients with cancer, in general, in normal proliferating cells, the sense and the antisense mitochondrial chimeric RNAs are mainly localized in the nucleus.

Example 10

Treatment of Tumor Cells In Vitro with Antisense Oligonucleotides Targeted to the Antisense Mitochondrial Chimeric RNA Induces Cell Death HL-60 cells were cultured under the optimal conditions recommended by ATCC. About 30,000 cells were cultured in 96-well microtiter plates. Oligonucleotides (2 uM) targeted to the sense or to the antisense mitochondrial chimeric RNA were added. To enhance the permeability of the cells, the oligonucleotides were added in mixture with lipofectamin or oligofectamin (Invitrogen) or with polyethylenimide (PEI) (Exgen TM500, Fermentas). PEI was preferred because is practically non-toxic to the cells. The cells were incubated with the oligonucleotides for 6 h and the percentage of cell survival was determined by permeability to trypan blue. After 6 h incubation with the oligonucleotides an important percentage of the cells died. However, oligonucleotides targeted to the antisense mitochondrial chimeric RNA were more effective to induce cell death (about 90% versus 15% of cell death). On the other hand, no apoptosis was induced when the cells were treated with oligonucleotides targeted to the sense or antisense 12S mitochondrial RNA or the mRNA of ND1 subunit or with scrambled oligonucleotides or oligonucleotides with four mismatches, all of which were used as controls. The oligonucleotides used in these studies contain phosphorothioate linkage in the first 5 nucleotides at the 5' end and the last five nucleotides at the 3' end. On the average, the 10 central nucleotides contain phosphodiester bonds.

To establish if the treatment of the cells with these oligonucleotides induces DNA fragmentation, HL-60 cells were incubated under the same conditions described before with oligonucleotides for 6 h. About 30,000 HL-60 cells were cultured in 200 ul of IDMEM plus 10% calf fetal serum in 96-wells microtiter plate together with 1 uM of oligonucleotides targeted to the sense mitochondrial chimeric RNA or targeted to the antisense mitochondrial chimeric RNA. The chemistry of the oligonucleotides added in mixture with PEI was the same described in the previous section. After an incubation of 6 h with the oligonucleotides the cells were assayed for DNA fragmentation using the TUNEL assay (DeadEnd Colortmetric TUNEL System. Promega). As shown in Table 2, about 96% of the cells showed DNA fragmentation after treatment with the oligonucleotide targeted to the antisense mitochondrial chimeric RNA. Similar rate of DNA fragmentation was obtained with the drug staurosporine. Scrambled oligonucleotides or oligonucleotides with mismatches showed no effect. In contrast, only about 20% of the cells died when treated with oligonucleotide targeted to the sense mitochondrial chimeric RNA (Table 2). As shown previously, tumor cells down regulate the expression of the antisense mitochondrial chimeric RNA and consequently these cells carry a low number of copies of this transcript. Therefore, cell death is more efficiently induced with oligonucleotides targeted to the antisense mitochondrial chimeric RNA. These results strongly suggest that the low number of copies of the antisense mitochondrial chimeric RNA in tumor cells constitute a target for therapy.

TABLE 2

Oligonucleotides complementary to the antisense mitochondrial chimeric RNA induce apoptosis in HL-60 cells.

| Treatment | Percent of apoptotic cells Assayed by TUNEL |
|---|---|
| Control | 3.0% |
| Oligonucleotides complementary to the antisense chimeric RNA | 96.7% |
| Mismatch oligonucleotides | 4.0% |
| Scrambled oligonucleotides | 3.5% |
| Oligonucleotides complementary to the sense chimeric RNA | 26.7% |
| Staurosporine | 98.4% |
| Oligonucleotides complementary to the sense 12 S mitochondrial RNA | 3.7% |
| Oligonucleotides complementary to the antisense 12 S mitochondrial RNA | 4.1% |

Figure 9:
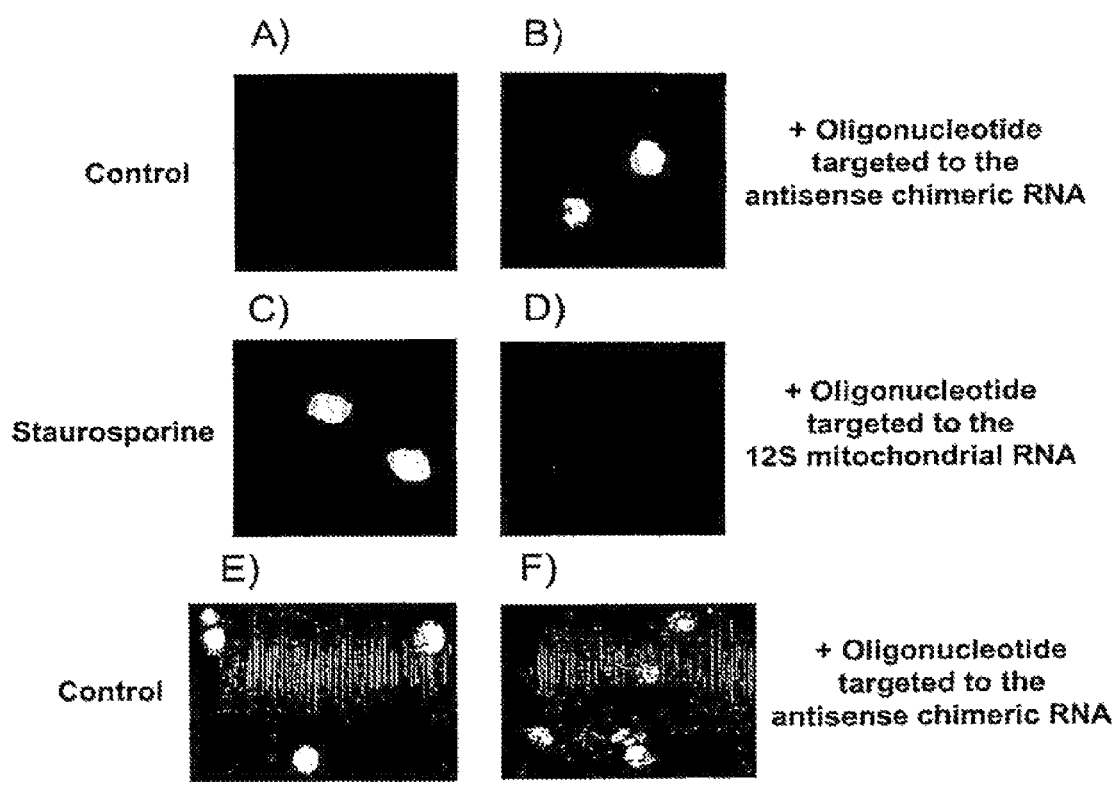
FIG. 9 Fluorescent microscopy to reveal changes occurring in tumoral HL-60 cells treated with oligonucleotides probes targeted to the antisense mitochondrial chimeric RNA. A, B, C and D show staining with a compound (VAD-fmok) that binds with high affinity to activated caspases. This compound is labeled with fluoresceine. The oligonucleotide probes targeted to the antisense mitochondrial chimeric RNA induce activation of caspases in similar manner than the drug staurosporin (compare B and C). Activated caspases are not detected in control untreated cells (A) or in cells treated with oligonucleotide probes targeted to the 12S mitochondrial RNA (D), as control. E and F show staining of HL-60 cells with DAPI. The control cells (untreated) show homogeneous staining of the nucleus (E), while cells treated with the oligonucleotide probes targeted to the antisense mitochondrial chimeric RNA show massive fragmentation of the nucleus (F).

In another study, we determined if the treatment of the cells with oligonucleotides targeted to the antisense mitochondrial chimeric RNA induced caspases activation. Caspases are proteolytic enzymes, actively involved in programmed cell death or apoptosis. HL-60 were incubated with oligonucleotides targeted to the antisense mitochondrial chimeric RNA or with staurosporin for 6 h under the culturing conditions described before. Then, VAD-fmk (CaspaCe FITC-VAD-FMK, Promega) conjugated with fluorescein was added to the culture and incubated for 30 min at 37° C. VAD-fmok is strong inhibitor of caspases and binds to the proteases with very high affinity (Gracia-Calvo et al., J. Biol. Chem., 273:32608-32613, 1998). The cells were washed by centrifugation, mounted and observed with a fluorescence microscope. As shown in FIG. 9, HL-60 cells treated with the oligonucleotide targeted to the antisense mitochondrial chimeric RNA induced activation of caspases, at similar level to the activation achieved with staurosporine. No activation of caspases was obtained with antisense oligonucleotides targeted to the 12S mitochondrial RNA used as control.

The cells treated with oligonucleotides targeted to the antisense mitochondrial chimeric RNA also exhibit other changes that are congruent with apoptosis. Electron microscopy analysis showed nuclear fragmentation and chromatin condensation. Nuclear fragmentation was also demonstrated by staining of the nuclei with DAPI. After treatment with these oligonucleotides targeted to the antisense mitochondrial chimeric RNA, the cells undergo nuclear fragmentation as revealed by DAPI staining (FIGS. 9E and 9F).

Example 11

Other Tumor Cells Also Undergo Cell Death when Treated with Oligonucleotides Complementary to the Antisense Mitochondrial Chimeric RNA Other tumor cells were treated with oligonucleotides complementary to the antisense mitochondrial chimeric RNA according to the protocol described in Example 10. The cells were incubated in their optimal condition according to the recommendation of ATCC, and 2 uM oligonucleotide was added at the initial period of the experiment together with PEI. Six hours later a second addition of the oligonucleotide was carried out at the same concentration and the effect was determined 15 h after the initiation of the experiment. Cell death was determined by DAPI staining and counting the number of cells with fragmented nuclei. As shown in Table 3, over 70% of the cells treated with oligonucleotides undergo apoptosis. It is important to notice, that melanoma cells, lymphoma cells and the breast carcinoma cells MCF/7, known to be quite resistant to drug treatment, undergo apoptosis at a very high rate (Table 3)

TABLE 3

Induction of apoptosis in tumor cell lines by treatment with oligonucleotides complementary to the antisense mitochondrial chimeric RNA.

| Cells | Percent of Apoptotic Cells* (DAPI staining) |
| --- | --- |
| MCF/7 | 89% ± 9 |
| Melanome 4295 | 86% ± 7 |
| Hep G2 | 93% ± 3 |
| Hela | 91% ± 5 |
| DU145 | 89% ± 6 |
| Lymphoma cells Devernelle | 87% ± 5 |
| Caco-2 | 64% ± 7 |

*Treatment was for 15 h and 2 uM oligonucleotides. Apoptosis in cells treated with scrambled or mismatch oligonucleotides, or without oligonucleotides varies between 3 to 10%.

To determine if there are regions in the transcript that are more efficient targets for the oligonucleotides in inducing apoptosis the following experiments were carried out. The induction of apoptosis was studied in Hela, HL-60 and MCF/7 cells with antisense oligonucleotides of about 20 nucleotides, targeted about every 30 nucleotides starting from the 5' end of the antisense mitochondrial chimeric RNA. At time zero 1 uM oligonucleotides were added together with PEI and this treatment was repeated 6 h later. Fifteen hours after the beginning of the treatment, the percent of cell undergoing apoptosis was determined by staining with DAPI and counting the cells with fragmented nuclei. Although most of the oligonucleotides induced a variable degree of apoptosis, the single stranded region of the antisense mitochondrial chimeric RNA was a better target to induce cell death. The oligonucleotides targeted to the putative double stranded or loop structure of the antisense mitochondrial chimeric RNAs were less effective.

Apoptosis can also be determined by trypan blue staining, propidium iodide staining, anexine immunochemistry. In these techniques, the cells can be analyzed by fluorescent microscopy or by flow cytometry. DNA fragmentation can be measured by TUNEL or by electrophoresis to reveal the ladder of DNA. Western blot analysis can also be used to determine the processing of proteins such as caspases, poly (ADP-Rib) synthase, etc.

Example 12

Treatment of Normal Proliferating or Resting Cells with Oligonucleotides Complementary to the Antisense Mitochondrial Chimeric RNA are Refractory to Apoptosis As described before, normal proliferating cells overexpress the sense mitochondrial chimeric RNA as well as the antisense mitochondrial chimeric RNA. Resting cells, on the other hand, are not expressing neither of these transcripts. Therefore, it was important to determine if oligonucleotides complementary to the antisense mitochondrial chimeric RNA induce cell death in normal cells.

Figure 10:
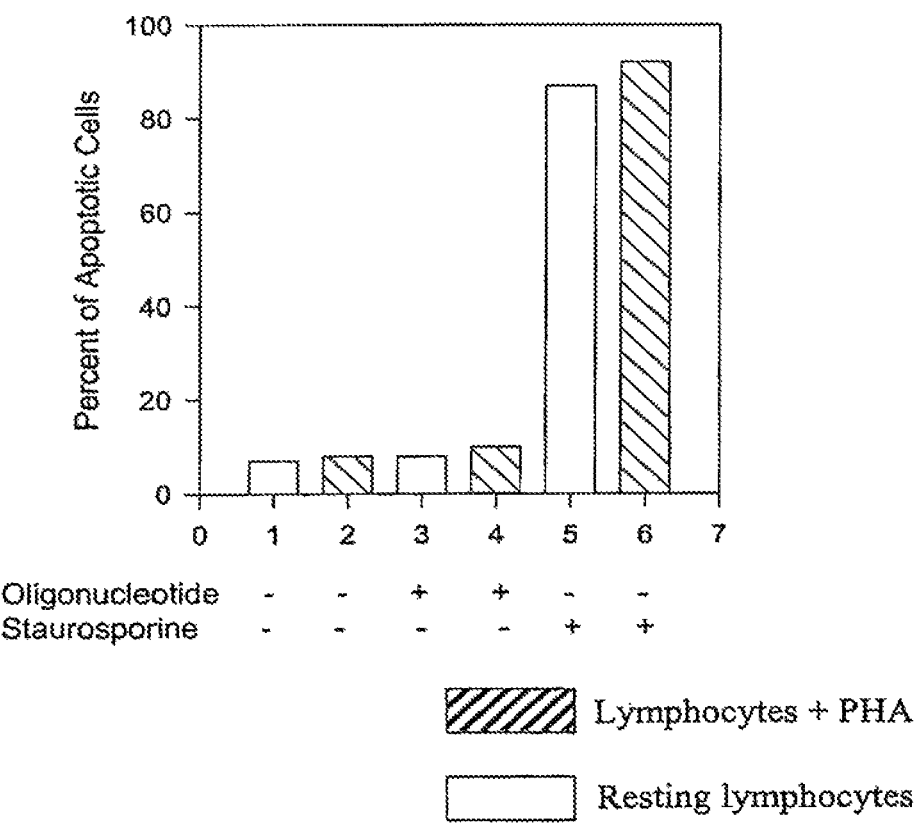
FIG. 10 Percent of apoptotic cells after different treatment conditions of resting and proliferating lymphocytes. Apoptosis was measured in resting lymphocytes or PHA-stimulated lymphocytes by DAPI staining. The bars 1 and 2 correspond to untreated cells. A low spontaneous apoptosis of control (1) or PHA-stimulated lymphocytes (2) was observed. A similar low level of apoptosis was observed in resting lymphocytes (3) or PHA-stimulated lymphocytes (4) treated with 15 uM oligonucleotide probes targeted to the antisense mitochondrial chimeric RNA for 15 h, showing that apoptosis is not induced in normal cells. As a control, resting lymphocytes and PHA-stimulated lymphocyte were treated with staurosporine. Under these conditions, around 90% of resting lymphocytes (5) or PHA-stimulated lymphocytes (6) undergo apoptosis.

Human lymphocytes were stimulated with 10 ug per ml of PHA for 48 h as described in Example 8. In parallel, control lymphocytes were incubated also for 48 h but without PHA. At 48 h of culture, 15 uM of oligonucleotide mixed with PEI (see Example 10) was added to the stimulated and control lymphocytes and further incubated with 15 h. The concentration of the oligonucleotide was 10 fold higher than the concentration used in previous experiments (1-2 uM). Other samples of stimulated or control lymphocytes were treated with 0.4 uM staurosporine for the same period of time. At the end of the experiment, cell death was measured by either trypan blue staining or DAPI staining. As shown in FIG. 10, control lymphocytes or lymphocytes stimulated with PHA incubated for 15 h without oligonucleotide showed a similar level of spontaneous apoptosis that varied between 7 to 10% in different experiments. A similar result was obtained with a lower (1-2 uM) concentration of oligonucleotide. Also, control and stimulated lymphocytes incubated with 15 uM antisense oligonucleotide for 15 h showed similar low level of apoptosis (around 10%) (FIG. 10). In contrast, control lymphocytes or lymphocytes stimulated with PHA and incubated with staurosporine also for 15 h showed that over 80% of the cells undergo apoptosis (FIG. 10). This is a very important result because shows that normal resting cells or normal proliferating cells such as human lymphocytes are refractory to induction of apoptosis by the oligonucleotides complementary to the antisense mitochondrial chimeric RNA. In other words, induction of apoptosis in tumor cells by interfering with the antisense mitochondrial chimeric RNA is a selective therapeutic approach for cancer.

REFERENCES

1. Adrain et al., "Regulation of apoptotic protease activating factor-1 oligomerization and apoptosis by the WD-40 repeat region". J Biol Chem. 274:20865-20860, 1999.
2. Bantis et al. "Expression of p129, Ki-67 and PCNA as proliferation markers in imprint smears of prostate carcinoma and their prognostic value", Cytopathology, 15:25-31, 2004.
3. Beaucage, "Oligodeoxyribonucleotides synthesis. Phosphoramidite approach", Methods Mol. Biol. 20:33-61, 1993.
4. Benedict et al., "Expression and functional analysis of Apaf-1 isoforms. Extra Wd-40 repeat is required for cytochrome c binding and regulated activation of procaspase-9", J Biol. Chem. 275:8461-8468, 2000.
5. Benoist and Chambon, "In vivo requirement of the SV40 early promoter region", Nature 290:304-310, 1981.
6. Boya et al., "Mitochondrion-targeted apoptosis regulators of viral origin", Biochem. Biophys. Res. Commun. 304: 575-581, 2003.

7. Brinster at al., "Regulation of metallothlonein-thymidine kinase fusion plasmids Injected into mouse eggs". Nature 296:39-42, 1982.
8. Burzio et al., "Enviromental bloadhesion: themes and applications", Curr. Opin. Biotechnol., 8:309-312, 1997.
9. Capaldl at al., "Highly efficient solid phase synthesis of oligonucleotide analogs containing phosphorodithioate linkages", Nucleic Acids Res. 28:E40, 2000.
10. Carew and Huang, "Mitochondral defects in cancer", Mol. Cancer, 1:1-12, 2002.
11. Cells, "Cell Biology, A Laboratory Handbook", Julio E. Cells, ed., 1994
12. Chinnery and Tumbull, "Mitochondrial DNA mutations in the pathogenesis of human disease", Mol. Med. Today, 6:425-432, 2000.
13. Clayton and Vinograd, "Circular dimer and catenate forms of mitochondrial DNA in human luekaemic leucocytes", Nature, 216:652-657, 1967.
14. Clayton and Vinograd, "Complex mitochondrialDNA in leukemic and normal human myeloid cells", Proc. Natl. Acad. Sci. US, 62:1077-1084, 1969.
15. Clayton, "Transcription and replication of mitochondrial DNA", Hum Reprod. Suppl 2:11-17, 2000.
16. Comanor et al., "Successful HCV genotyping of previously failed and low viral load specimens using an HCV RNA qualitative assay based on transcription-mediated amplification in conjunction with the line probe assay.", J. Clin Virol., 28:14-26, 2003.
17. Egholm et al., "PNA hybridizes to complementary oligonucleotides obeying the Watson-Crick hydrogen-bonding rules", Nature, 365:566-568, 1993.
18. Elbashir et al. "Duplexes of 21-nucleotides RNAs mediate RNA interference in cultured mammalian cells," Nature 411:494-498, 2001.
19. Falkenberg et al., "Mitochondrial transcription factors 81 and 82 activate transcription of human mtDNA", Nat. Genet. 31:289-294, 2002.
20. Ferri and Kroemer, "Organelle-specific initiation of cell death pathways", Nature Cell Biol. 3:E255-283, 2001.
21. Frederick et al., in "Current Protocols in Molecular Biology", Volume 2, Unit 14, Frederick M. Ausubul et al. eds., 1995.
22. Gracla-Calvo et al., "Inhibition of human caspases by peptide-based and macromolecular inhibitors", J. Biol. Chem., 273:32608-32613, 1998.
23. Guicciardi et al., "Lysosomesin cell death", Oncogene, 23:2881-2890, 2004.
24. Haseloff et al., "Sequence required for self-catalysed cleavage of the satellite RNA of tabacco ringspot virus", Gene, 82:43-52, 1989.
25. Hausen, "Papillomavirus infection—a major cause of human cancer," Biochim. Biophys. Acta, 1288:F55-F78, 1996.
26. Hedge at al., "Commitment to apoptosis induced by tumour necrosis factor-alpha is dependent on caspase activity", Apoptosis, 7:123-132, 2002.
27. Hyrup and Nielsen, "Peptide nucleic acids (PNA): synthesis, properties and potential applications", Bioorg. Med. Chem., 4:5-23, 1996.
28. Johnstone et al., "Apoptosis: a link between cancer genetics and chemotherapy", Cell 108:153-164, 2002.
29. Kobayashi et al., "Genomic structure of HTLV: detection of defective genome and its amplification in MT2 cells", EMBO J., 3:1339-1343, 1984
30. Komarov et al., "A chemical inhibitor of p53 that protect mice from the side effects of cancer therapy", Science 285:1733-1737, 1999.
31. Krammer, "CD95's deadly mission in immune system", Nature 407:789-795, 2000.
32. Li et al., "Endonuclease G is an apoptotic DNase when released from mitochondria", Nature, 412:95-99, 2001.
33. Liu et al., "Synthetic peptides and non-peptidic molecules as probes of structure and function of Bcl-2 family proteins and modulators of apoptosis", Apoptosis, 6:453-462, 2001.
34. Lu et al., "siRNA-mediateted antitumorogenesis for drug target validation and therapeutics," Curr. Opin. Mol. Ther. 5:225-234, 2003.
35. Mag at al., "Synthesis and selective cleavage of an oligodeoxynucleotide containing a bridged internucleotide 5'-phosphorothioate linkage",
36. Martins et al., "The serine protease OmVHtrA2 regulates apoptosis by binding XIAP through a reaper-like motif", J. Biol. Chem. 277:439-444, 2002.
37. McCulloch et al., "A human mitochondrial transcription factor is related to RNA adenine methyltransferases and binds S-adenosylmethionine", Mol. Cell. Biol. 22:1116-1125, 2002.
38. McKay et al., "Characterization of a potent and specific class of antisense oligonucleotide inhibitor of human protein kinase C-α expression", J. Biol. Chem., 274:1715-1722, 1999.
39. McKinnell at al., "The Biological Basis of Cancer, (R:G: McKinnell, R:E: Parchment, A:O: Perantoni, G:B: Pierce, eds.), Ch. 3, Cambridge University Press, UK, 1998
40. McManus et al., "Gene silencing in mammals by small interfering RNAs," Nature Rev. Genet. 3: 737-747, 2002.
41. Meier et al., "Apoptosis in development", Nature 407: 798-801, 2000.
42. Myers et al., "Reverse transcription and DNA amplification by a *Thermus thermophilus* DNA polymerase", Biochemistry, 30:7661-7666, 1991.
43. Nielsen et al., "Peptide nucleic acids (PNA): oligonucleotide analogs with a polyamide backbone", in S. Crooke, B. Lebleu (eds.) Antisense Research and Applications, Ch 9, CRC Press, Boca Raton, Fla., pp. 363-373, 1993.
44. Parisi and Clayton, "Similarity of human mitochondrial transcription factor 1 to high mobility group proteins", Science. 252:965-969, 1991.
45. Parrella et al., "Detection of mitochondrial DNA mutations in primary breast cancer and fine-needle aspirates", Cancer Res., 61:7623-7626, 2001.
46. Rampino et al., "Somatic frameshift mutations in the BAX gene in colon cancers of the microsatellite mutator phenotype", Science, 275:967-969, 1997.
47. Rantanen at al., "Characterization of the mouse genes for mitochondrial transcription factors B1 and B2", Mamm Genome. 14:1-6, 2003.
48. Ravagnan et al., "Heat-shock protein 70 antagonizes apoptosis-inducing factor", Nat Cell Biol. 3:839-843, 2001.
49. Reed, "Dysregulation of apoptosis in cancer". J. Clin. Oncol., 17:2941-2953, 1999.
50. Rossi, "Practical ribozymes. Making ribozymes work in cells", Curr Biol. 4:469-471, 1994.
51. Sambrook et al., Molecular Cloning. A Laboratory Manual, (Sambrook, J., Fritsch, E. T. and Maniatis, T. Eds.,) 2nd Edn, Cold Spring Harbor Laboratory, Cold Spring Harbor, N.Y. 1989.
52. Samejima et al., "CAD/DFF40 nuclease is dispensable for high molecular weight DNA cleavage and stage I chromatin condensation in apoptosis", J Biol. Chem. 276:45427-45432, 2001.
53. Shuey and Attardi, "Characterization of an RNA polymerase activity from HeLa cell mitochondria, which ini- 54. Stephens and Rivers, "Antisense oligonucleotide therapy in cancer", Curr. Opin. Mol. Therapeut., 5:118-122, 2003
55. Summerton, "Morpholino antisense oligomers: a case for an Rnase H-independent structural type", Biochim. Biophys. Acta, 1489:141-158, 1999.
56. Suzuki et al., "A serine protease, Htra2, is <released from the mitochondria and interacts with xiap, inducing cell death", Mol. Cell, 8:613-621, 2001.
57. Taanman, "The mitochondrial genome: structure, transcription, translation and replication", Biochim. Biophys. Acta, 1410:103-123, 1999.
58. Tan et al., "Comprehensive scanning of somatic mitochondrial DNA mutations in breast cancer", Cancer Res., 62:972-076, 2002.
59. Teitz et al., "Caspase 8 is deleted or silenced preferentially in childhood neuroblastomas with amplification of MYCN", Nature Med. 6:529-535, 2000.
60. Tidd et al., "Oligodeoxynucleotide 5mers containing a 5'-CpG induce apoptosis through a mitochondrial mechanism in T lymphocytic leukemia cells," Nucleic Acids Res., 28:2242-2250 (2000).
61. Tiranti et al., "Identification of the gene encoding the human mitochondrial RNA polymerase (h-mtRPOL) by cyberscreening of the Expressed Sequence Tags database", Hum Mol. Genet. 6:615-625, 1997.
62. Verhagen et al., "Cell death regulation by the mammalian IAP antagonist Diablo/Smac", Apoptosis, 7:163-166, 2002.
63. Vickers at al., "Efficient reduction of target RNAs by small interfering RNA and Rnase H-dependent antisense agents", J. Biol. Chem., 278:7108-7118, 2003.
64. Villegas et al., "A novel chimeric mitochondrial RNA localized in the nucleus of mouse sperm", DNA & Cell Biol. 19:579-588, 2000.
65. Villegas at al., "A putative RNA editing from U to C in a mouse mitochondrial transcript", Nucleic Acids Res. 30:1895-1901, 2002.
66. Vogelstein et al., "Surfing the p53 network", Nature 408:307-310, 2000.
67. Wacheck et al., "Small interfering RNA targeting Bcl-2 sensitizes malignant melanoma," Oligonucleotides 13:393-400, 2003.
68. Wagner et al., "Nucleotide sequence of the thymidine kinase gene of herpes simplex virus type 1", Proc. Natl. Acad. Sci. U.S.A. 78:1441-1445, 1981.
69. Wahlestedt et al., "Potent and nontoxic antisense oligonucleotides containing locked nucleic acids", Proc. Natl. Acad. Sci. US, 97:5633-5638, 2000.
70. Warburg, "On the origin of cancer cells", Science, 123:309-314, 1956.
71. Wu at al., "Immunofluorescentlabeling of cancer marker Her2 and other cellular targets with semiconductor quantum dots," Nature Biotechnol. 21:41-46, 2003.
72. Yamamoto et al., "identification of a functional promoter in the long terminal repeat of Rous sarcoma virus", Cell 22:787-797, 1980
73. Yu et al., "Vitamin D receptor expression in human lymphocytes. Signal requirements and characterization by western blots and DNA sequencing", J. Biol. Chem., 266:7588-7595, 1991.
74. Zaug et al., "A labile phosphodiester bond at the ligation-junction in a circular intervening sequence RNA", Science, 224:574-678, 1984.
75. Zörnig et al., "Apoptosis regulators and their role in tumorogenesis", Biochim. Biophys. Acts, 1551:F1-F37, 2001.

What is claimed is:

1. A pharmaceutical composition comprising
   (a) an effective amount of one or more oligonucleotides of 10 to 50 nucleobases in length which are sufficiently complementary to a mitochondrial chimeric RNA molecule comprising
      (i) a sense 16S mitochondrial ribosomal RNA covalently linked at its 5' end to the 3' end of an inverted repeat sequence which is a segment of an antisense 16S mitochondrial ribosomal RNA; or
      (ii) the antisense 16S mitochondrial ribosomal RNA, covalently linked at its 5' end to the 3' end of an inverted repeat sequence which is a segment of the sense 16S mitochondrial ribosomal RNA,
   to be able to hybridize with the mitochondrial chimeric RNA molecule to form a stable duplex and wherein said one or more oligonucleotides comprise at least one alternate internucleoside linkage; and (b) a pharmaceutically acceptable carrier or diluent.

2. The pharmaceutical composition of claim 1, wherein said one or more oligonucleotides of 10 to 50 nucleobases in length is complementary to at least one antisense mitochondrial chimeric RNA molecule comprising a sequence selected from the group consisting of SEQ ID NO:4, SEQ ID NO:5, and SEQ ID NO:6.

3. The pharmaceutical composition of claim 1, wherein said one or more oligonucleotides of 10 to 50 nucleobases in length is complementary to at least one sense mitochondrial chimeric RNA molecule comprising a sequence selected from the group consisting of SEQ ID NO:1, SEQ ID NO:2, and SEQ ID NO:3.

4. The pharmaceutical composition of any one of claims 1-3, which induces at least one of pre-cancer cell death or cancer cell death.

5. The pharmaceutical composition of claim 1, wherein said oligonucleotides further comprise at least one moiety selected from the group consisting of a modified sugar moiety and a modified base moiety.

6. The pharmaceutical composition of claim 1, wherein said one or more oligonucleotides is a ribozyme, a small interfering RNA, or an antisense oligonucleotide.

7. The pharmaceutical composition of claim 1, wherein said pharmaceutically acceptable carrier or diluent comprises one or more components selected from the group consisting of emulsifiers, liposomes, penetration enhancers, surfactants, and chelating agents.

8. The pharmaceutical composition according to claim 1, formulated for a mode of administration selected from the group consisting of topical, oral, buccal, intravenous, subcutaneous, intraperitoneal, intramuscular, rectal, and lung administration via at least one of inhalation or insufflation.

9. The pharmaceutical composition of claim 1, wherein said one or more oligonucleotides are selected from the group consisting of SEQ ID NOs: 9-196.

10. The pharmaceutical composition of claim 1, wherein said at least one alternate internucleoside linkage is one or more of a phosphorothioate internucleosidic linkage, a peptide nucleic acid (PNA) internucleosidic linkage, a phosphoramide internucleosidic linkage, a locked internucleosidic linkage, phosphorodithioate internucleosidic linkage, or a morpholino internucleosidic linkage.

11. The pharmaceutical composition of claim 5, wherein said one or more oligonucleotides comprises at least one modified sugar moiety.

12. The pharmaceutical composition of claim 11, wherein said one or more oligonucleotides comprise at least one 2-o-(2-methoxy)ethyl sugar moiety.

13. The pharmaceutical composition of claim 12, wherein said at least one 2-o-(2-methoxy)ethyl modified sugar moieties is at the 5' and/or 3' ends of the oligonucleotide.

14. The pharmaceutical composition of claim 11, wherein said one or more modified sugar moieties comprise at least one locked oligonucleotide.

15. The pharmaceutical composition of claim 11, wherein said one or more modified sugar moieties comprises arabinose, 2-fluoroarabinose, xylulose, or hexose.

16. The pharmaceutical composition of claim 5, wherein said one or more oligonucleotides comprise at least one modified base moiety.

17. The pharmaceutical composition of claim 16, wherein said at least one modified base moiety comprises 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, or 2,6-diaminopurine.

18. The pharmaceutical composition of claim 5, wherein said one or more oligonucleotides comprise one or more peptidic nucleic acid nucleosidic linkages.

19. A kit comprising:
(a) one or more oligonucleotides of 10 to 50 nucleobases in length which are sufficiently complementary to a mitochondrial chimeric RNA molecule comprising
(i) a sense 16S mitochondrial ribosomal RNA covalently linked at its 5' end to the 3' end of an inverted repeat sequence which is a segment of an antisense 16S mitochondrial ribosomal RNA; or
(ii) the antisense 16S mitochondrial ribosomal RNA, covalently linked at its 5' end to the 3' end of an inverted repeat sequence which is a segment of the sense 16S mitochondrial ribosomal RNA, to be able to hybridize with the mitochondrial chimeric RNA molecule to form a stable duplex and wherein said one or more oligonucleotides comprise at least one alternate internucleoside linkage; and (b) a pharmaceutically acceptable carrier or diluent.

20. The kit of claim 19, wherein said one or more oligonucleotides are selected from the group consisting of SEQ ID NOs: 9-196.

21. The kit of claim 19, wherein said pharmaceutically acceptable carrier or diluent comprises one or more components selected from the group consisting of emulsifiers, liposomes, penetration enhancers, surfactants, and chelating agents.

* * * * *

SEQUENCE LISTING

```
<160> NUMBER OF SEQ ID NOS: 196

<210> SEQ ID NO 1
<211> LENGTH: 2374
<212> TYPE: DNA
<213> ORGANISM: Homo sapiens

<400> SEQUENCE: 1
tctaatactg gtgatgctag aggtgatgtt tttggtaaac aggcggggta agatttgccg      60
agttcctttt actttttta acctttcctt atgagcatgc ctgtgttggg ttgacagtga     120
gggtaataat gacttgttgg ttgattgtag atattgggct gttaattgtc agttcagtgt     180
tttaatctga cgcaggctta tgcggaggag aatgttttca tgttacttat actaacatta     240
gttcttctat agggtgatag attggtccaa ttgggtgtga ggagttcagt tatatgtttg     300 ggattttta ggtagtgggt gttgagcttg aacgctttct taattggtgg ctgcttttag      360
gcctactatg ggtgttaaat tttttactct ctctacaagg ttttttccta gtgtccaaag     420
agctgttcct ctttggacta acagttaaat ttacaagggg atttagaggg ttctgtgggc     480
aaatttaaag ttgaactaag attctatctt ggacaaccag ctatcaccag gctcggtagg     540
tttgtcgcct ctacctataa atcttccac tattttgcta catagacggg tgtgctcttt       600
tagctgttct taggtagctc gtctggtttc gggggtctta gctttggctc tccttgcaaa      660
gttatttcta gttaattcat tatgcagaag gtataggggt tagtccttgc tatattatgc     720
ttggttataa tttttcatct ttcccttgcg gtactatatc tattgcgcca ggtttcaatt     780
```

```
tctatcgcct atactttatt tgggtaaatg gtttggctaa acctagcccc aaacccactc      840
caccttacta ccagacaacc ttagccaaac catttaccca aataaagtat aggcgataga      900
aattgaaacc tggcgcaata gatatagtac cgcaagggaa agatgaaaaa ttataaccaa      960
gcataatata gcaaggacta acccctatac cttctgcata atgaattaac tagaaataac     1020
tttgcaagga gagccaaagc taagacccccc gaaaccagac gagctaccta agaacagcta     1080
aaagagcaca cccgtctatg tagcaaaata gtgggaagat ttataggtag aggcgacaaa     1140
cctaccgagc ctggtgatag ctggttgtcc aagatagaat cttagttcaa ctttaaattt     1200
gcccacagaa ccctctaaat ccccttgtaa atttaactgt tagtccaaag aggaacagct     1260
ctttggacac taggaaaaaa ccttgtagag agagtaaaaa atttaacacc catagtaggc     1320
ctaaaagcag ccaccaatta agaaagcgtt caagctcaac acccactacc taaaaaatcc     1380
caaacatata actgaactcc tcacacccaa ttggaccaat ctatcaccct atagaagaac     1440
taatgttagt ataagtaaca tgaaaacatt ctcctccgca taagcctgcg tcagattaaa     1500
acactgaact gacaattaac agcccaatat ctacaatcaa ccaacaagtc attattaccc     1560
tcactgtcaa cccaacacag gcatgctcat aaggaaaggt taaaaaagt aaaaggaact     1620 cggcaaatct taccccgcct gtttaccaaa acatcacct ctagcatcac cagtattaga     1680
ggcaccgcct gcccagtgac acatgtttaa cggccgcggt accctaaccg tgcaaaggta     1740
gcataatcac ttgttcctta aatagggacc tgtatgaatg gctccacgag ggttcagctg     1800
tctcttactt ttaaccagtg aaattgacct gcccgtgaag aggcgggcat aacacagcaa     1860
gacgagaaga ccctatggag ctttaattta ttaatgcaaa cagtacctaa caaacccaca     1920
ggtcctaaac taccaaacct gcattaaaaa tttcggttgg ggcgacctcg agcagaacc     1980 caacctccga gcagtacatg ctaagacttc accagtcaaa gcgaactact atactcaatt     2040
gatccaataa cttgaccaac ggaacaagtt accctaggga taacagcgca atcctattct     2100
agagtccata tcaacaatag ggtttacgac ctcgatgttg gatcaggaca tcccgatggt     2160
gcagccgcta ttaaaggttc gtttgttcaa cgattaaagt cctacgtgat ctgagttcag     2220
accggagtaa tccaggtcgg tttctatcta ccttcaaatt cctccctgta cgaaggaca      2280 agagaaataa ggcctacttc acaaagcgcc ttcccccgta aatgatatca tctcaactta     2340
gtattatacc cacacccacc caagaacagg gttt                                 2374

<210> SEQ ID NO 2
<211> LENGTH: 1679
<212> TYPE: DNA
<213> ORGANISM: Homo saiens

<400> SEQUENCE: 2
ggggtcttag ctttggctct ccttgcaaag ttatttctag ttaattcatt atgcagaagg       60
tataggggtt agtccttgct atattatgct tggttataat ttttcatctt tcccttgcgg      120
tgctaaacct agccccaaac ccactccacc ttactaccag acaaccttag ccaaaccatt      180
tacccaaata aagtataggc gatagaaatt gaaacctggc gcaatagata tagtaccgca      240
agggaaagat gaaaaattat aaccaagcat aatatagcaa ggactaaccc ctatacctttc     300 tgcataatga attaactaga ataactttg caaggagagc caaagctaag accccccgaaa      360 ccagacgagc tacctaagaa cagctaaaag agcacacccg tctatgtagc aaaatagtgg      420
gaagatttat aggtagaggc gacaaaccta ccgagcctgg tgatagctgg ttgtccaaga      480
```

-continued

| | |
|---|---|
| tagaatctta gttcaacttt aaatttgccc acagaaccct ctaaatcccc ttgtaaattt | 540 |
| aactgttagt ccaaagagga acagctcttt ggacactagg aaaaaacctt gtagagagag | 600 |
| taaaaaattt aacacccata gtaggcctaa aagcagccac caattaagaa agcgttcaag | 660 |
| ctcaacaccc actacctaaa aaatcccaaa catataactg aactcctcac acccaattgg | 720 |
| accaatctat caccctatag aagaactaat gttagtataa gtaacatgaa acattctcc | 780 |
| tccgcataag cctgcgtcag attaaaaacac tgaactgaca attaacagcc caatatctac | 840 |
| aatcaaccaa caagtcatta ttaccctcac tgtcaaccca acacaggcat gctcataagg | 900 |
| aaaggttaaa aaaagtaaaa ggaactcggc aaatcttacc ccgcctgttt accaaaaaca | 960 |
| tcacctctag catcaccagt attagaggca ccgcctgccc agtgacacat gtttaacggc | 1020 |
| cgcggtaccc taaccgtgca aaggtagcat aatcacttgt tccttaaata gggacctgta | 1080 |
| tgaatggctc cacgagggtt cagctgtctc ttacttttaa ccagtgaaat tgacctgccc | 1140 |
| gtgaagaggc gggcataaca cagcaagacg agaagaccct atggagcttt aatttattaa | 1200 |
| tgcaaacagt acctaacaaa cccacaggtc ctaaactacc aaacctgcat taaaaatttc | 1260 |
| ggttggggcg acctcggagc agaacccaac ctccgagcag tacatgctaa gacttcacca | 1320 |
| gtcaaagcga actactatac tcaattgatc caataacttg accaacggaa caagttaccc | 1380 |
| tagggataac agcgcaatcc tattctagag tccatatcaa caatagggtt tacgacctcg | 1440 |
| atgttggatc aggacatccc aatggtgcag ccgctattaa aggttcgttt gttcaacgat | 1500 |
| taaagtccta cgtgatctga gttcagaccg gagtaatcca ggtcggtttc tatctacttc | 1560 |
| aaattcctcc ctgtacgaaa ggacaagaga ataaggcct acttcacaaa gcgccttccc | 1620 |
| ccgtaaatga tatcatctca acttagtatt atacccacac ccacccaaga cagggttt | 1679 |

<210> SEQ ID NO 3
<211> LENGTH: 1635
<212> TYPE: DNA
<213> ORGANISM: Homo sapiens

<400> SEQUENCE: 3

| | |
|---|---|
| ggggtcttag ctttggctct ccttgcaaag ttatttctag ttaattcatt atgcagaagg | 60 |
| tatagggtt agtccttgct aaacctagcc ccaaacccac tccaccttac taccagacaa | 120 |
| ccttagccaa accatttacc caaataaagt ataggcgata gaaattgaaa cctggcgcaa | 180 |
| tagatatagt accgcaaggg aaagatgaaa aattataacc aagcataata tagcaaggac | 240 |
| taaccccctat accttctgca taatgaatta actagaaata actttgcaag gagagccaaa | 300 |
| gctaagaccc ccgaaaccag acgagctacc taagaacagc taaaagagca cacccgtcta | 360 |
| tgtagcaaaa tagtgggaag atttataggt agaggcgaca aacctaccga gcctggtgat | 420 |
| agctggttgt ccaagataga atcttagttc aactttaaat ttgcccacag aaccctctaa | 480 |
| atccccttgt aaatttaact gttagtccaa agaggaacag ctctttggac actaggaaaa | 540 |
| aaccttgtag agagagtaaa aaatttaaca cccatagtag gcctaaaagc agccaccaat | 600 |
| taagaaagcg ttcaagctca cacccacta cctaaaaaat cccaaacata taactgaact | 660 |
| cctcacaccc aattggacca atctatcacc ctatagaaga actaatgtta gtataagtaa | 720 |
| catgaaaaca ttctcctccg cataagcctg cgtcagatta aaacactgaa ctgacaatta | 780 |
| acagcccaat atctacaatc aaccaacaag tcattattac cctcactgtc aacccaacac | 840 |
| aggcatgctc ataaggaaag gttaaaaaaa gtaaaaggaa ctcggcaaat cttaccccgc | 900 |
| ctgtttacca aaaacatcac ctctagcatc accagtatta gaggcaccgc ctgcccagtg | 960 |

| | |
|---|---|
| acacatgttt aacggccgcg gtaccctaac cgtgcaaagg tagcataatc acttgttcct | 1020 |
| taaatagggga cctgtatgaa tggctccacg agggttcagc tgtctcttac ttttaaccag | 1080 |
| tgaaattgac ctgcccgtga agaggcgggc ataacacagc aagacgagaa gaccctatgg | 1140 |
| agctttaatt tattaatgca aacagtacct aacaaaccca caggtcctaa actaccaaac | 1200 |
| ctgcattaaa aatttcggtt ggggcgacct cggagcagaa cccaacctcc gagcagtaca | 1260 |
| tgctaagact tcaccagtca aagcgaacta ctatactcaa ttgatccaat aacttgacca | 1320 |
| acggaacaag ttaccctagg gataacagcg caatcctatt ctagagtcca tatcaacaat | 1380 |
| agggtttacg acctcgatgt tggatcagga catcccaatg gtgcagccgc tattaaaggt | 1440 |
| tcgtttgttc aacgattaaa gtcctacgtg atctgagttc agaccggagt aatccaggtc | 1500 |
| ggtttctatc tacttcaaat tcctccctgt acgaaaggac aagagaaata aggcctactt | 1560 |
| cacaaagcgc cttccccgt aaatgatatc atctcaactt agtattatac ccacacccac | 1620 |
| ccaagaacag ggttt | 1635 |

<210> SEQ ID NO 4
<211> LENGTH: 1921
<212> TYPE: DNA
<213> ORGANISM: Homo sapiens

<400> SEQUENCE: 4

| | |
|---|---|
| aacctccgag cagtacatgc taagacttca ccagtcaaag cgaactacta tactcaattg | 60 |
| atccaataac ttgaccaacg gaacaagtta ccctagggat aacagcgcaa tcctattcta | 120 |
| gagtccatat caacaatagg gtttacgacc tcgatgttgg atcaggacat cccaatggtg | 180 |
| cagccgctat taaaggttcg tttgttcaac gattaaagtc ctacgtgatc tgagttcaga | 240 |
| ccggagtaat ccaggtcggt ttctatctac ttcaaattcc tccctgtacg aaaggacaag | 300 |
| agaaataagg cctacttcac aaagcgcctt ccccgtaaa tgatatcatc tcaacttagt | 360 |
| attatacccct gttcttgggt gggtgtgggt ataatactaa gttgagatga tatcatttac | 420 |
| ggggaaggc gctttgtgaa gtaggcctta tttctcttgt cctttcgtac agggaggaat | 480 |
| ttgaagtaga tagaaaccga cctggattac tccggtctga actcagatca cgtaggactt | 540 |
| taatcgttga acaaacgaac ctttaatagc ggctgcacca tcgggatgtc ctgatccaac | 600 |
| atcgaggtcg taaaccctat tgttgatatg gactctagaa taggattgcg ctgttatccc | 660 |
| tagggtaact tgttccgttg gtcaagttat tggatcaatt gagtatagta gttcgctttg | 720 |
| actggtgaag tcttagcatg tactgctcgg aggttgggtt ctgctccgag gtcgccccaa | 780 |
| ccgaaatttt taatgcaggt ttggtagttt aggacctgtg ggtttgttag gtactgtttg | 840 |
| cattaataaa ttaaagctcc ataggtctt ctcgtcttgc tgtgttatgc ccgcctcttc | 900 |
| acgggcaggt caatttcact ggttaaaagt aagagacagc tgaaccctcg tggagccatt | 960 |
| catacaggtc cctatttaag gaacaagtga ttatgctacc tttgcacggt tagggtaccg | 1020 |
| cggccgttaa acatgtgtca ctgggcaggc ggtgcctcta atactggtga tgctagaggt | 1080 |
| gatgttttg gtaaacaggc ggggtaagat ttgccgagtt cctttactt tttttaacct | 1140 |
| ttccttatga gcatgcctgt gttgggttga cagtgagggg aataatgact tgttggttga | 1200 |
| ttgtagatat tgggctgtta attgtcagtt cagtgtttta atctgacgca ggcttatgcg | 1260 |
| gaggagaatg ttttcatgtt acttatacta acattagttc ttctataggg tgatagattg | 1320 |
| gtccaattgg gtgtgaggag ttcagttata tgtttgggat ttttaggta gtgggtgttg | 1380 |

| | |
|---|---|
| agcttgaacg ctttcttaat tggtggctgc ttttaggcct actatgggtg ttaaatttt | 1440 |
| tactctctct acaaggtttt ttcctagtgt ccaaagagct gttcctcttt ggactaacag | 1500 |
| ttaaatttac aaggggattt agagggttct gtgggcaaat ttaaagttga actaagattc | 1560 |
| tatcttggac aaccagctat caccaggctc ggtaggtttg tcgcctctac ctataaatct | 1620 |
| tcccactatt ttgctacata gacgggtgtg ctcttttagc tgttcttagg tagctcgtct | 1680 |
| ggtttcgggg gtcttagctt tggctctcct tgcaaagtta tttctagtta attcattatg | 1740 |
| cagaaggtat aggggttagt ccttgctata ttatgcttgg ttataatttt tcatctttcc | 1800 |
| cttgcggtac tatatctatt gcgccaggtt tcaatttcta tcgcctatac tttatttggg | 1860 |
| taaatggttt ggctaaggtt gtctggtagt aaggtggagt gggtttgggg ctaggtttag | 1920 |
| c | 1921 |

<210> SEQ ID NO 5
<211> LENGTH: 1744
<212> TYPE: DNA
<213> ORGANISM: Homo sapiens

<400> SEQUENCE: 5

| | |
|---|---|
| tagggataac agcgcaatcc tattctagag tccatatcaa caatagggtt tacgacctcg | 60 |
| atgttggatc aggacatccc gatggtgcag ccgctattaa aggttcgttt gttcaacgat | 120 |
| taaagtccta cgtgatctga gttcagaccg agtaatccca ggtcggtttc tatctacctt | 180 |
| caaattcctc cctgttcttg ggtgggtgtg ggtataatac taagttgaga tgatatcatt | 240 |
| tacggggggaa ggcgctttgt gaagtaggcc ttatttctct tgtcctttcg tacagggagg | 300 |
| aatttgaagt agatagaaac cgacctggat tactccggtc tgaactcaga tcacgtagga | 360 |
| ctttaatcgt tgaacaaacg aacctttaat agccggctgca ccatcgggat gtcctgatcc | 420 |
| aacatcgagg tcgtaaaccc tattgttgat atggactcta aataggatt gcgctgttat | 480 |
| ccctagggta acttgttccg ttggtcaagt tattggatca attgagtata gtagttcgct | 540 |
| ttgactggtg aagtcttagc atgtactgct cggaggttgg gttctgctcc gaggtcgccc | 600 |
| caaccgaaat tttaatgca ggtttggtag tttaggacct gtgggtttgt taggtactgt | 660 |
| ttgcattaat aaattaaagc tccataggt cttctcgtct tgctgtgtta tgcccgcctc | 720 |
| ttcacgggca ggtcaatttc actggttaaa agtaagagac agctgaaccc tcgtggagcc | 780 |
| attcatacag gtccctattt aaggaacaag tgattatgct acctttgcac ggttagggta | 840 |
| ccgcggccgt taaacatgtg tcactgggca ggcggtgcct ctaatactgg tgatgctaga | 900 |
| ggtgatgttt ttggtaaaca ggcggggtaa gatttgccga gttccttta ctttttttaa | 960 |
| cctttcctta tgagcatgcc tgtgttgggt tgacagtgag ggtaataatg acttgttggt | 1020 |
| tgattgtaga tattgggctg ttaattgtca gttcagtgtt ttaatctgac gcaggcttat | 1080 |
| gcggaggaga atgttttcat gttacttata ctaacattag ttcttctata gggtgataga | 1140 |
| ttggtccaat tgggtgtgag gagttcagtt atatgtttgg gattttttag gtagtgggtg | 1200 |
| ttgagcttga acgctttctt aattggtggc tgcttttagg cctactatgg gtgttaaatt | 1260 |
| ttttactctc tctacaaggt ttttttcctag tgtccaaaga gctgttcctc tttggactaa | 1320 |
| cagttaaatt tacaagggga tttagagggt tctgtgggca aatttaaagt tgaactaaga | 1380 |
| ttctatcttg gacaaccagc tatcaccagg ctcggtaggt tgtcgcctc tacctataaa | 1440 |
| tcttcccact attttgctac atagacgggt gtgctctttt agctgttctt aggtagctcg | 1500 |
| tctggtttcg ggggtcttag ctttggctct ccttgcaaag ttatttctag ttaattcatt | 1560 |

```
atgcagaagg tatagggtt agtccttgct atattatgct tggttataat ttttcatctt    1620
tcccttgcgg tactatatct attgcgccag gtttcaattt ctatcgccta tactttattt    1680
gggtaaatgg tttggctaag gttgtctggt agtaaggtgg agtgggtttg gggctaggtt    1740
tagc                                                                 1744

<210> SEQ ID NO 6
<211> LENGTH: 1854
<212> TYPE: DNA
<213> ORGANISM: Homo sapiens

<400> SEQUENCE: 6
gaactcggca atcttaccc cgcctgttta ccaaaaacat cacctctagc atcaccagta      60
ttagaggcac cgcctgccca gtgacacatg tttaacggcc gcggtaccct aaccgtgcaa    120
aggtagcata atcacttgtt ccttaaatag ggacctgtat gaatggctcc acgagggttc    180
agctgtctct tacttttaac cagtgaaatt gacctgcccg tgaagaggcg ggcatgacac    240
agcaagacga aagacccta tggagcttta atttattaat gcaaacagta cctaacaaac     300
cctgttcttg ggtgggtgtg ggtataaatac taagttgaga tgatatcatt tacgggggaa    360
ggcgctttgt gaagtaggcc ttatttctct tgtccttcg tacagggagg aatttgaagt     420
agatagaaac cgacctggat tactccggtc tgaactcaga tcacgtagga ctttaatcgt    480
tgaacaaacg aacctttaat agcggctgca ccatcgggat gtcctgatcc aacatcgagg    540
tcgtaaaccc tattgttgat atggactcta gaataggatt gcgctgttat ccctagggta    600
acttgttccg ttggtcaagt tattggatca attgagtata gtagttcgct ttgactggtg    660
aagtcttagc atgtactgct cggaggttgg gttctgctcc gaggtcgccc caaccgaaat    720
ttttaatgca ggtttggtag tttaggacct gtgggtttgt taggtactgt ttgcattaat    780
aaattaaagc tccataggt cttctcgtct tgctgtgtta tgcccgcctc ttcacgggca     840
ggtcaatttc actggttaaa agtaagagac agctgaaccc tcgtggagcc attcatacag    900 gtccctatt aaggaacaag tgattatgct accttgcac ggttagggta ccgcggccgt      960
taaacatgtg tcactgggca ggcggtgcct ctaatactgg tgatgctaga ggtgatgttt    1020
ttggtaaaca ggcggggtaa gatttgccga gttccttta ctttttttaa cctttcctta    1080
tgagcatgcc tgtgttgggt tgacagtgag ggtaataatg acttgttggt tgattgtaga    1140
tattgggctg ttaattgtca gttcagtgtt taatctgac gcaggcttat gcggaggaga    1200
atgttttcat gttacttata ctaacattag ttcttctata gggtgataga ttggtccaat    1260
tgggtgtgag gagttcagtt atatgtttgg gatttttag gtagtgggtg ttgagcttga    1320
acgctttctt aattggtggc tgcttttagg cctactatgg gtgttaaatt ttttactctc    1380
tctacaaggt tttttcctag tgtccaaaga gctgttcctc tttggactaa cagttaaatt    1440
tacaagggga tttagagggt tctgtgggca aatttaaagt tgaactaaga ttctatcttg    1500
gacaaccagc tatcaccagg ctcggtaggt ttgtcgcctc tacctataaa tcttcccact    1560
attttgctac atagacgggt gtgctctttt agctgttctt aggtagctcg tctggtttcg    1620
ggggtcttag ctttggctct ccttgcaaag ttatttctag ttaattcatt atgcagaagg    1680 tatagggtt agtccttgct atattatgct tggttataat ttttcatctt tcccttgcgg    1740
tactatatct attgcgccag gtttcaattt ctatcgccta tactttattt gggtaaatgg    1800
tttggctaag gttgtctggt agtaaggtgg agtgggtttg gggctaggtt tagc          1854
```

<210> SEQ ID NO 7
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 7
taggtttagc accgcaaggg                                          20

<210> SEQ ID NO 8
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 8
taggtttagc aaggactaac                                          20

<210> SEQ ID NO 9
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 9
ggggtaagat ttgccgag                                            18

<210> SEQ ID NO 10
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 10
atgctagagg tgatgttttt gg                                       22

<210> SEQ ID NO 11
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 11
cggtgcctct aatactgg                                            18

<210> SEQ ID NO 12
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 12
gttaaacatg tgtcactggg                                          20

<210> SEQ ID NO 13
<211> LENGTH: 18
<212> TYPE: DNA
<213> ORGANISM: Artificial Sequence
<220> FEATURE:
<223> OTHER INFORMATION: Antisense Oligonucleotide

```
<400> SEQUENCE: 13
ttgcacggtt agggtacc                                                    18

<210> SEQ ID NO 14
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 14
ggaacaagtg attatgctac c                                                21

<210> SEQ ID NO 15
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 15
ggagccattc atacaggtcc c                                                21

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
agtaagagac agctgaaccc                                                  20

<210> SEQ ID NO 17
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 17
ggcaggtcaa tttcactgg                                                   19

<210> SEQ ID NO 18
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 18
gctgtgttat gcccgcctc                                                   19

<210> SEQ ID NO 19
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 19
agctccatag ggtcttctc                                                   19

<210> SEQ ID NO 20
```

```
<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
gttaggtact gtttgcatta                                              20

<210> SEQ ID NO 21
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 21
aagtcttagc atgtactg                                                18

<210> SEQ ID NO 22
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 22
tagtagttcg ctttgactg                                               19

<210> SEQ ID NO 23
<211> LENGTH: 19
<212> TYPE: DNA
<213> ORGANISM: Artificial Sequence
<220> FEATURE:
<223> OTHER INFORMATION: OAntisense Oligonucleotide

<400> SEQUENCE: 23
caagttattg gatcaattg                                               19

<210> SEQ ID NO 24
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 24
gggtaacttg ttccgttg                                                18

<210> SEQ ID NO 25
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 25
aataggattg cgctgtta                                                18

<210> SEQ ID NO 26
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 26
```

-continued cctattgttg atatggac                                              18

<210> SEQ ID NO 27
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 27
ctgatccaac atcgagg                                               17

<210> SEQ ID NO 28
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 28
tagcggctgc accattgg                                              18

<210> SEQ ID NO 29
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 29
gttgaacaaa cgaaccttt                                             19

<210> SEQ ID NO 30
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 30
aactcagatc acgtaggac                                             19

<210> SEQ ID NO 31
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 31
cgacctggat tactccgg                                              18

<210> SEQ ID NO 32
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 32
ggaatttgaa gtagatag                                              18

<210> SEQ ID NO 33
<211> LENGTH: 19
<212> TYPE: DNA

```
<213> ORGANISM: Artificial Sequence
<220> FEATURE:
<223> OTHER INFORMATION: Antisense Oligonucleotide

<400> SEQUENCE: 33
ctcttgtcct ttcgtacag                                              19

<210> SEQ ID NO 34
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 34
ggcgctttgt gaagtagg                                               18

<210> SEQ ID NO 35
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 35
gttgagatga tatcatttac gg                                          22

<210> SEQ ID NO 36
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 36
cacccaccca agaacagg                                               18

<210> SEQ ID NO 37
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 37
caacttagta ttatacccac accca                                       25

<210> SEQ ID NO 38
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 38
tcccccgtaa atgattacat ct                                          22

<210> SEQ ID NO 39
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 39
gagaaataag gcctacttca caaag                                       25
```

-continued

<210> SEQ ID NO 40
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 40
caaattcctc cctgtacgaa ag                                        22

<210> SEQ ID NO 41
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 41
agtaatccag gtcggtttct atct                                      24

<210> SEQ ID NO 42
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 42
aagtcctagc tgatctgagt tcag                                      24

<210> SEQ ID NO 43
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 43
gctattaaag gttcgtttgt tcaac                                     25

<210> SEQ ID NO 44
<211> LENGTH: 16
<212> TYPE: DNA
<213> ORGANISM: Artificial Sequence
<220> FEATURE:
<223> OTHER INFORMATION: Antisense Oligonucleotide

<400> SEQUENCE: 44
tcccgatggt gcagcc                                               16

<210> SEQ ID NO 45
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 45
ttacgacctc gatgttggat ca                                        22

<210> SEQ ID NO 46
<211> LENGTH: 25
<212> TYPE: DNA
<213> ORGANISM: Artificial Sequence
<220> FEATURE:

```
<223> OTHER INFORMATION: Antisense Oligonucleotide

<400> SEQUENCE: 46
atcctattct agagtccata tcaac                                          25

<210> SEQ ID NO 47
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 47
aataggattg cgctgttatc ccta                                           24

<210> SEQ ID NO 48
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 48
tagggataac agcgcatacc tatt                                           24

<210> SEQ ID NO 49
<211> LENGTH: 23
<212> TYPE: DNA
<213> ORGANISM: Artificial Sequence
<220> FEATURE:
<223> OTHER INFORMATION: Antisense Oligonucleotide

<400> SEQUENCE: 49
ggaacaagtt accctaggga taa                                            23

<210> SEQ ID NO 50
<211> LENGTH: 23
<212> TYPE: DNA
<213> ORGANISM: Artificial Sequence
<220> FEATURE:
<223> OTHER INFORMATION: Antisense Oligonucleotide

<400> SEQUENCE: 50
ttgatccaat aacttgacca acg                                            23

<210> SEQ ID NO 51
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 51
acttcaccag tcaaagcgaa c                                              21

<210> SEQ ID NO 52
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 52
aacccaacct ccgagcag                                                  18
```

```
<210> SEQ ID NO 53
<211> LENGTH: 16
<212> TYPE: DNA
<213> ORGANISM: Artificial Sequence
<220> FEATURE:
<223> OTHER INFORMATION: Antisense Oligonucleotide

<400> SEQUENCE: 53
gttggggcga cctcgg                                                       16

<210> SEQ ID NO 54
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 54
aaactaccaa acctgcttaa aa                                                22

<210> SEQ ID NO 55
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 55
aaacagtacc taacaaaccc acag                                              24

<210> SEQ ID NO 56
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 56
gaccctatgg agctttaatt tatta                                             25

<210> SEQ ID NO 57
<211> LENGTH: 23
<212> TYPE: DNA
<213> ORGANISM: Artificial Sequence
<220> FEATURE:
<223> OTHER INFORMATION: Antisense Oligonucleotide

<400> SEQUENCE: 57
cataacacag caagacgaga aga                                               23

<210> SEQ ID NO 58
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 58
tgacctgccc gtgaagag                                                     18

<210> SEQ ID NO 59
<211> LENGTH: 26
<212> TYPE: DNA
<213> ORGANISM: Artificial Sequence
<220> FEATURE:
<223> OTHER INFORMATION: Antisense Oligonucleotide
```

```
<400> SEQUENCE: 59
cagctgtctc ttacttttaa ccagtg                                          26

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
ctgtatgaat ggctccacga                                                 20

<210> SEQ ID NO 61
<211> LENGTH: 26
<212> TYPE: DNA
<213> ORGANISM: Artificial Sequence
<220> FEATURE:
<223> OTHER INFORMATION: Antisense Oligonucleotide

<400> SEQUENCE: 61
agcataatca cttgttcctt aaatag                                          26

<210> SEQ ID NO 62
<211> LENGTH: 23
<212> TYPE: DNA
<213> ORGANISM: Artificial Sequence
<220> FEATURE:
<223> OTHER INFORMATION: Antisense Oligonucleotide

<400> SEQUENCE: 62
accgtgcaaa ggtagcataa tca                                             23

<210> SEQ ID NO 63
<211> LENGTH: 23
<212> TYPE: DNA
<213> ORGANISM: Artificial Sequence
<220> FEATURE:
<223> OTHER INFORMATION: Antisense Oligonucleotide

<400> SEQUENCE: 63
tgattatgct acctttgcac ggt                                             23

<210> SEQ ID NO 64
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 64
gtaccctaac cgtgcaaag                                                  19

<210> SEQ ID NO 65
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 65 cctgcccagtgacacatgtt t                                                21

<210> SEQ ID NO 66
<211> LENGTH: 25
```

```
<212> TYPE: DNA
<213> ORGANISM: Artificial Sequence
<220> FEATURE:
<223> OTHER INFORMATION: Antisense Oligonucleotide

<400> SEQUENCE: 66
cacctctagc atcaccagta ttaga                                              25

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
cttaccccgc ctgtttacca                                                    20

<210> SEQ ID NO 68
<211> LENGTH: 26
<212> TYPE: DNA
<213> ORGANISM: Artificial Sequence
<220> FEATURE:
<223> OTHER INFORMATION: Antisense Oligonucleotide

<400> SEQUENCE: 68
aggttaaaaa aagtaaaagg aactcg                                             26

<210> SEQ ID NO 69
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 69
cccaacacag gcatgctca                                                     19

<210> SEQ ID NO 70
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 70
accaacaagt cattattacc ctca                                               24

<210> SEQ ID NO 71
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 71
tgacaattaa cagcccaata tcta                                               24

<210> SEQ ID NO 72
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 72
```
gcctgcgtca gattaaaaca c                                          21

<210> SEQ ID NO 73
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 73
gtaacatgaa aacattctcc tccg                                       24

<210> SEQ ID NO 74
<211> LENGTH: 28
<212> TYPE: DNA
<213> ORGANISM: Artificial Sequence
<220> FEATURE:
<223> OTHER INFORMATION: Antisense Oligonucleotide

<400> SEQUENCE: 74
tatcacccta tagaagaact aatgttag                                   28

<210> SEQ ID NO 75
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 75
ctgaactcct cacacccaat t                                          21

<210> SEQ ID NO 76
<211> LENGTH: 23
<212> TYPE: DNA
<213> ORGANISM: Artificial Sequence
<220> FEATURE:
<223> OTHER INFORMATION: Antisense Oligonucleotide

<400> SEQUENCE: 76
cactacctaa aaatcccaa aca                                         23

<210> SEQ ID NO 77
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 77
ttaagaaagc gttcaagctc a                                          21

<210> SEQ ID NO 78
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 78
catagtaggc ctaaaagcag c                                          21

<210> SEQ ID NO 79
<211> LENGTH: 26
<212> TYPE: DNA
<213> ORGANISM: Artificial Sequence

```
<220> FEATURE:
<223> OTHER INFORMATION: Antisense Oligonucleotide

<400> SEQUENCE: 79
aaaccttgta gagagagtaa aaaatt                                          26

<210> SEQ ID NO 80
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 80
aaagaggaac agctctttgg acac                                            24

<210> SEQ ID NO 81
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 81
aatccccttg taaatttaac tgtt                                            24

<210> SEQ ID NO 82
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 82
ctttaaattt gcccacagaa c                                               21

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
ggttgtccaa gatagaatct                                                 20

<210> SEQ ID NO 84
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 84
acaaacctac cgagcctgg                                                  19

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
aagatttata ggtagaggcg                                                 20
```

```
<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
cccgtctatg tagcaaaata                                          20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
acctaagaac agctaaaaga                                          20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
taagaccccc gaaaccagac                                          20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
ataactttgc aaggagagcc                                          20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
cttctgcata atgaattaac                                          20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
atatagcaag gactaacccc                                          20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 92
agatgaaaaa ttataaccaa                                        20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
caatagatat agtaccgcaa                                        20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
aggcgataga aattgaaacc                                        20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
tagccaaacc atttacccaa                                        20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
caccttacta ccagacaacc                                        20

<210> SEQ ID NO 97
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 97
ctaaacctag ccccaaacc                                         19

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98
ctagcatcac cagtattaga                                        20

<210> SEQ ID NO 99
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
ttaccaaaaa catcacctct                                              20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
gaactcggca aatcttaccc                                              20

<210> SEQ ID NO 101
<211> LENGTH: 20
<212> TYPE: DNA
<213> ORGANISM: Artificial Sequence
<220> FEATURE:
<223> OTHER INFORMATION: Sense Oligonucleotide

<400> SEQUENCE: 101
gggtaagatt tgccgagttc                                              20

<210> SEQ ID NO 102
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 102
gctcataagg aaaggttaaa a                                            21

<210> SEQ ID NO 103
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 103
gtcaacccaa cacaggc                                                 17

<210> SEQ ID NO 104
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 104
accaacaagt cattattacc c                                            21

<210> SEQ ID NO 105
<211> LENGTH: 22
<212> TYPE: DNA
<213> ORGANISM: Artificial Sequence
<220> FEATURE:
<223> OTHER INFORMATION: Sense Oligonucleotide

<400> SEQUENCE: 105
```

```
ggttgattgt agatattggg ct                                          22

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
attaacagcc caatatctac                                             20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107
tgcgtcagat taaaacactg                                             20

<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108
aaaacattct cctccgcata                                             20

<210> SEQ ID NO 109
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 109
gttagtataa gtaacatg                                               18

<210> SEQ ID NO 110
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 110
tggaccaatc tatcaccct                                              19

<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
acatataact gaactcctca                                             20

<210> SEQ ID NO 112
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 112
cacccactac ctaaaaaatc                                              20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
caccaattaa gaaagcgttg                                              20

<210> SEQ ID NO 114
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 114
taggcctaaa agcagccacc aa                                           22

<210> SEQ ID NO 115
<211> LENGTH: 22
<212> TYPE: DNA
<213> ORGANISM: Artificial Sequence
<220> FEATURE:
<223> OTHER INFORMATION: Sense Oligonucleotide

<400> SEQUENCE: 115
ttggtggctg cttttaggcc ta                                           22

<210> SEQ ID NO 116
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 116
taacacccat agtaggcct                                               19

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
aaccttgtag agagagtaaa                                              20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
aacagctctt tggacactag                                              20
```

<210> SEQ ID NO 119
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 119
aactgttagt ccaaagag                                                 18

<210> SEQ ID NO 120
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 120
ctctaaatcc ccttgtaaa                                                19

<210> SEQ ID NO 121
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 121
actttaaatt tgcccacag                                                19

<210> SEQ ID NO 122
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 122
ggttgtccaa gatagaatc                                                19

<210> SEQ ID NO 123
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 123
acaaacctac cgagcctcc                                                19

<210> SEQ ID NO 124
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 124
atttataggt tagaggcg                                                 18

<210> SEQ ID NO 125
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 125
atgtagcaaa atagtgggaa                                               20

<210> SEQ ID NO 126
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 126
taagaacagc taaaagagca c                                             21

<210> SEQ ID NO 127
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 127
cgaaaccaga cgagctac                                                 18

<210> SEQ ID NO 128
<211> LENGTH: 22
<212> TYPE: DNA
<213> ORGANISM: Artificial Sequence
<220> FEATURE:
<223> OTHER INFORMATION: Sense Oligonucleotide

<400> SEQUENCE: 128
ggggtcttag ctttggctct cc                                            22

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129
taactttgca aggagagcca                                               20

<210> SEQ ID NO 130
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 130
accttctgca taatgaat                                                 18

<210> SEQ ID NO 131
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 131
atatagcaag gactaaccc                                                19
```

```
<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
gatgaaaaat tataaccaag                                                 20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133
aatagatata gtaccgcaag                                                 20

<210> SEQ ID NO 134
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 134
cgatagaaat tgaaacc                                                    17

<210> SEQ ID NO 135
<211> LENGTH: 20
<212> TYPE: DNA
<213> ORGANISM: Artificial Sequence
<220> FEATURE:
<223> OTHER INFORMATION: Sense Oligonucleotide

<400> SEQUENCE: 135
tactttattt gggtaaatgg                                                 20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
ccatttaccc aaataaagta                                                 20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
ttagccaaac catttaccca                                                 20

<210> SEQ ID NO 138
<211> LENGTH: 21
<212> TYPE: DNA
<213> ORGANISM: Artificial Sequence
<220> FEATURE:
<223> OTHER INFORMATION: Antisense Oligonucleotide
```

```
<400> SEQUENCE: 138
aaggtggagt gggtttgggg c                                              21

<210> SEQ ID NO 139
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 139
gctaaggttg tctggta                                                   17

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 140
atcgcctata ctttatttgg                                                20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
atctattgcg ccaggtttca                                                20

<210> SEQ ID NO 142
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 142
ttttcatctt tcccttgcg                                                 19

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143
tccttgctat attatgcttg                                                20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 144
cattatgcag aaggtatagg                                                20

<210> SEQ ID NO 145
<211> LENGTH: 18
```

-continued

<210> SEQ ID NO 145
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 145
tctccttgca aagttatt                                                    18

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 146
tttcgggggt cttagctttg                                                  20

<210> SEQ ID NO 147
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 147
ctgttcttag gtagctcg                                                    18

<210> SEQ ID NO 148
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 148
tgctacatag acgggtgtg                                                   19

<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149
cctctaccta taaatcttcc                                                  20

<210> SEQ ID NO 150
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 150
gctatcacca ggctcgg                                                     17

<210> SEQ ID NO 151
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 151

```
aagttgaact aagattc                                          17

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 152
gagggttctg tgggcaaatt                                       20

<210> SEQ ID NO 153
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 153
acagttaaat ttacaaggg                                        19

<210> SEQ ID NO 154
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 154
gtgtccaaag agctgttcc                                        19

<210> SEQ ID NO 155
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 155
tactctctct acaaggtttt                                       20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 156
taggcctact atgggtgtta                                       20

<210> SEQ ID NO 157
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 157
aacgctttct taattggtgg c                                     21

<210> SEQ ID NO 158
<211> LENGTH: 20
<212> TYPE: DNA
<213> ORGANISM: Artificial Sequence
```

```
<220> FEATURE:
<223> OTHER INFORMATION: Antisense Oligonucleotide

<400> SEQUENCE: 158
ttttaggtag tgggtgttga                                              20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
ggagttcagt tatatgtttg                                              20

<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 160
tgatagattg gtccaattgg                                              20

<210> SEQ ID NO 161
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 161
ctaacattag ttcttctata g                                            21

<210> SEQ ID NO 162
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 162
atgcggagga gaatgttt                                                18

<210> SEQ ID NO 163
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 163
tcagtgtttt aatctgacg                                               19

<210> SEQ ID NO 164
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 164
gtagatattg ggctgttaatt                                             21
```

<210> SEQ ID NO 165
<211> LENGTH: 20
<212> TYPE: DNA
<213> ORGANISM: Artificial Sequence
<220> FEATURE:
<223> OTHER INFORMATION: Oligonucleotide

<400> SEQUENCE: 165
gtgagggtaa taatgacttg                                              20

<210> SEQ ID NO 166
<211> LENGTH: 20
<212> TYPE: DNA
<213> ORGANISM: Artificial Sequence
<220> FEATURE:
<223> OTHER INFORMATION: Oligonucleotide

<400> SEQUENCE: 166
atgagcatgc ctgtgttggt                                              20

<210> SEQ ID NO 167
<211> LENGTH: 19
<212> TYPE: DNA
<213> ORGANISM: Artificial Sequence
<220> FEATURE:
<223> OTHER INFORMATION: Oligonucleotide

<400> SEQUENCE: 167
ggtaagattt gccgagttc                                               19

<210> SEQ ID NO 168
<211> LENGTH: 20
<212> TYPE: DNA
<213> ORGANISM: Artificial Sequence
<220> FEATURE:
<223> OTHER INFORMATION: Oligonucleotide

<400> SEQUENCE: 168
tggtgatgct agaggtgatg                                              20

<210> SEQ ID NO 169
<211> LENGTH: 15
<212> TYPE: DNA
<213> ORGANISM: Artificial Sequence
<220> FEATURE:
<223> OTHER INFORMATION: Oligonucleotide

<400> SEQUENCE: 169
gcggtgcctc taata                                                   15

<210> SEQ ID NO 170
<211> LENGTH: 20
<212> TYPE: DNA
<213> ORGANISM: Artificial Sequence
<220> FEATURE:
<223> OTHER INFORMATION: Oligonucleotide

<400> SEQUENCE: 170
ggccgttaaa catgtgtcac                                              20

<210> SEQ ID NO 171
<211> LENGTH: 20
<212> TYPE: DNA
<213> ORGANISM: Artificial Sequence
<220> FEATURE:
<223> OTHER INFORMATION: Oligonucleotide

```
<400> SEQUENCE: 171
tgattatgct acctttgcac                                          20

<210> SEQ ID NO 172
<211> LENGTH: 20
<212> TYPE: DNA
<213> ORGANISM: Artificial Sequence
<220> FEATURE:
<223> OTHER INFORMATION: Oligonucleotide

<400> SEQUENCE: 172
ttaaggaaca agtgattatg                                          20

<210> SEQ ID NO 173
<211> LENGTH: 20
<212> TYPE: DNA
<213> ORGANISM: Artificial Sequence
<220> FEATURE:
<223> OTHER INFORMATION: Oligonucleotide

<400> SEQUENCE: 173
tggagccatt catacaggtc                                          20

<210> SEQ ID NO 174
<211> LENGTH: 20
<212> TYPE: DNA
<213> ORGANISM: Artificial Sequence
<220> FEATURE:
<223> OTHER INFORMATION: Oligonucleotide

<400> SEQUENCE: 174
aaaagtaaga gacagctgaa                                          20

<210> SEQ ID NO 175
<211> LENGTH: 20
<212> TYPE: DNA
<213> ORGANISM: Artificial Sequence
<220> FEATURE:
<223> OTHER INFORMATION: Oligonucleotide

<400> SEQUENCE: 175
cacgggcagg tcaatttcac                                          20

<210> SEQ ID NO 176
<211> LENGTH: 20
<212> TYPE: DNA
<213> ORGANISM: Artificial Sequence
<220> FEATURE:
<223> OTHER INFORMATION: Oligonucleotide

<400> SEQUENCE: 176
gtcttgctgt gttatgcccg                                          20

<210> SEQ ID NO 177
<211> LENGTH: 19
<212> TYPE: DNA
<213> ORGANISM: Artificial Sequence
<220> FEATURE:
<223> OTHER INFORMATION: Oligonucleotide

<400> SEQUENCE: 177
aattaaagct ccatagggt                                           19

<210> SEQ ID NO 178
```

```
<211> LENGTH: 21
<212> TYPE: DNA
<213> ORGANISM: Artificial Sequence
<220> FEATURE:
<223> OTHER INFORMATION: Oligonucleotide

<400> SEQUENCE: 178
gtttgttagg tactgtttgc a                                              21

<210> SEQ ID NO 179
<211> LENGTH: 19
<212> TYPE: DNA
<213> ORGANISM: Artificial Sequence
<220> FEATURE:
<223> OTHER INFORMATION: Oligonucleotide

<400> SEQUENCE: 179
aggtttggta gtttaggac                                                 19

<210> SEQ ID NO 180
<211> LENGTH: 20
<212> TYPE: DNA
<213> ORGANISM: Artificial Sequence
<220> FEATURE:
<223> OTHER INFORMATION: Oligonucleotide

<400> SEQUENCE: 180
gccccaaccg aaattttaa                                                 20

<210> SEQ ID NO 181
<211> LENGTH: 20
<212> TYPE: DNA
<213> ORGANISM: Artificial Sequence
<220> FEATURE:
<223> OTHER INFORMATION: Oligonucleotide

<400> SEQUENCE: 181
ctcggaggtt gggttctgct                                                20

<210> SEQ ID NO 182
<211> LENGTH: 20
<212> TYPE: DNA
<213> ORGANISM: Artificial Sequence
<220> FEATURE:
<223> OTHER INFORMATION: Oligonucleotide

<400> SEQUENCE: 182
ctggtgaagt cttagcatgt                                                20

<210> SEQ ID NO 183
<211> LENGTH: 20
<212> TYPE: DNA
<213> ORGANISM: Artificial Sequence
<220> FEATURE:
<223> OTHER INFORMATION: Oligonucleotide

<400> SEQUENCE: 183
caattgagta tagtagttcg                                                20

<210> SEQ ID NO 184
<211> LENGTH: 19
<212> TYPE: DNA
<213> ORGANISM: Artificial Sequence
<220> FEATURE:
<223> OTHER INFORMATION: Oligonucleotide

<400> SEQUENCE: 184
```

```
tgttccgttg gtcaagtta                                          19

<210> SEQ ID NO 185
<211> LENGTH: 20
<212> TYPE: DNA
<213> ORGANISM: Artificial Sequence
<220> FEATURE:
<223> OTHER INFORMATION: Oligonucleotide

<400> SEQUENCE: 185
aataggattg cgctgttatc                                         20

<210> SEQ ID NO 186
<211> LENGTH: 20
<212> TYPE: DNA
<213> ORGANISM: Artificial Sequence
<220> FEATURE:
<223> OTHER INFORMATION: Oligonucleotide

<400> SEQUENCE: 186
attgttgata tggactctag                                         20

<210> SEQ ID NO 187
<211> LENGTH: 20
<212> TYPE: DNA
<213> ORGANISM: Artificial Sequence
<220> FEATURE:
<223> OTHER INFORMATION: Oligonucleotide

<400> SEQUENCE: 187
atccaacatc gaggtcgtaa                                         20

<210> SEQ ID NO 188
<211> LENGTH: 19
<212> TYPE: DNA
<213> ORGANISM: Artificial Sequence
<220> FEATURE:
<223> OTHER INFORMATION: Oligonucleotide

<400> SEQUENCE: 188
gcggctgcac catcgggat                                          19

<210> SEQ ID NO 189
<211> LENGTH: 19
<212> TYPE: DNA
<213> ORGANISM: Artificial Sequence
<220> FEATURE:
<223> OTHER INFORMATION: Oligonucleotide

<400> SEQUENCE: 189
ttgaacaaac gaacctta                                           19

<210> SEQ ID NO 190
<211> LENGTH: 20
<212> TYPE: DNA
<213> ORGANISM: Artificial Sequence
<220> FEATURE:
<223> OTHER INFORMATION: Oligonucleotide

<400> SEQUENCE: 190
aactcagatc acgtaggact                                         20

<210> SEQ ID NO 191
<211> LENGTH: 19
<212> TYPE: DNA
```

```
<213> ORGANISM: Artificial Sequence
<220> FEATURE:
<223> OTHER INFORMATION: Oligonucleotide

<400> SEQUENCE: 191
aaaccgacct ggattactc                                           19

<210> SEQ ID NO 192
<211> LENGTH: 20
<212> TYPE: DNA
<213> ORGANISM: Artificial Sequence
<220> FEATURE:
<223> OTHER INFORMATION: Oligonucleotide

<400> SEQUENCE: 192
agggaggaat ttgaaggtag                                          20

<210> SEQ ID NO 193
<211> LENGTH: 20
<212> TYPE: DNA
<213> ORGANISM: Artificial Sequence
<220> FEATURE:
<223> OTHER INFORMATION: Oligonucleotide

<400> SEQUENCE: 193
ggccttattt ctcttgtcct                                          20

<210> SEQ ID NO 194
<211> LENGTH: 20
<212> TYPE: DNA
<213> ORGANISM: Artificial Sequence
<220> FEATURE:
<223> OTHER INFORMATION: Oligonucleotide

<400> SEQUENCE: 194
ggaaggcgct ttgtgaagta                                          20

<210> SEQ ID NO 195
<211> LENGTH: 20
<212> TYPE: DNA
<213> ORGANISM: Artificial Sequence
<220> FEATURE:
<223> OTHER INFORMATION: Oligonucleotide

<400> SEQUENCE: 195
aagttgagat gatatcattt                                          20

<210> SEQ ID NO 196
<211> LENGTH: 17
<212> TYPE: DNA
<213> ORGANISM: Artificial Sequence
<220> FEATURE:
<223> OTHER INFORMATION: Oligonucleotide

<400> SEQUENCE: 196
cctgttcttg ggtgggt                                             17
```